US008969573B2

(12) United States Patent
Chorev et al.

(10) Patent No.: US 8,969,573 B2
(45) Date of Patent: Mar. 3, 2015

(54) COMPOUNDS FOR THE INHIBITION OF CELLULAR PROLIFERATION

(75) Inventors: Michael Chorev, Chestnut Hill, MA (US); Bertal Huseyin Aktas, Newton, MA (US); Jose A. Halperin, Brookline, MA (US); Gerhard Wagner, Chestnut Hill, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/807,132

(22) PCT Filed: Jun. 28, 2011

(86) PCT No.: PCT/US2011/042139
§ 371 (c)(1),
(2), (4) Date: Mar. 21, 2013

(87) PCT Pub. No.: WO2012/006068
PCT Pub. Date: Jan. 12, 2012

(65) Prior Publication Data
US 2013/0178505 A1 Jul. 11, 2013

Related U.S. Application Data

(60) Provisional application No. 61/359,227, filed on Jun. 28, 2010.

(51) Int. Cl.
*C07D 417/02* (2006.01)
*C07D 277/38* (2006.01)
*C07D 241/02* (2006.01)
(Continued)

(52) U.S. Cl.
CPC ............ *C07D 277/84* (2013.01); *C07D 233/88* (2013.01); *C07D 263/48* (2013.01); *C07D 277/50* (2013.01); *C07D 417/04* (2013.01); *C07D 417/10* (2013.01);
(Continued)

(58) Field of Classification Search
USPC .......................................... 546/209; 514/366
See application file for complete search history.

(56) References Cited

U.S. PATENT DOCUMENTS

| 4,826,868 | A | * | 5/1989 | Wachter et al. | ................ | 514/407 |
| 6,025,375 | A | * | 2/2000 | Taniguchi et al. | ............ | 514/374 |
| 2012/0309735 | A1 | * | 12/2012 | Altman et al. | ............. | 514/210.2 |

FOREIGN PATENT DOCUMENTS

| EP | 1762568 A1 | 3/2007 |
| WO | 92/10475 A1 | 6/1992 |

(Continued)

OTHER PUBLICATIONS

Moerke; Cell, 2007,128, 257-267.*
(Continued)

*Primary Examiner* — John Mabry
*Assistant Examiner* — Daniel Carcanague
(74) *Attorney, Agent, or Firm* — Banner & Witcoff, Ltd.

(57) ABSTRACT

Compositions and methods for inhibiting translation are provided. Compositions, methods and kits for treating (1) cellular proliferative disorders, (2) non-proliferative, degenerative disorders, (3) viral infections, (4) disorders associated with viral infections, and/or (5) non-proliferative metabolic disorders such as type II diabetes where inhibition of translation initiation is beneficial using the compounds disclosed herein.

1 Claim, 1 Drawing Sheet

(51) Int. Cl.
    A61K 31/381    (2006.01)
    A61K 31/496    (2006.01)
    C07D 277/84    (2006.01)
    C07D 233/88    (2006.01)
    C07D 263/48    (2006.01)
    C07D 277/50    (2006.01)
    C07D 417/04    (2006.01)
    C07D 417/10    (2006.01)
    C07D 417/12    (2006.01)
    C07D 277/30    (2006.01)
    C07D 277/42    (2006.01)
    C07D 513/04    (2006.01)

(52) U.S. Cl.
    CPC .......... *C07D 417/12* (2013.01); *C07D 277/30* (2013.01); *C07D 277/42* (2013.01); *C07D 513/04* (2013.01)
    USPC ......... 546/270.4; 546/209; 514/366; 514/342

(56) References Cited

FOREIGN PATENT DOCUMENTS

| | | | |
|---|---|---|---|
| WO | WO9210475 | * | 6/1992 |
| WO | 97/05877 | A1 | 2/1997 |
| WO | WO9705877 | * | 2/1997 |
| WO | WO 98/46599 | * | 10/1998 |
| WO | 2006/078942 | A2 | 7/2006 |
| WO | 2007/028999 | A1 | 3/2007 |
| WO | WO2007028999 | * | 3/2007 |
| WO | 2008/021849 | A2 | 2/2008 |
| WO | WO2008021849 | * | 2/2008 |

OTHER PUBLICATIONS

Khazi; Indian Journal of Heterocyclic Chemistry, 1995, 4, 243-248.*
Wermuth; Practice of Medicinal Chemistry 3rd Ed. Elsevier. 2008, chapter 6.*
Bowles; Synlett, 1993, 111-112.*
Guzikowski; J. Med. Chem. 2000, 43, 984-994.*
Antonysamy; Bioorg. Med. Chem. Lett. 18 (2008) 2990-2995.*
Bilanges, B., et al., "Mechanisms of Translational Deregulation in Human Tumors and Therapeutic Intervention Strategies," 2007, pp. 5973-5990.
Meric, Funda, et al., "Translation Initiation in Cancer: A Novel Target for Therapy," 2002, pp. 971-979, vol. 1.
Rosenwald, Igor B., et al., "Expression of Translation Initiation Factor eIF-2α is Increased in Benign and Malignant Melanocytic and Colonic Epithelial Neoplasms," 2003, pp. 1080-1088.
Rosenwald, Igor B., et al., "The Role of Translation in Neoplastic Transformation from a Pathologist's Point of View," 2004, pp. 3230-3247.
Silverman, R.B.,"The Organic Chemistry of Drug Design and Drug Addiction," 1992, pp. 19-23, Academic Press, Inc., San Diego, California.
Wang, Songtao, et al., "Expression of the Eukaryotic Translation Initiation Factors 4E and 2α in Non-Hodgkin's Lymphomas" American Journal of Pathology, Jul. 1999, pp. 247-255, vol. 155, No. 1.
Wang, Songtao, et al., "Expression of Eukaryotic Translation Initiation Factors 4E and 2α Correlates with the Progression of Thyroid Carcinoma," 2001, pp. 1101-1107, vol. 11, No. 12.
Watkins, S. J., et al., "Translation Initiation and its Deregulation During Tumorigenesis," 2002, pp. 1023-1027.
Patent Examination Report issued in corresponding Australian Application No. 2011276539, dated Mar. 21, 2014.
Bowles, S. et al. "A Convenient Preparation of Cyclic Ether Acetals Mediated by Trifluoroacetic Anhydride." Synlett, 1993, 111-112.
Guzikowski, A. et al. "Synthesis of N-Substituted 4-(4-Hydroxyphenyl)piperidines, 4-(4-Hydroxybenzyl) pipiredines, and (+−)-3-(4-Hydroxyphenyl)pyrrolidines: Selective Antagonists at the 1A/2B NMDA Receptor Subtype." Journal of Medicinal Chemistry, 2000, 43, 984-994.
Moerke, N. et al. "Small-Molecule Inhibition of the Interaction between the Translation initiation Factors eIF4E and eIF4G". Cell, 2007, 128, 257-267.
Extended European Search Report issued from corresponding EP Application No. 11804117.7, dated Sep. 23, 2014.
Moerke, Nathan J. et al.,"Small-Molecule Inhibition of the Interaction between the Translation Initiation Factors eiF4E and eIF4G" Cell, Jan. 26, 2007, pp. 257-267, vol. 128, No. 2, Elsevier Inc.

* cited by examiner

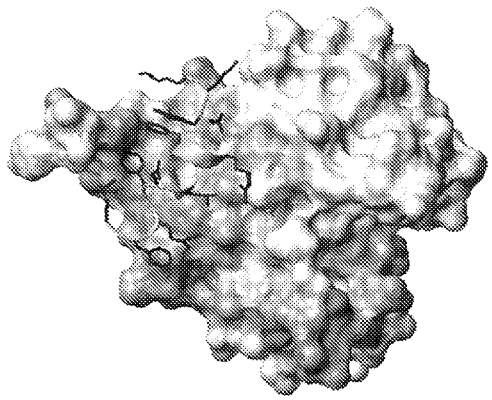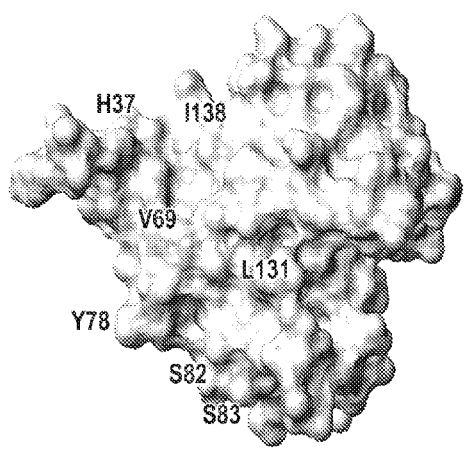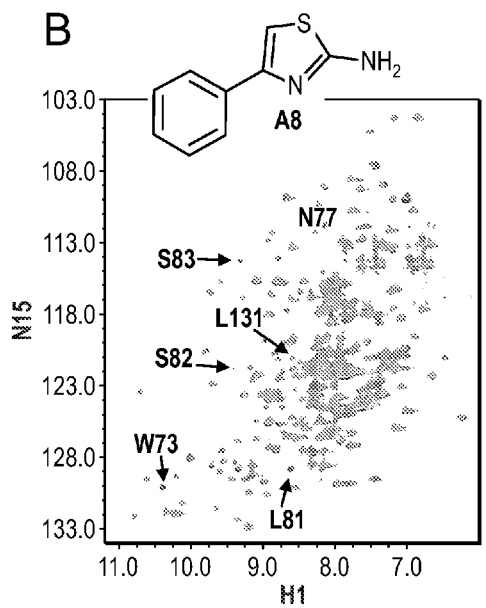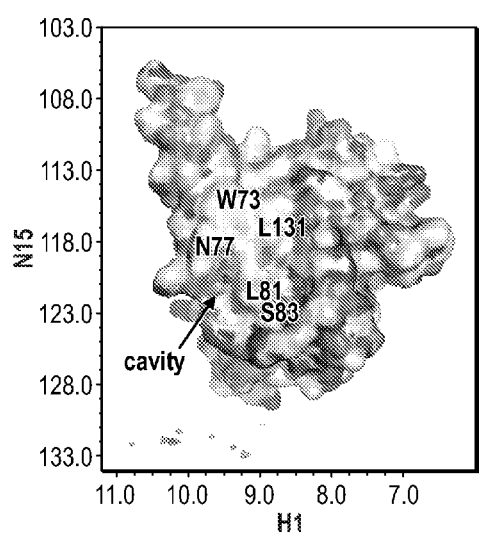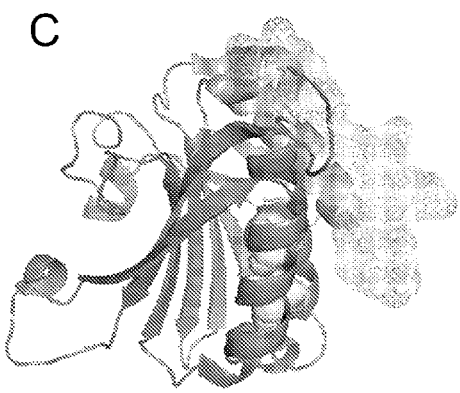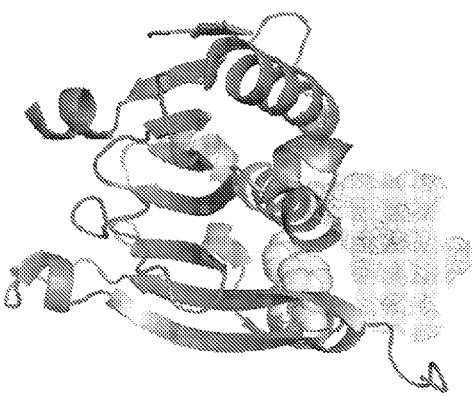

COMPOUNDS FOR THE INHIBITION OF CELLULAR PROLIFERATION

RELATED APPLICATION DATA

This application is a National Stage Application under 35 U.S.C. 371 of co-pending PCT application PCT/US2011/042139 designating the United States and filed Jun. 28, 2011; which claims the benefit of Provisional patent application No. 61/359,227 and filed Jun. 28, 2010 each of which are hereby incorporated by reference in their entireties.

STATEMENT OF GOVERNMENT INTERESTS

This invention was made with Government support under Grant Number R01 CA121357 awarded by the National Institutes of Health. The Government has certain rights in the invention.

FIELD

The present invention relates to novel compounds which inhibit translation initiation, pharmaceutical compositions of the novel compounds, and methods of treating medical disorders.

BACKGROUND

The regulation of protein synthesis at the level of translation initiation plays a key role in the control of cell growth, proliferation, and apoptosis. Translation, the mRNA-directed synthesis of proteins, occurs in three distinct steps: initiation, elongation and termination. Translation initiation is a complex process in which the two ribosomal subunits and methionyl tRNA (met-tRNAi) assemble on a properly aligned mRNA to commence chain elongation at the AUG initiation codon. The interaction between the initiation factors eIF4E and eIF4G is a major component of this process. eIF4E binds the 7-methylguanosine cap structure found at the 5' ends of most messenger RNAs. Its binding partner eIF4G, a scaffold protein, provides a docking site for other initiation factors, including the RNA helicase eIF4A. Collectively, eIF4E, eIF4G, and eIF4A form a ternary complex referred to as eIF4F. Once assembled, this complex recruits the 40S ribosomal subunit to the 5' end of the mRNA molecule as a result of the interaction of eIF3 with eIF4G, followed by scanning of the 40S subunit to the initiation codon where it joins with the 60S subunit. This process is facilitated by eIF4A, with the requirement for its helicase activity being directly proportional to the amount of secondary structure in the 5' UTR that must be melted for scanning to occur.

Translation initiation is a critical step in the regulation of cell growth because the expression of most oncogenes and cell growth regulatory proteins is translationally regulated. Biosynthesis of many growth-promoting proteins is suppressed on the translation-initiation level, and several forms of cancer exhibit an out-of-balance translation initiation machinery. Although inhibitors of translation exist, most, if not all, act nonspecifically on all translation.

Many types of tumor cells are characterized by aberrant protein translation initiation mechanisms, e.g., association or binding of certain translation initiation factors. For example, the interaction of the cap-binding protein eIF4E with the mRNA cap, the scaffold protein eIF4G, and the regulatory 4E-BPs, are involved in cell transformation. Small-molecule inhibitors of the eIF4E/eIF4G interaction have been identified and found to possess anti-tumor activity.

Recruitment of the capped 5' end of an mRNA to the small ribosomal subunit is thought to be the major rate limiting step in eukaryotic translation initiation. This process is tightly regulated and requires the stepwise assembly of a large multiprotein complex centered around the trimeric complex eIF4F, comprised of the translation initiation factors eIF4E, eIF4G, and eIF4A. Cap-bound eIF4F recruits the 40S ribosomal subunit through the interaction of eIF3 with eIF4G, which initiates scanning to the initiation codon where it joins with the 60S subunit. This process is facilitated by eIF4A, with the requirement for its helicase activity directly proportional to the amount of secondary structure in the 5' UTR that must be melted for scanning to occur. All eIF4G proteins bind eIF4E through a motif of sequence $Y(X)_4L\Phi$, where X is variable and $\Phi$ is hydrophobic. This motif forms a helical peptide structure which binds a conserved surface of hydrophobic residues on the dorsal side of eIF4E.

Cellular mRNAs differ greatly in their requirement for eIF4F for efficient translation and in the composition of the 5' UTR. The majority of growth and proliferation related proteins are encoded by "weak" mRNAs containing long highly structured 5' UTRs which have lower translational efficiency than "strong" mRNAs, which contain relatively short and unstructured 5' UTRs. Translation of weak mRNAs is highly eIF4F dependent and is preferentially enhanced when the level of eIF4F complex is increased by eIF4E overexpression. The amount of eIF4E available for complex formation is controlled by a class of small proteins termed 4E-BPs which contain the $Y(X)_4L\Phi$ motif and bind to the same surface as eIF4G. In response to stimuli such as nutrients and growth factors 4E-BPs undergo a set of hierarchical phosphorylation events. Hyperphosphorylated forms of 4E-BPs bind eIF4E much more weakly than hypophosphorylated forms, and thus 4E-BP phosphorylation acts as a switch to up-regulate the level of eIF4F and cap-dependent translation. Misregulation of cap-dependent translation due to overexpression of eIF4E and the other components of the eIF4F complex is thought to play an important role in the development of many forms of cancer. In cultured mammalian cells overexpression of eIF4E or eIF4G induces malignant transformation while overexpression of 4E-BP 1 partially reverses transformation by eIF4E. In addition, etopic expression of nonphosphorylatable forms of 4E-BP1 can inhibit proliferation and/or induce apoptosis in cancer cell lines. Inhibition of the eIF4F complex is useful for cancer therapy. See PCT/US2006/002093 hereby incorporated by reference its entirety herein.

The disruption of proper translational regulation by elevated levels of eIF4F complexes is an important factor in carcinogenesis. A wide variety of tumors have been found to have abnormally elevated eIF4E levels, and eIF4G is amplified in some lung cancers. The overexpression of eIF4E in cultured cells can cause them to exhibit a malignant transformed phenotype: rapid proliferation, loss of contact inhibition, and anchorage-independent growth. This transformation is dependent on eIF4E's ability to bind eIF4G, as co-expression of 4E-BP1 in these cells can partially reverse their malignant properties. Elevated eIF4E levels are detected in cancers of the breast, head, neck, bladder, colon, prostate, gastrointestinal tract and lung, Hodgkin's lymphomas, and neuroblastomas. In breast cancer patients, the risk of cancer recurrence and cancer-related death is correlated with the level of eIF4E overexpression. The other components of eIF4F are overexpressed in specific types of cancer: eIF4G in squamous cell lung carcinomas, and eIF4A in melanomas and primary hepatocellular carcinomas.

Loss of proper regulation of the eIF4E-eIF4G interaction plays an important role in the development of many cancers.

The protein-protein interaction between eIF4E and eIF4G is an essential step in cap-dependent translation initiation. Because the translation of the mRNAs encoding most proteins involved in cellular growth and proliferation is highly cap-dependent, regulation of the level of complex formation between eIF4E and eIF4G plays an important role in the control of these processes. The interaction between these proteins is inhibited by the 4E binding proteins (4E-BPs), which compete with eIF4G for binding to the same surface on eIF4E. Phosphorylation of specific sites on 4E-BPs in response to growth and proliferation signals inhibits their ability to bind eIF4E.

The level of eIF4E/eIF4G complex formation also plays a role in the control of apoptosis. 4E-BP 1 has been found to undergo a caspase cleavage of its N-terminus which removes a motif necessary for it to undergo phosphorylation, leading to increased 4E-BP 1 binding to eIF4E and inhibition of cap-dependent translation. This inhibition causes a shift in the levels of pro and anti apopoptic proteins to favor apoptosis. Experiments in cultured cells have shown that peptides containing the eIF4E recognition motif of eIF4G fused to a penetratin sequence can induce apoptosis.

In general, translation initiation is beneficial for inhibiting cellular proliferative disorders, whether cancerous or non-cancerous and translation initiation is an accepted target for cancer treatments. See Funda Meric and Kelly Hunt, Translation Initiation in Cancer: A Novel Target for Therapy, *Molecular Cancer Therapeutics*, Vol. 1, 971-979, September 2002; S. J. Watkins and C. J. Norbury, Translation Initiation and Its Deregulation During Tumorigenesis, *British Journal of Cancer* (2002) 86, 1023-1027; Igor Rosenwald, The Role of Translation in Neoplastic Transformation from a Pathologist's Point of View, *Oncogene* (2004) 23, 3230-3247; Igor Rosenwald, Songtao Wang, Lou Savas, Bruce Woda, James Pullman, Expression of Translation Initiation Factor eIF-2α is Increased in Benign and Malignant Melanocytic and Colonic Epithelial Neoplasms, *Cancer*, Vol. 98, No. 5, (2003); Songtao Wang, Igor Rosenwald, Michael Hutzler, German Pihan, Lou Savas, Jane-Jane Chen and Bruce Woda, Expression of the Eukaryotic Translation Initiation Factors 4E and 2α in Non-Hodgkin's Lymphomas, *American Journal of Pathology*, Vol. 155, 247-255 (1999); B. Bilanges and D. Stokoe, Mechanisms of Translational Deregulation in Human Tumors and Therapeutic Intervention Strategies, *Oncogene* (2007) 26, 5973-5990; Songtao Wang, Ricardo Lloyd, Michael Hutzler, Igor Rosenwald, Marjorie Safran, Nilima Patwardhan and Ashraf Khan, Expression of Eukaryotic Translation Initiation Factors 4E and 2α Correlates with the Progression of Thyroid Carcinoma, *Thyroid*, Vol. 11, No. 12 1101-1107 (2001).

SUMMARY

Embodiments of the present invention are directed to compounds and methods that inhibit translation initiation and selectively suppress synthesis of growth factors and oncogene products. In particular, embodiments of the present invention are directed to compounds and methods of inhibiting the protein-protein interaction between eukaryotic translation initiation factors eIF4E and eIF4G. As indicated in FIG. 1, according to NMR chemical shift mapping, fragment mapping and mutation data for compound 4EGI-1, the compounds of the present invention bind to a conserved region of hydrophobic residues and a small cavity delineated by Phe$^{72}$ and Tyr$^{76}$ and overlapping with the surface region of eIF4E that is recognized by a conserved helical peptide motif in eIF4G, thus blocking the interaction of these two proteins. In contrast to traditional inhibitors of translation (e.g., cyclohexamide) which act non-specifically, the compounds of the present invention are selective inhibitors of cap-dependent translation, a significant improvement over existing general inhibitors of protein synthesis. Such compounds and methods are useful for treating (1) proliferative disorders, (2) non-proliferative, degenerative disorders, (3) viral infections, (4) disorders associated with viral infections and/or (5) non-proliferative metabolic disorders such as type II diabetes where inhibition of translation initiation is beneficial.

In at least certain examples, the compounds of the present invention are effective to inhibit translation. In certain examples, the compounds of the present invention are effective to inhibit cellular proliferation. In another example, the compounds of the present invention are effective to inhibit viral infections. In another example, the compounds of the present invention are effective to treat or relieve symptoms associated with proliferative disorders, non-proliferative, degenerative disorders, viral infections, and/or non-proliferative metabolic disorders.

Some of the compounds described herein contain one or more centers of asymmetry and may give rise to diastereoisomers and optical isomers. The present invention is meant to include such diastereoisomers as well as their racemic and resolved, optically active forms. Optically active (R) and (S) isomers may be resolved using conventional techniques. Some of the compounds described herein contain olefinic double bonds, and unless otherwise specified, are meant to include both E and Z geometric isomers.

In accordance with a method aspect, a method of treating a cellular proliferative disorder by providing and/or administering a compound of Formula I to a mammal, e.g., a human or a non-human (e.g., a non-human primate), is provided. In one example, the cellular proliferative disorder is cancer. In accordance with other examples, a method of treating a viral infection by providing and/or administering a compound of Formula I to a mammal, e.g. a human or a non-human mammal, is provided.

In accordance with an additional aspect, kits are provided for the treatment of (1) proliferative disorders, (2) non-proliferative, degenerative disorders, (3) viral infections, and/or (4) disorders associated with viral infections. In one aspect, the kits comprise a compound of Formula I, a pharmaceutically acceptable carrier, and optionally, instructions for use. The pharmaceutical composition can be administered to a human subject or a non-human subject depending on the disorder to be treated.

It will be recognized by the person of ordinary skill in the art that the compounds, compositions, methods and kits disclosed herein provide significant advantages over prior technology. Compounds, compositions, methods and kits can be designed or selected to relieve and/or alleviate symptoms in a patient suffering from one or more disorders. These and other aspects and examples are described below.

BRIEF DESCRIPTION OF THE DRAWINGS

The foregoing and other features and advantages of the present invention will be more fully understood from the following detailed description of illustrative embodiments taken in conjunction with the accompanying drawings.

FIG. 1 depicts binding site characterization experiments carried out for compound 4EGI-1 and fragment A8: A. NMR Titration of 4EGI-1 with eIF4E causes chemical shifts and line broadening of residues H37, V69, Y78, S82, S83, and L131, I138 thus outlining the 4EGI-1 binding site. B. Left side—NMR titration of A8 a fragment of 4EGI-1 causes chemical shift changes at its binding site. The residues affected are W73, N77, L81, S82, S83, and L131. Right side—Molecular modeling of the NMR titration data delineates the binding cavity of A8. C. Mutants F72A (phenylalanine at position 72 replaced by alanine indicated by yellow spheres) and F76A (phenylalanine at position 76 replaced by alanine indicated by yellow spheres) of eIF4E bind 4EGI-1 (light blue space filling shapes) with higher affinity suggesting that enlargement of the binding cavity to better accommodate 4EGI-1 binding. Left side—side view and Right side—top view.

It will be recognized that the results and examples in the figures are only illustrative and other examples and illustrations will be readily recognized by the person of ordinary skill in the art, given the benefit of this disclosure.

DETAILED DESCRIPTION OF CERTAIN EMBODIMENTS

In accordance with certain examples, compounds of Formula I and other compounds described herein inhibit translation (e.g., translation initiation) and cellular proliferation. Such compounds are useful for the treatment of (1) proliferative disorders, (2) non-proliferative, degenerative disorders, (3) viral infections, (4) disorders associated with viral infections, and/or (5) non-proliferative metabolic disorders such as type II diabetes where inhibition of translation initiation is beneficial.

Certain examples are described below with reference to various chemical formulae. The chemical formulae referred to herein can exhibit the phenomena of tautomerism, conformational isomerism, stereo isomerism or geometric isomerism. As the formulae drawings within this specification can represent only one of the possible tautomeric, conformational isomeric, enantiomeric or geometric isomeric forms, it should be understood that the invention encompasses any tautomeric, conformational isomeric, enantiomeric or geometric isomeric forms which exhibit biological or pharmacological activity as described herein.

The compounds and compositions provided below are effective to inhibit translation (e.g., translation initiation) at least to the extent necessary for effective treatment of one or more cellular proliferative disorders and other disorders described herein. According to embodiments of the present invention, compounds of the present invention inhibit the protein-protein interaction between the eukaryotic translation initiation factors eIF4E and eIF4G, a translation initiation event commonly understood to be necessary for the proliferation of all cancer cells. According to aspects of the present invention, inhibition of translation initiation inhibits cell proliferation. According to embodiments of the present invention, cell proliferation is common to all forms of cancers and a method treating all forms of cancer is provided by inhibition of cellular proliferation.

While in certain examples translation may be substantially inhibited such that little or no activity results, in other examples the inhibition is at least sufficient to relieve and or alleviate the symptoms from a selected disorder to be treated.

In accordance with certain embodiments, compounds of the invention are represented by the generic formula set forth below.

Certain compounds of the present invention are of the type set forth in Formula I It is to be understood that substituents or moieties identified herein with respect to the structures presented throughout the specification may be bonded to atoms in a manner understood by those of skill in the art and that one or more moieties may include one or more acceptable bonding sites if not expressly indicated.

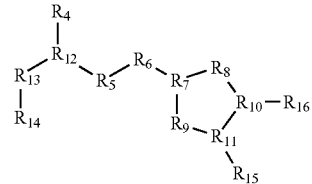

I

The ring structure including atoms $R_7$, $R_8$, $R_9$, $R_{10}$ and $R_{11}$ is aromatic or nonaromatic, saturated or unsaturated. Atoms $R_7$, $R_8$, $R_9$, $R_{10}$ and $R_{11}$ have a corresponding number of hydrogen atoms bonded thereto depending upon the bond state of the atom. Atom $R_7$ is C or N. Atom $R_8$ is C, N, O, or S. Atom $R_9$ is C, N, O, or S. Atom $R_{10}$ is C or N. Atom $R_{11}$ is C.

$R_6$ is NH, O, S, C or carbonyl.

$R_5$ is N, NH, O, S, C or carbonyl.

$R_{12}$ is C. The bond between $R_5$ and $R_{12}$ may be a single or double bond.

$R_4$ is hydrogen, hydroxyl or lower hydroxyalkyl, carboxyl, a lower alkyl ester, e.g.,

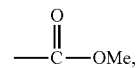

or oxygen (in which case the bond between $R_4$ and $R_{12}$ is a double bond, i.e., forming a carbonyl group); tetrazole, $SO_3H$, or $PO_3H_2$.

$R_{13}$ is CH, $CH_2$, N, or NH.

$R_{14}$ is homocyclic or heterocyclic (such as nitrogen substituted for carbon) including phenyl and substituted with one or more of $R_2$, where $R_2$ is hydrogen, halogen (halo), hydroxyl, CN, $CF_3$, $CO_2H$, $SO_3H$, $PO_3H_2$, $SO_2R$, $SO_2NHR$, $SONH_2$, $CONH_2$, CONHR and NHCOR, or a nitro group present in one, two, or three locations on the ring to which it is attached; where R is an alkyl of 1-4 carbons or aryl. In addition, the phenyl may optionally be bonded to $R_5$ directly to form a five membered ring or through a methylene group to form a six membered ring. Also, the phenyl optionally may be directly bonded to $R_6$ forming a six membered ring. The five or six membered ring can be homocyclic or heterocyclic, saturated or unsaturated, aromatic or nonaromatic.

$R_{13}$ can be bonded to $R_6$ through a methylene to create a five membered ring or an ethylene to create a six membered ring. The five or six membered ring can be homocyclic or heterocyclic, saturated or unsaturated, aromatic or nonaromatic.

$R_{15}$ is homocyclic or heterocyclic (such as nitrogen substituted for carbon) including phenyl and substituted with one or more of $R_3$, where $R_3$ is a group individually present in one, two, or three locations on the ring, wherein the group may be hydrogen, halo, OH, CN, $CF_3$, $CO_2H$, $SO_3H$, $PO_3H_2$, OR, $SO_2R$, $SO_2NHR$, $SONH_2$, —N=NR, $CONH_2$, CONHR and NHCOR, hydrogen, alkyl, cycloalkyl, heteroalkyl, phenyl or substituted phenyl, substituted or unsubstituted such as

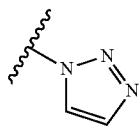

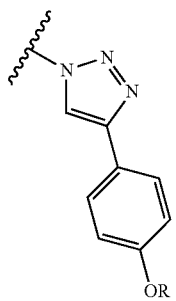, 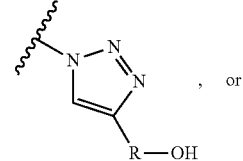

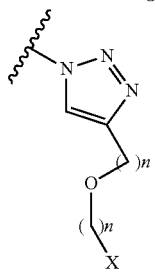

where n is 1-4 and X is $NH_2$, $N(CH_3)_2$ or $NHC(NH)NH_2$, substituted or unsubstituted conjugated or unconjugated aryl or heteroaryl, alicyclic, heterocyclic or polycyclic group, or $R_3$ forms a conjugated ring structure, e.g., a naphthalene, benzodioxine or benzodioxepine ring; where R is substituted or unsubstituted lower alkyl, e.g., C1-C4, or aryl. In addition X may also include

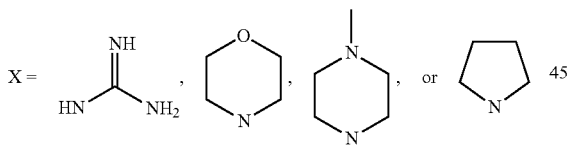

$R_{16}$ is $R_{15}$ or hydrogen. $R_{16}$ and $R_{15}$ can be the same or different. $R_{16}$ and $R_{15}$ can be C1-C3 alkyl, substituted with one or more of $R_3$ or unsubstituted, saturated or unsaturated, and can be covalently bonded together to form a five or six membered ring, substituted with one or more of $R_3$ or unsubstituted, aromatic or nonaromatic, saturated or unsaturated.

It is to be understood that compounds within the scope of the present disclosure include any and all subgeneric structures and species structures within the scope of formula I and other formula presented herein. One of skill in the art would readily understand that various combinations of substituents can be selected from those set forth above and presented elsewhere in this disclosure and as provided on separate scaffolds to describe specific compounds within the scope of the present disclosure without setting forth each and every species included within generic or subgeneric structures.

For example, compounds within the scope of this disclosure include those shown below where $R_X$ is $R_3$ and $R_Y$ is $R_2$:

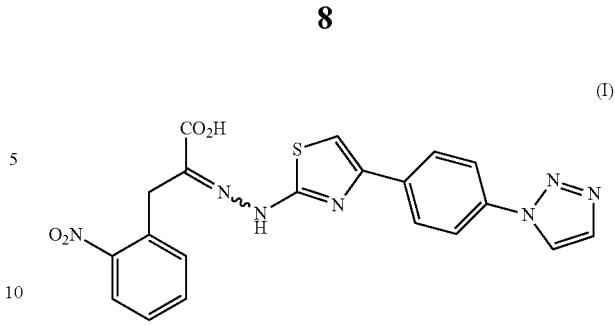
(I)

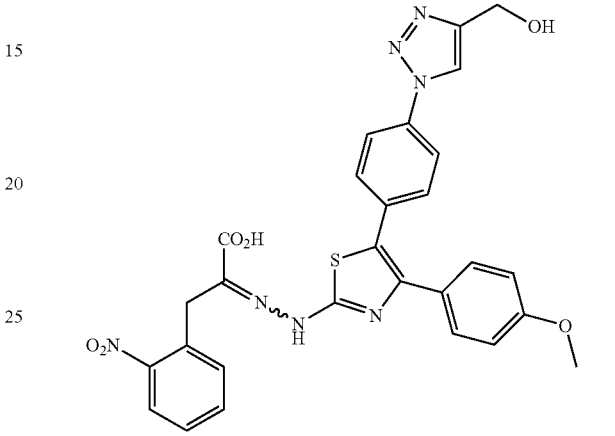
(II)

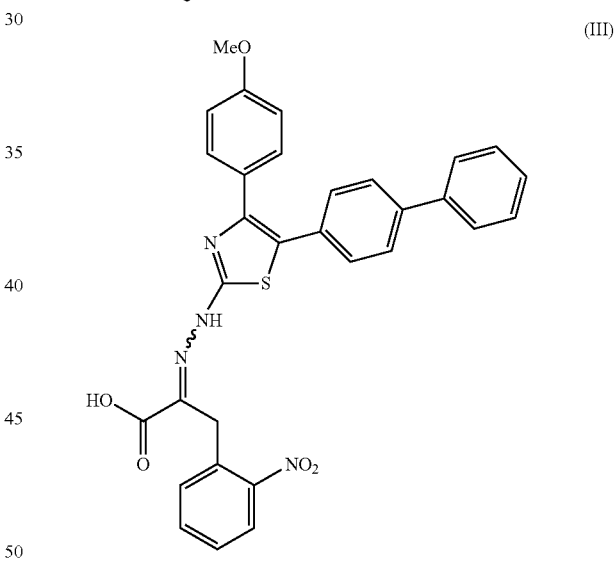
(III)

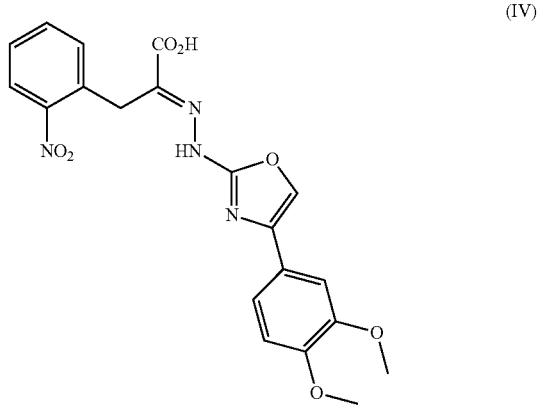
(IV)

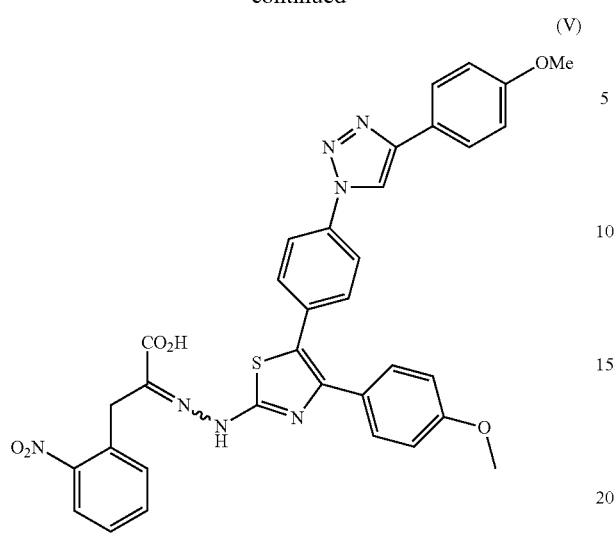
(V)
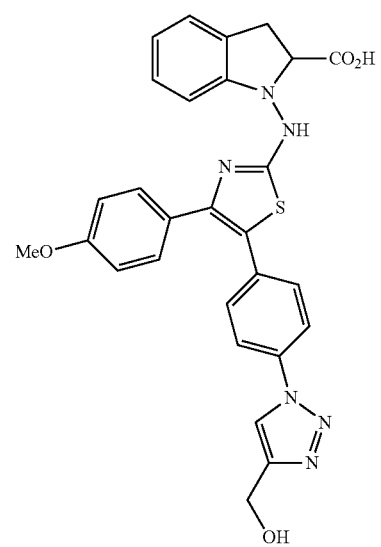
(VI)
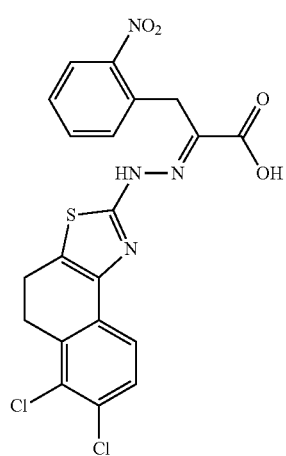
(VII)
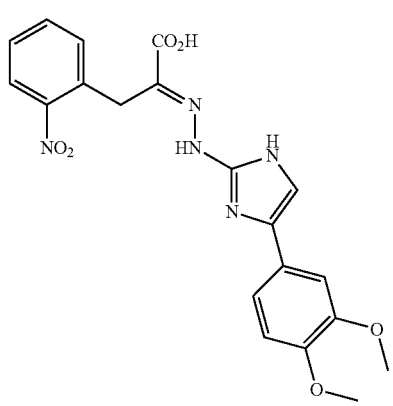
(VIII)
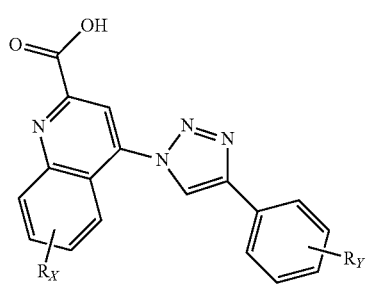
(IX)
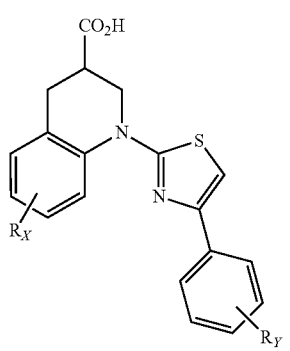
(X)
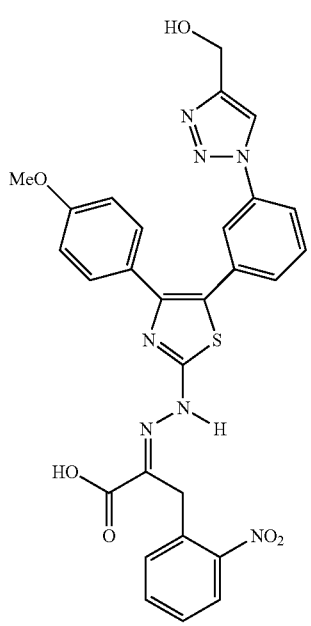
(XI)

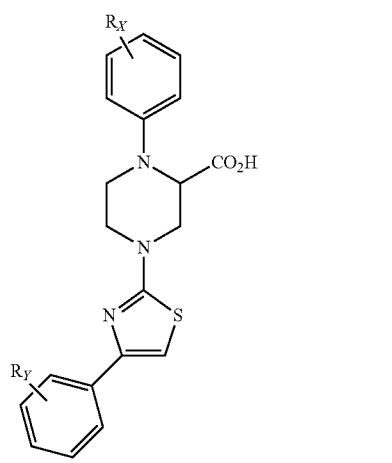

(XII)

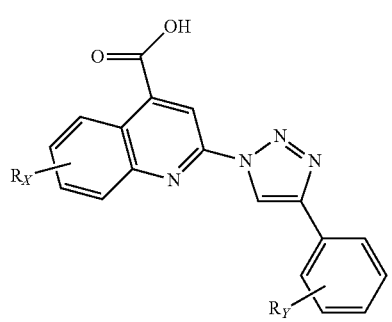

(XIII)

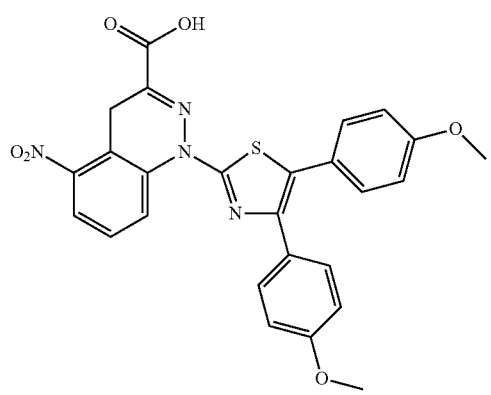

(XIV)

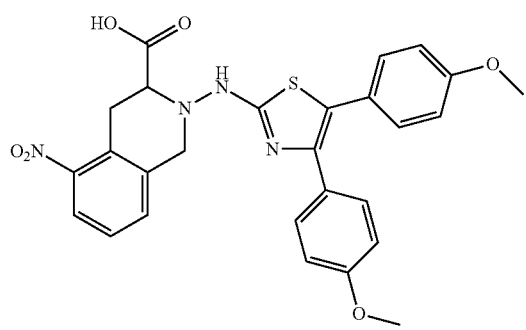

(XV)

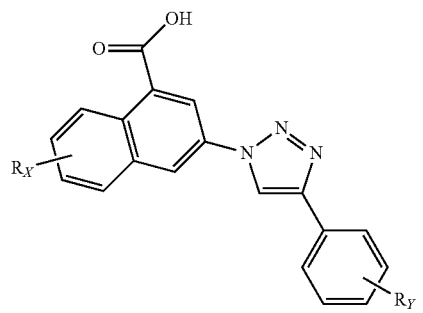

(XVI)

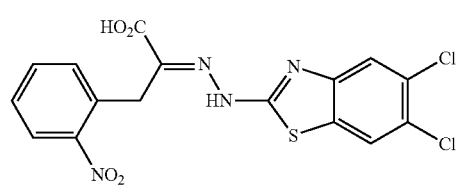

(XVII)

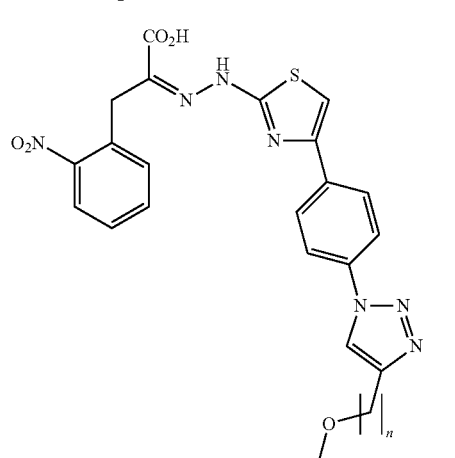

(XVIII)

wherein n=1-4 and R=NH$_2$, NMe$_2$, or

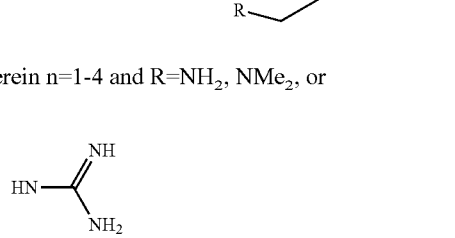

Alkyl, alkenyl and alkynyl include linear, branched, and cyclic structures and combinations thereof. "Alkyl" includes lower alkyl and extends to cover carbon fragments having up to 20 carbon atoms. Examples of alkyl groups include octyl, nonyl, norbornyl, undecyl, dodecyl, tridecyl, tetradecyl, pentadecyl, eicosyl and the like.

"Lower alkyl" means alkyl groups of from 1 to 7 carbon atoms. Examples of lower alkenyl groups include methyl, ethyl, propyl, isopropyl, butyl, isobutyl, sec-butyl, tert-butyl, pentyl, hexyl, heptyl, cyclopropyl, cyclobutyl, cyclopentyl, cyclohexyl, cycloheptyl and the like.

"Lower alkenyl" means alkenyl groups of 2 to 7 carbon atoms. Examples of lower alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, and the like.

"Lower alkynyl" means alkynyl groups of 2 to 7 carbon atoms. Examples of lower alkynyl groups include ethynyl, propargyl, 3-methyl-1-pentenyl, 2-heptynyl, and the like.

Alternatively, alkenyl and alkynyl groups can be referred to as unsaturated alkyl groups.

"Heteroalkyl" means an alkyl or cycloalkyl including one or more of oxygen, nitrogen or sulfur atoms replace carbon atoms in the alkyl or cycloalkyl group.

"Halogen" means fluorine, chlorine, bromine and iodine.

"Substituted" means one or more hydrogens on an alkyl, alkenyl or alkynyl group are replaced by one or more different atoms or groups of atoms. For example, hydrogen may be substituted by hydroxy.

As used herein, the term "aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, or indolizine. Those aryl groups having heteroatoms in the ring structure may also be referred to as "aryl heterocycles," "heterocycles," "heteroaryls," or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including, for example, alkylamino, dialkylamino, arylamino, diarylamino, and alkylarylamino), acylamino (including, for example, alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, and methylenedioxyphenyl).

The terms "heterocyclyl" or "heterocyclic group" include closed ring structures, e.g., 3- to 10-, or 4- to 7-membered rings, which include one or more heteroatoms. Heterocyclyl groups can be saturated or unsaturated and include pyrrolidine, oxolane, thiolane, piperidine, piperazine, morpholine, lactones, lactams such as azetidinones and pyrrolidinones, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety.

The term "ether" includes compounds or moieties, which contain oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties, which contain a carbon or a heteroatom bound to an oxygen atom, which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "hydroxy" or "hydroxyl" includes groups with an —OH or —O$^-$.

The term "carboxyl" or "carboxy" includes groups with an —CO$_2$H or —CO$_2^-$.

The term "halogen" includes fluorine, bromine, chlorine, iodine, etc. The term "perhalogenated" generally refers to a moiety wherein all hydrogens are replaced by halogen atoms.

"Heteroatom" includes atoms of any element other than carbon or hydrogen. Examples of heteroatoms include nitrogen, oxygen, sulfur and phosphorus.

The structure of some of the compounds of the invention includes asymmetric carbon atoms. It is to be understood accordingly that the isomers arising from such asymmetry (e.g., all enantiomers and diastereomers) are included within the scope of the invention, unless indicated otherwise. Such isomers are obtained in substantially pure form by classical separation techniques and by stereochemically controlled synthesis. Furthermore, the structures and other compounds and moieties discussed in this application also include all tautomers thereof. Alkenes and imines can include either the E- or Z-geometry, where appropriate.

Embodiments of the present invention include salts of the compounds of Formula I and those otherwise described herein and are likewise referred to as compounds of the present disclosure. Solutions of active compounds as free base or pharmacologically acceptable salts are prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Examples of acceptable salts include, but are not limited to, mineral or organic acid salts of basic residues such as amines; alkali or organic salts of basic residues such as carboxylic acids; and the like. The acceptable salts include the conventional non-toxic salts or the quaternary ammonium salts from non-toxic inorganic acids. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

For example, such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, mandelic, tartaric, citric, ascorbic, palmoic, maleic, hydroxymaleic, phenylacetic, glutamine, benzoic, salicylic, sulfanilic, 2-acetoxybenzoic, fumaric, toluenesulfonic, methanesulfonic, ethane disulfonic, oxalic, isethionic, and the like. Specifically, the acceptable salts can include those salts that naturally occur in vivo in a mammal. According to certain embodiments, preferred salts include chloride, bromide, iodide and fluoride.

An "anionic group," as used herein, refers to a group that is negatively charged at physiological pH. Preferred anionic groups include carboxylate, sulfate, sulfonate, sulfinate, sulfamate, tetrazolyl, phosphate, phosphonate, phosphinate, or phosphorothioate or functional equivalents thereof "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. *The Organic Chemistry of Drug Design and Drug Action*, Academic Press, Inc. San Diego, Calif., 1992, pp. 19-23). A particularly preferred anionic group is a carboxylate.

Further compounds within the scope of the present disclosure include the following using the R groups and X groups described above and with respect to Formula I and further including those described below:

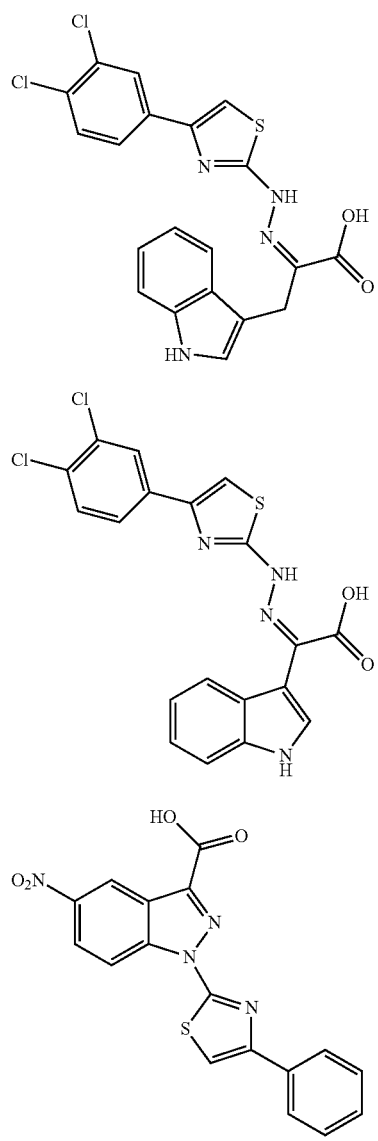

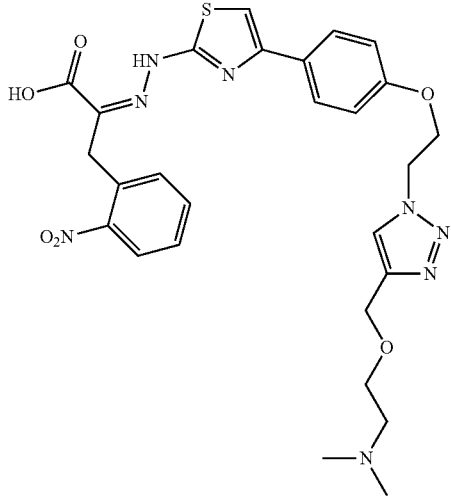

Further compounds within the scope of the present disclosure include the following using the R groups and X groups described above and with respect to Formula I and further including those described below wherein X=CH$_2$, O, S, SO, SO$_2$, NH, NHMe, or NMe$_2$, and n=0 or 1:

-continued
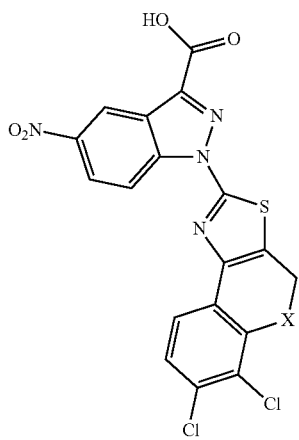
(XXV)
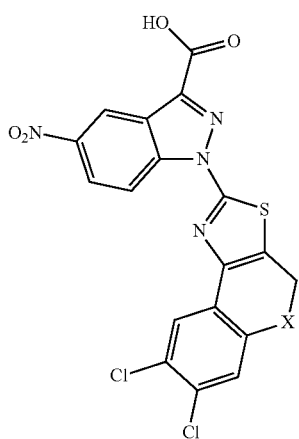
(XXVI)
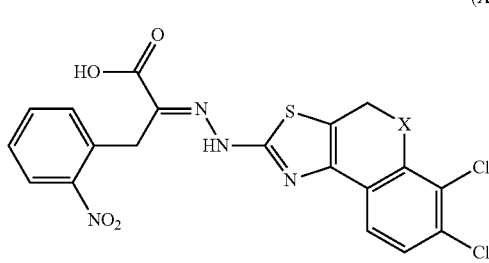
(XXVII)
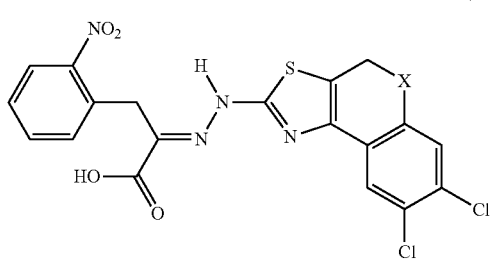
(XXVIII)
Further compounds within the scope of the present disclosure include the following using the R groups and X groups described above and with respect to Formula I and further including those described below wherein X=S, O, or N, X=CH$_2$, O, S, SO, SO$_2$, NH, NMe, or NR$_3$, Y=O or N, and n=0 or 1:
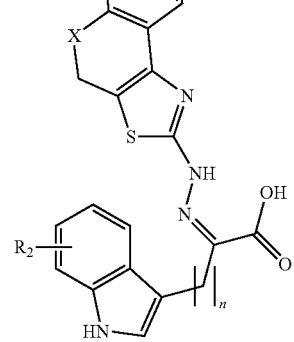
(XXIX)
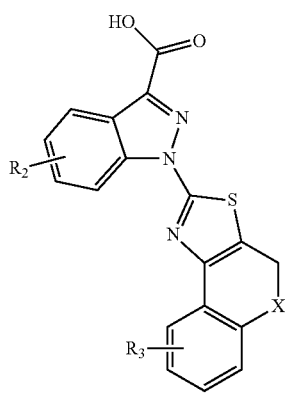
(XXX)
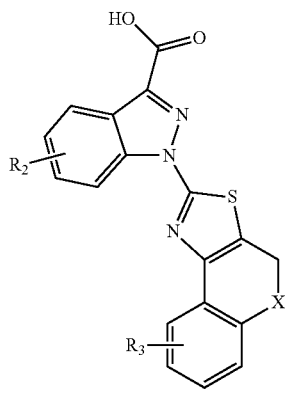
(XXXI)
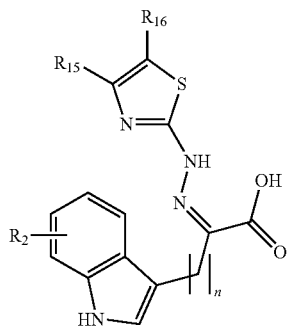
(XXXII)

19
-continued (XXXIII)

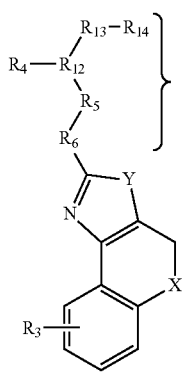

wherein $R_Q$ may be

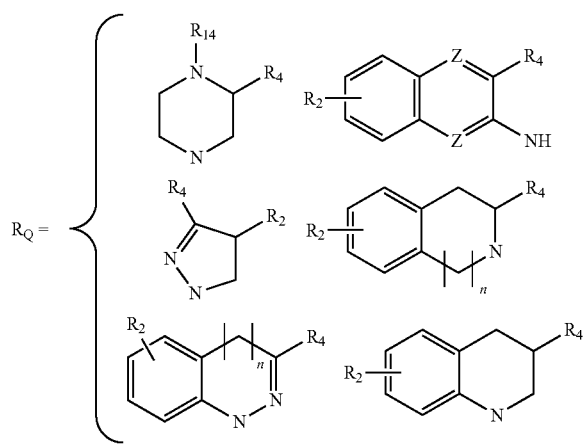

wherein Z=CH or N and n=0 or 1

Further compounds within the scope of the present disclosure include the following using the R groups and X groups described above and with respect to Formula I and further including those described below:

(XXXIV)

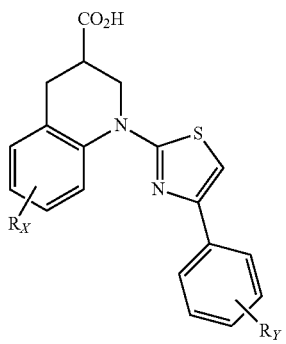

20

An exemplary embodiment is represented by (XXXV)

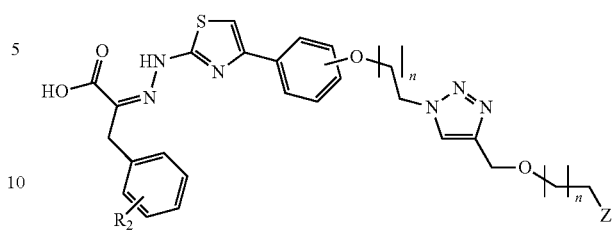

wherein n=1-3 and Z=NH$_2$, NHMe, NMe$_2$, or any of the following compounds

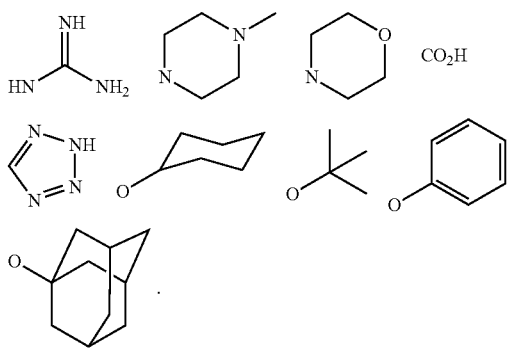

Further compounds within the scope of the present disclosure include the following using the R groups and X groups described above and with respect to Formula I and further including those described below wherein Rx=R$_2$ and Ry=R$_3$:

(XXXVI)

(XXXVII)

-continued

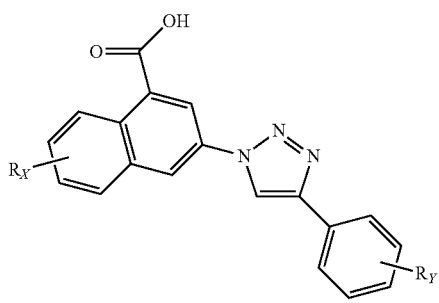
(XXXVIII)

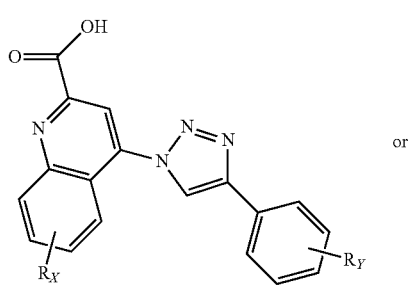
(XXXIX)

or

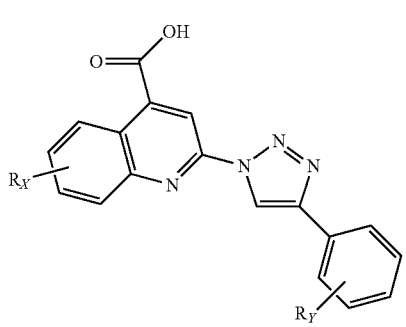
(XL)

wherein Rx=R$_2$, Ry and Ry=R$_3$, —O—(CH$_2$)n-O—(CH$_2$)$_2$—Z (n=2-4), NH$_2$, NHMe, NMe$_2$, or any of the following compounds

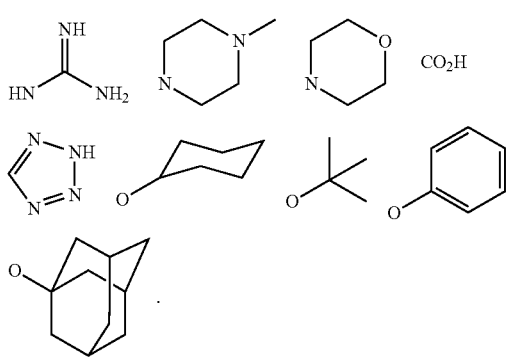

Further compounds within the scope of the present disclosure include the following using the R groups and X groups described above and with respect to Formula I and further including those described below:

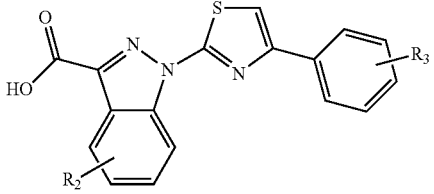
(XLI)

with an exemplary embodiment represented by

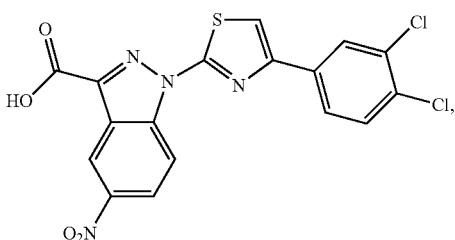
(XLII)

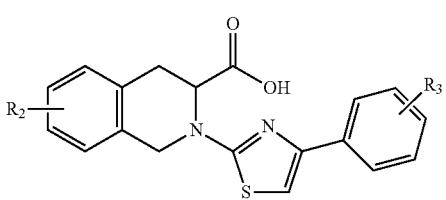
(XLII)

with an exemplary embodiment represented by

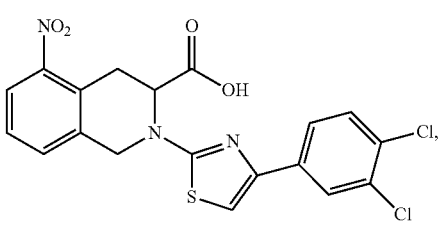
(XLIV)

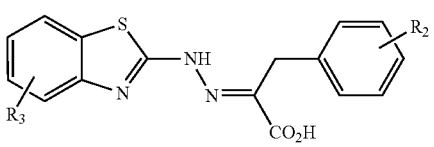
(XLV)

with an exemplary embodiment represented by

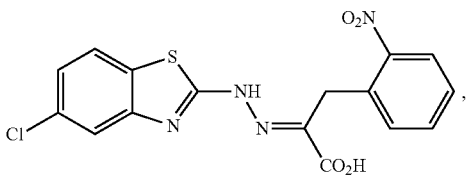
(XLVI)

(XLVII)

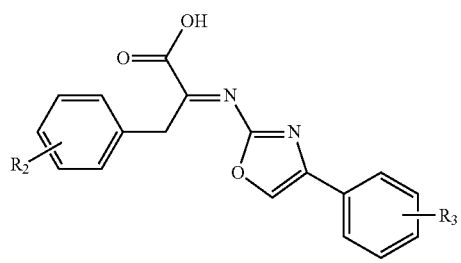

with an exemplary embodiment represented by (XLVIII)

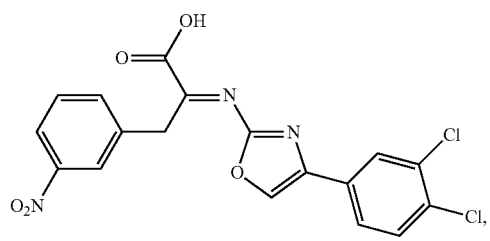

(XLIX)

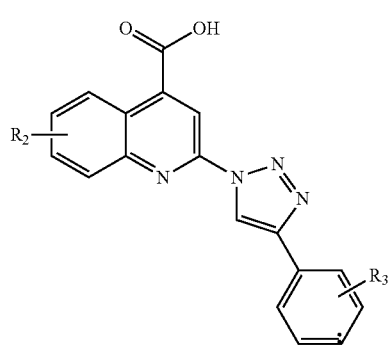

with an exemplary embodiment represented by (L)

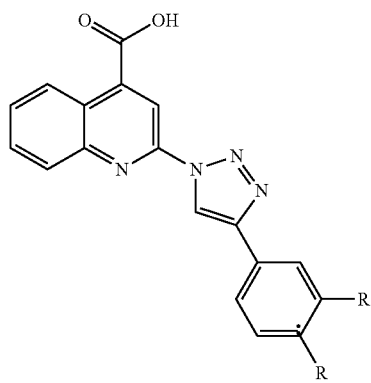

wherein R=H, Cl, (LI)

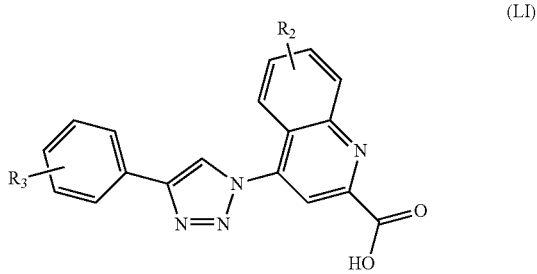

with an exemplary embodiment represented by (LII)

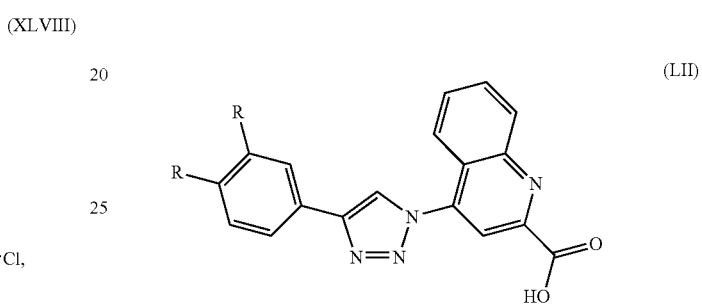

wherein R=H, Cl, (LIII)

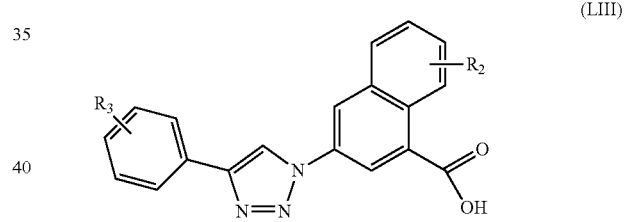

with an exemplary embodiment represented by (LIV)

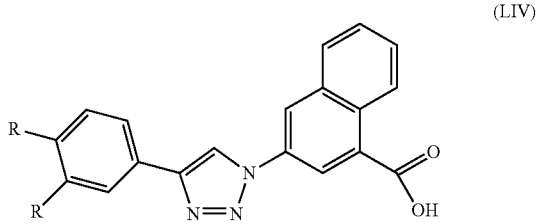

wherein R=H, Cl.

Further compounds within the scope of the present disclosure include the following using the R groups, X groups and Z groups described above and with respect to Formula I and further including those described below:

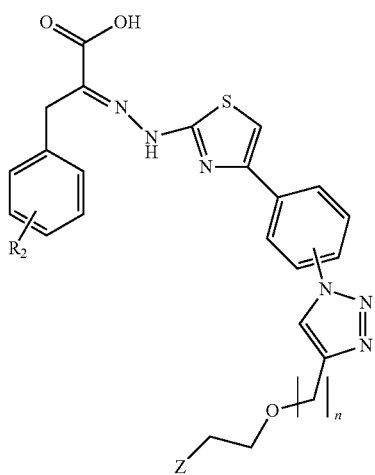

(LV)

wherein Z=NH$_2$, NHMe, NMe$_2$, or any of the following compounds

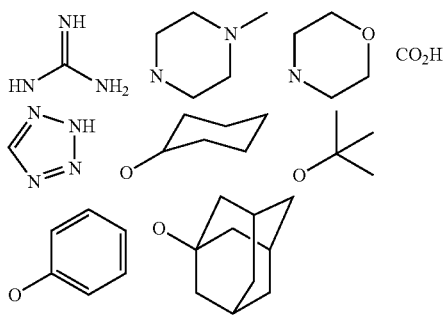

with an exemplary embodiment represented by

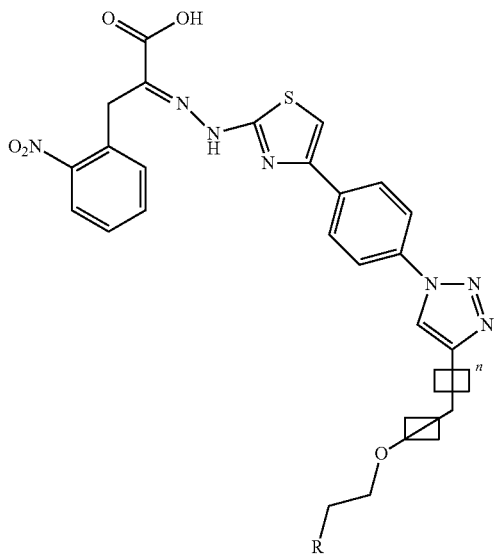

(LVI)

wherein R=NH$_2$, NMe$_2$, or H$_2$N=N—NH, and n=1-4.

Further compounds within the scope of the present disclosure include the following using the R groups, X groups and Z groups described above and with respect to Formula I and further including those described below:

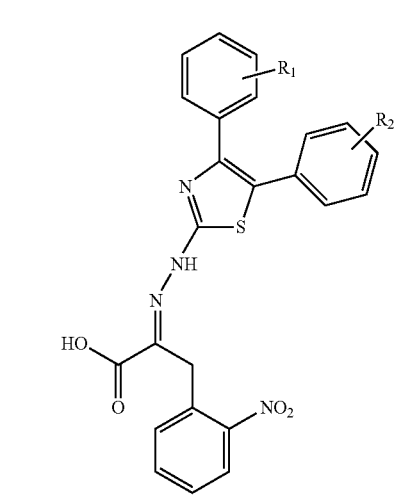

(LVII)

with an exemplary embodiment represented by

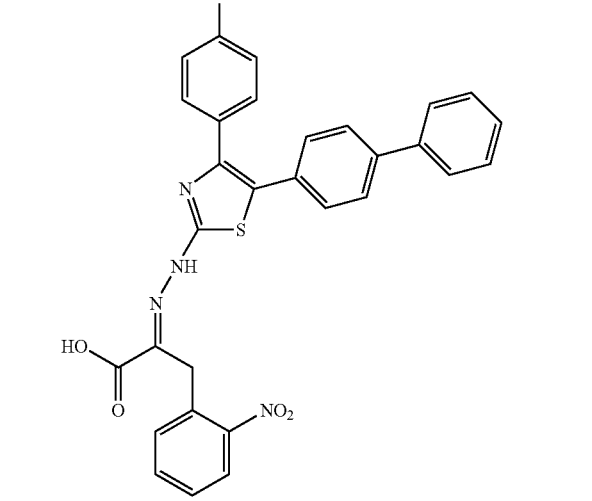

(LVIII)

and further embodiments set forth in the following table

| # | 4-R$_1$ | 5-R$_2$ |
|---|---------|---------|
| KY-577 | p-Φ | p-OMe |
| KY-612 | p-C$_6$H$_{11}$ | p-OMe |
| KY-632 | p-OMe | p-4-OH-C$_6$H$_4$ |
| KY-600 | 3,4-diCl | p-OMe |
| KY-599 | p-iPrO | p-OMe |
| KY-576 | p-EtO | p-OMe |
| KY-361 | p-3,4-diOMe | 3,4-diCl |
| KY-379 | p-OMe | p-N$_3$ |
| KY-369 | 3,4,5-triOMe | 3,4-diCl |
| KY-445 | p-OMe | p-Tz-4-p-MeO-C$_6$H$_4$ |
| KY-441 | p-OMe | p-Tz-4-3-OH-C$_6$H$_4$ |
| KY-443 | p-OMe | p-Tz-4-CH$_2$-OMe |
| KY-447 | p-OMe | p-Tz-4-(CH$_2$)$_3$-OH |

-continued

| # | 4-R$_1$ | 5-R$_2$ |
|---|---------|---------|
| KY-449 | p-OMe | p-Tz-4-NH$_2$ |
| KY-467 | p-OMe | m-Tz-4-CH$_2$-OH | wherein Tz=1,2,3-triazol-1-yl,

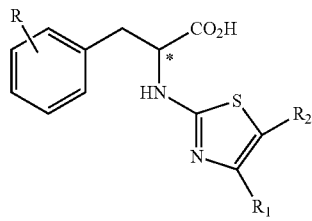
(LVIX)

with an exemplary embodiment represented by

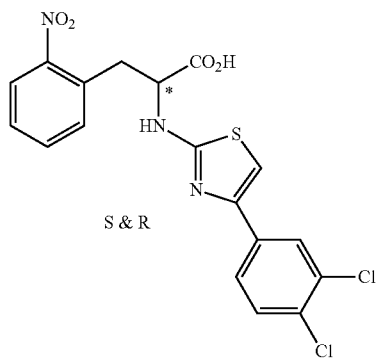
(LVX)

and with further embodiments set forth in the following table

| # | R | * | 4-R$_1$ | 5-R$_2$ |
|---|---|---|---------|---------|
| KY-549 | o-NO$_2$ | S | 3,4-diClC$_6$H$_3$ | H |
| KY-539 | H | S | 3,4-diClC$_6$H$_3$ | H |
| KY-609 | o-NO$_2$ | R | 3,4-diClC$_6$H$_3$ | H |
| KY-608 | p-CF$_3$ | S | 3,4-diClC$_6$H$_3$ | H |
| KY-654 | o-NO$_2$ | SR | p-OMe | p-MeOC$_6$H$_4$ |
| KY-635 | m-NO$_2$ | SR | 3,4-diClC$_6$H$_3$ | H, |

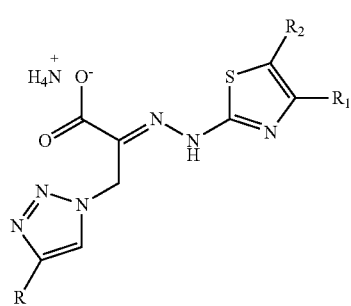
(LVXI)

with an exemplary embodiment represented by

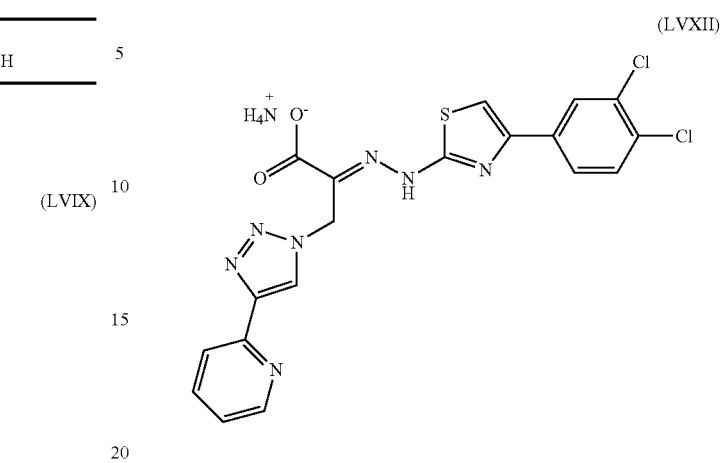
(LVXII)

and with further embodiments represented in the following table

| # | R | 4-R$_1$ | 5-R$_2$ |
|---|---|---------|---------|
| KY-758 | CH$_2$OH | 4-ClC$_6$H$_4$ | H |
| KY-766 | CH$_2$OMe | 3,4-diClC$_6$H$_3$ | H |
| KY-767 | 2-Py | 3,4-diClC$_6$H$_3$ | H, |

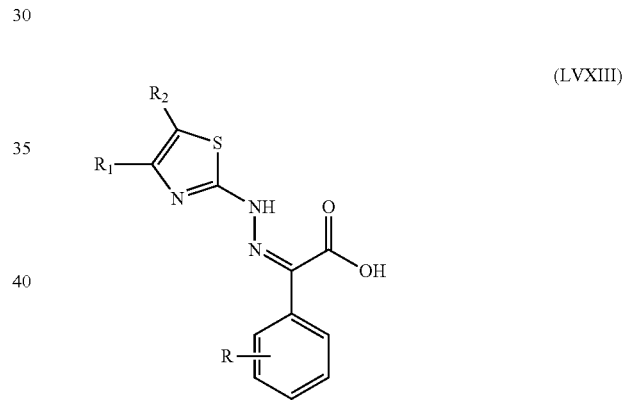
(LVXIII)

with an exemplary embodiment represented by (LVXIX)

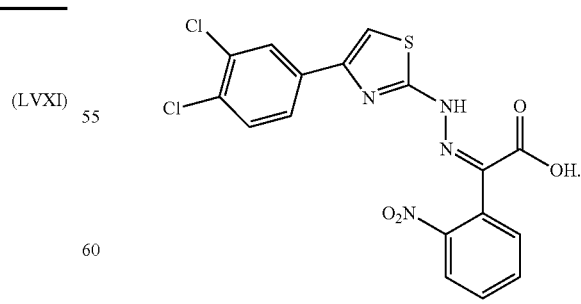
KY-782

Further compounds within the scope of the present disclosure include the following using the R groups, X groups and Z groups described above and with respect to Formula I and further including those described below:

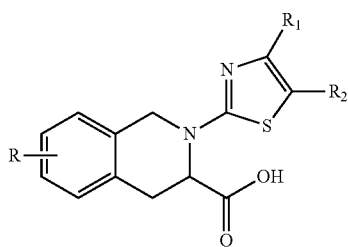

(LVXX)

with an exemplary embodiment represented by

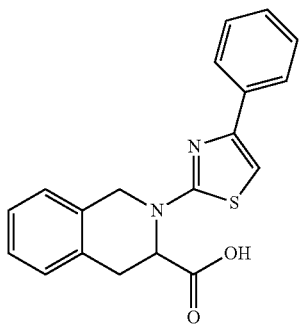

(LVXXI)

and with further embodiments set forth in the following table

| # | R | 4-$R_1$ | 5-$R_2$ |
|---|---|---|---|
| RYF-340 | H | $C_6H_5$ | H |
| RYF-331 | H | 3,4-diCl$C_6H_3$ | H |
| RYF-332 | H | p-MeO$C_6H_4$ | H, |

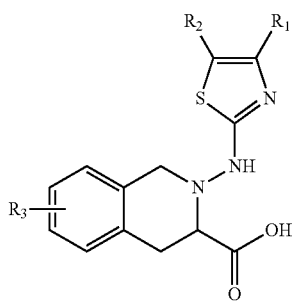

(LVXXII)

with an exemplary embodiment represented by

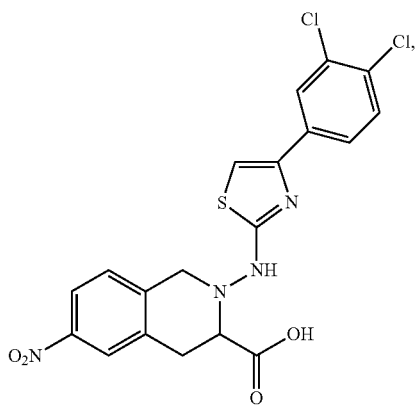

(LVXXIII)

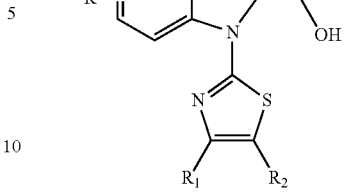

(LVXXIV)

with an exemplary embodiment represented by

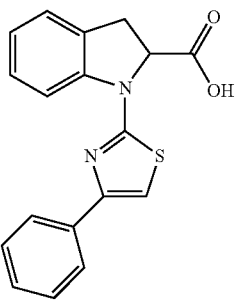

(LVXXV)

and with further embodiments represented in the following table

| # | R | 4-$R_1$ | 5-$R_2$ |
|---|---|---|---|
| RYF-504 | H | $C_6H_5$ | H |
| RYF-509 | H | 3,4-diCl$C_6H_3$ | H |

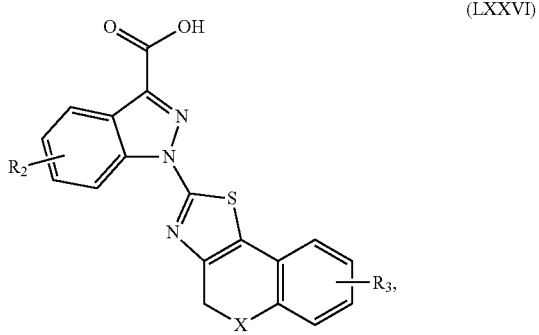

(LXXVI)

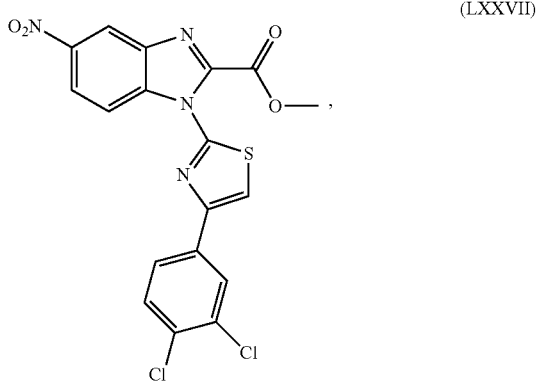

(LXXVII)

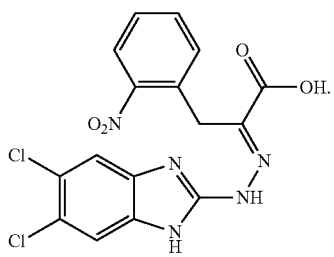
(LXXVIII)

Further compounds within the scope of the present disclosure include the following using the R groups, X groups and Z groups described above and with respect to Formula I and further including those described below:

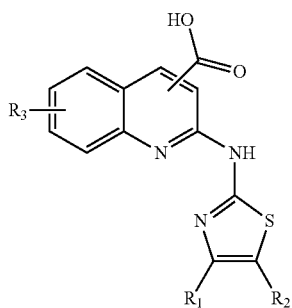
(LXXIX)

with exemplary embodiments represented by

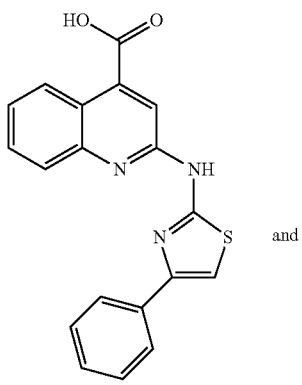
and
(LXXX)

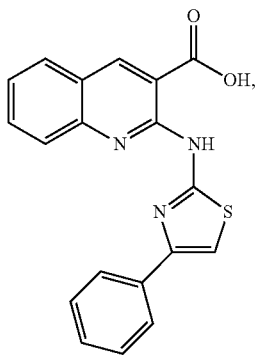
(LXXXI)

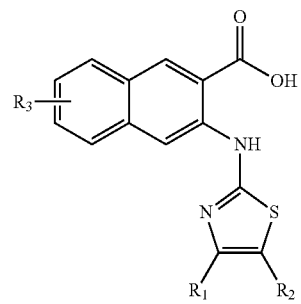
(LXXXII)

with an exemplary embodiment represented by

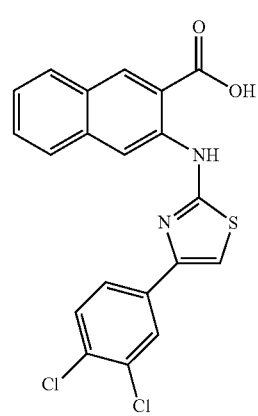
(LXXXIII)

and with further embodiments represented in the following table

| # | $R_3$ | 4-$R_1$ | 5-$R_2$ |
|---|---|---|---|
| KH-259 | H | 3,4-diClC$_6$H$_3$ | H |
| KH-260 | H | 4-ClC$_6$H$_4$ | H |
| KH-261 | H | 4-C$_6$H$_5$-C$_6$H$_4$ | H |
| KH-272 | H | 4-C$_6$H$_5$ | H, |

(LXXXIV)

with an exemplary embodiment represented by (LXXXV)

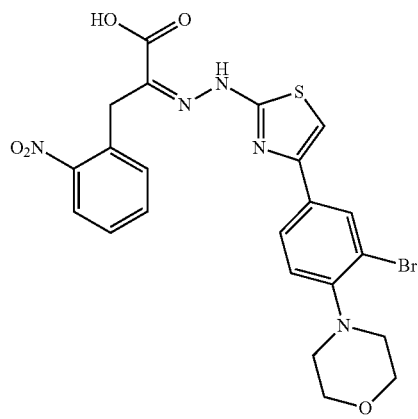

and with further embodiments represented in the following table

| # | $R_3$ | 4-$R_1$ | 5-$R_2$ |
|---|---|---|---|
| KH-290 | o-$NO_2$ | p-$HO_2C$-$C_6H_4$ | H |
| KH-260 | o-$NO_2$ | 3-Br-4-morpholinophenyl | H |
| KH-288 | o-$NO_2$ | 4-(2-morpholinoethoxy)phenyl | H |
| KH-289 | o-$NO_2$ | 4-(2-(4-methylpiperazin-1-yl)ethoxy)phenyl | H |

Certain additional embodiments of the present disclosure include the following using the R groups, X groups and Z groups described above and with respect to Formula I and further including those described below wherein X=CH2, O, S, SO, SO2, NH, NMe, or NMe2, Y=S, NH, NMe, or O, and n=1 or 2:

(LXXXVI)

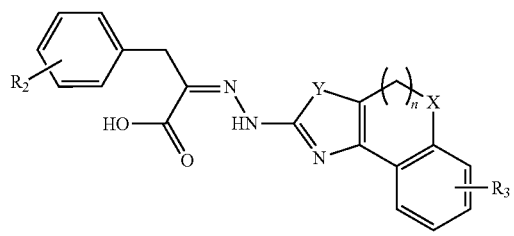

with an exemplary embodiment represented by (LXXXVII)

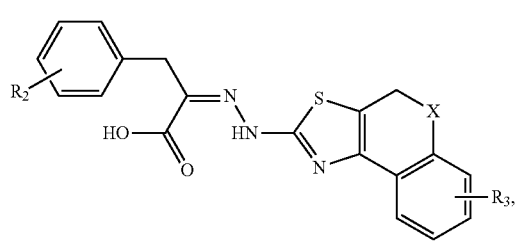

-continued (LXXXVIII)

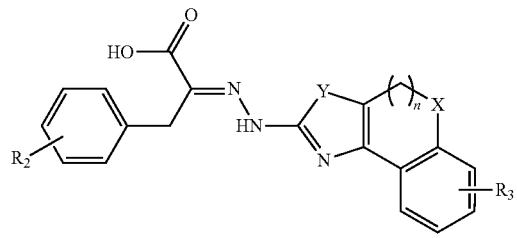

with an exemplary embodiment represented by (LXXXIX)

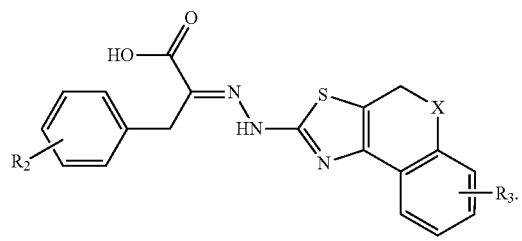

Certain additional embodiments of the present disclosure include the following using the R groups, X groups, Y groups, and Z groups and n described above and with respect to Formula I and further including those described below:

(XC)

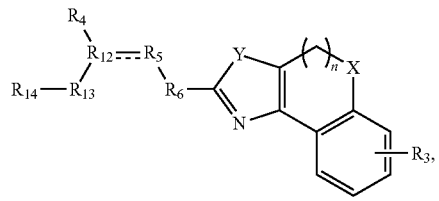

(XCI)

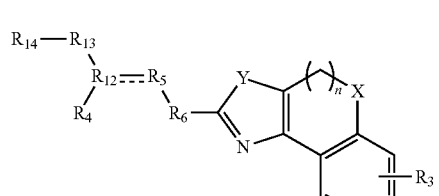

wherein $R_{14}$—$R_{13}$ may include

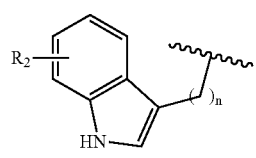

and
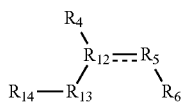
may include
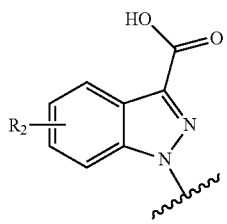
or
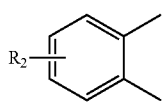
or
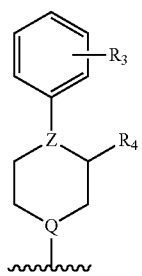
wherein Z=N or CH and Q=N, such as
(XCIII)
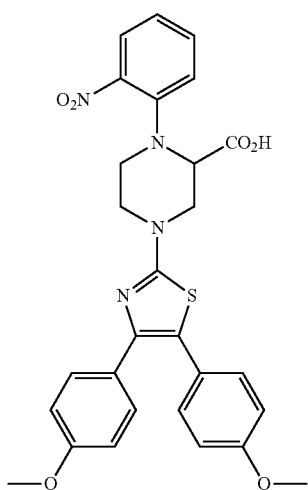
or
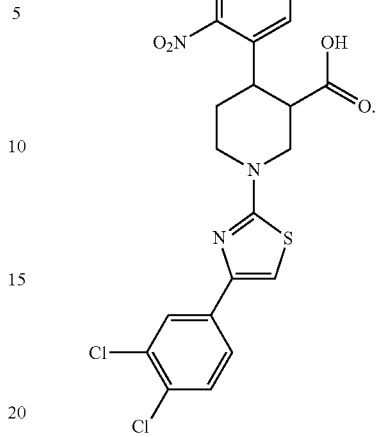
(XCIV)
Certain additional embodiments of the present disclosure include the following using the R groups, X groups, Q groups and Z groups described above and with respect to Formula I and further including those described below:
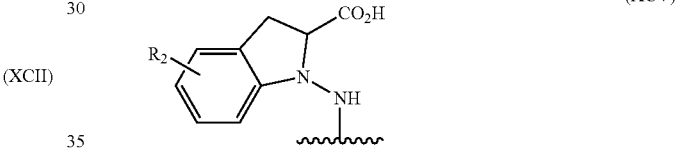
(XCV)
such as
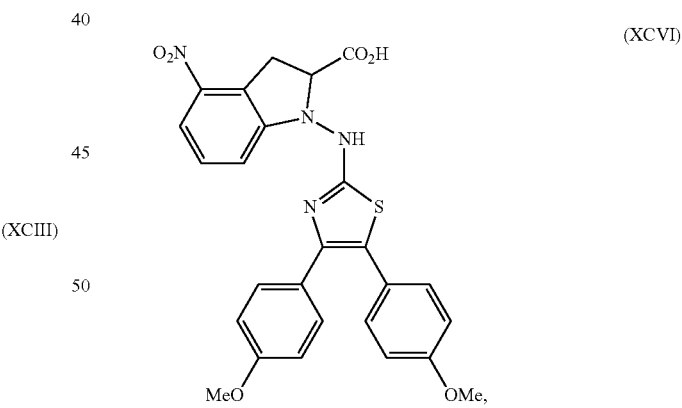
(XCVI)
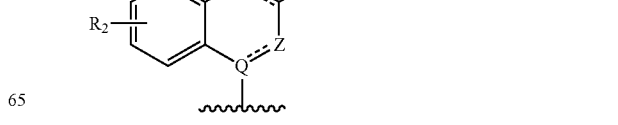
(XCVII)

wherein Z=N, CH, or CH₂, such as (XCVIII)

(XCIX)

(C)

(CI)

wherein Z=N, C, or CH₂, A=N or NH, and Q=CH₂ or N, such as (CII)

(CIII)

(CIV)

Certain additional embodiments of the present disclosure include the following using the R groups, X groups, Y groups and Z groups described above and with respect to Formula I and further including those described below wherein X=C, O, S, SO, SO₂, NMe, NMe₂, Y=S, O, or NH, and n=0 or 1:

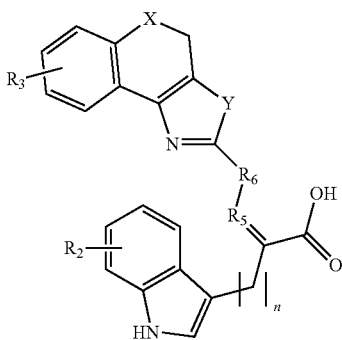

(CV)

with an exemplary embodiment represented by

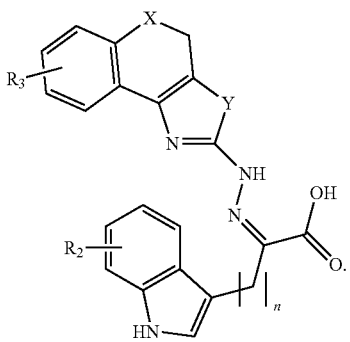

(CVI)

Additional compounds within the scope of the present disclosure include compound RYF-292 below and derivatives and analogs thereof including isomers and E and Z forms of compound RYF-292 and compounds that are structurally related to RYF-292 or mimic E and Z forms of RYS-292.

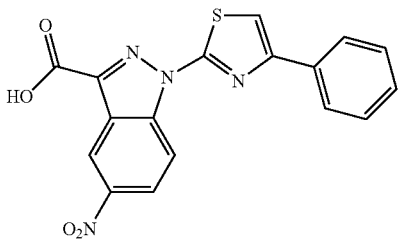 [SMILES: O=C(O)c1nn(-c2nc(-c3ccccc3)cs2)c2ccc([N+](=O)[O-])cc12]

Additional compounds within the scope of the present disclosure structurally related to RYF-292 are represented by the following formula including Z isomers thereof and compound mimics of the Z isomeric form:

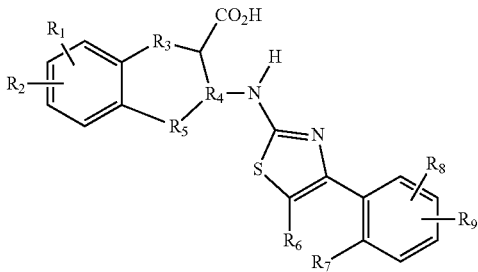

wherein $R_1$ is hydrogen, halogen, $NO_2$, $CO_2Y$, COQ, $CF_3$, $SO_2Z$, or $NHR_{10}$ Y is hydrogen, saturated or unsaturated or straight or branched or cyclic alkyl, saturated or unsaturated or straight or branched or cyclic heteroalkyl, aryl, or heteroaryl;

Q is hydrogen, saturated or unsaturated or straight or branched or cyclic alkyl, saturated or unsaturated or straight or branched or cyclic heteroalkyl, aryl, heteroaryl, or $NHR_{11}$;

Z is hydrogen, saturated or unsaturated or straight or branched or cyclic alkyl, saturated or unsaturated or straight or branched or cyclic heteroalkyl, aryl, or heteroaryl;

$R_{10}$ is hydrogen, saturated or unsaturated or straight or branched or cyclic alkyl, saturated or unsaturated or straight or branched or cyclic heteroalkyl, aryl, heteroaryl, amide, sulfonamide, urea or carbamate;

$R_{11}$ is hydrogen, saturated or unsaturated or straight or branched or cyclic alkyl, saturated or unsaturated or straight or branched or cyclic heteroalkyl, aryl, or heteroaryl;

$R_2$ is $R_1$, hydrogen, saturated or unsaturated or straight or branched or cyclic alkyl, saturated or unsaturated or straight or branched or cyclic heteroalkyl, aryl, or heteroaryl;

$R_3$ is $R_1$, $R_2$, hydrogen, CH, $CH_2$, or L;

L is NR';

R' is hydrogen, COR" or $SO_2R"$

R" is NHR'";

R'" is hydrogen, saturated or unsaturated or straight or branched or cyclic alkyl, saturated or unsaturated or straight or branched or cyclic heteroalkyl, aryl, or heteroaryl;

$R_4$ is $=N-$, $=C-$, $-CH-$, or N;

$R_5$ is $=N-$, or $(CH_2)_n$ wherein n=0, 1 or 2;

$R_6$ is hydrogen, $CH_3$, aryl, heteroaryl, $CH_2$-aryl, $CH_2$-heteroaryl, saturated or unsaturated or straight or branched or cyclic alkyl, or saturated or unsaturated or straight or branched or cyclic heteroalkyl;

$R_7$ is hydrogen, halogen, $CO_2Y$, COQ, $CF_3$, $SO_2Z$, or $NHR_{10}$;

$R_6$ and $R_7$ may optionally be bonded together in the structure above as $R_6-R_7$ forming a cyclic structure and $R_6-R_7$ is $CH_2$, O, S, or $NR_{11}$ forming a five membered ring, or $CH_2-CH_2$, $CH_2-O$, $CH_2-S$, $CH_2-SO$, $CH_2-SO_2$, $CH_2-NH$, or $CH_2-NR_{11}$ forming a six membered ring and wherein a heteroatom is not attached to or is unattached to a thiazolidine moiety;

$R_8$ is hydrogen, halogen, $NO_2$, $CO_2Y$, COQ, $CF_3$, $SO_2Z$, or $NHR_{10}$;

$R_9$ is hydrogen, halogen, $NO_2$, $CO_2Y$, COQ, $CF_3$, $SO_2Z$, or $NHR_{10}$.

The terms halogen, alkyl, heteroalkyl, aryl, heterocyclic (cyclic heteroalkyl) are as defined herein.

Exemplary embodiments within the scope of the above formula including compounds structurally related to RYF-292 including Z isomers thereof and compound mimics of the Z isomeric form include the following wherein X is $CH_2$, O, S, SO, $SO_2$, NH or $NR_{11}$:

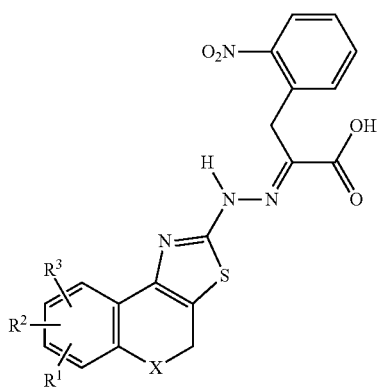
(CVII)
Z isomer
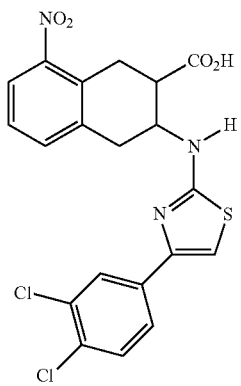
(CVIII)
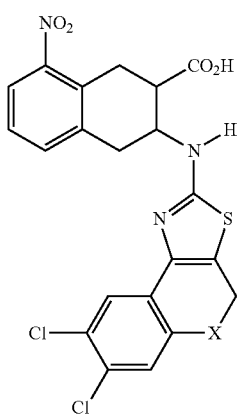
(CIX)
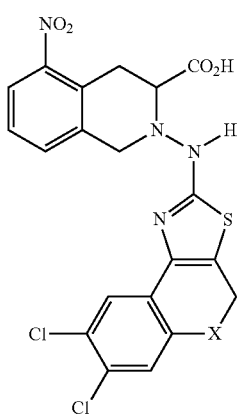
(CX)
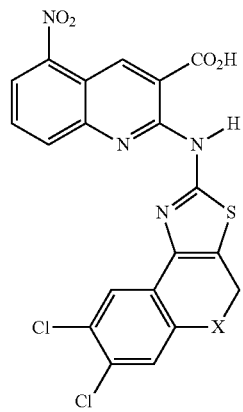
(CXI)
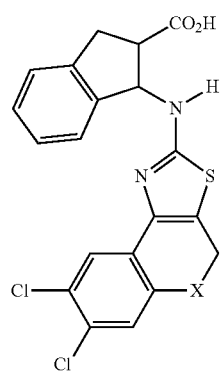
(CXII)
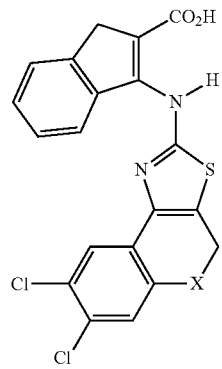
(CXIII)
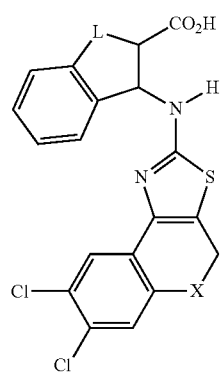
(CXIV)

(CXV)

(CXVI)

Additional compounds within the scope of the present disclosure structurally related to RYF-292 are represented by the following formula including E isomers thereof and compound mimics of the E isomeric form:

wherein $R_1$ is hydrogen, halogen, $NO_2$, $CO_2Y$, COQ, $CF_3$, $SO_2Z$, or $NHR_{10}$;

Y is hydrogen, saturated or unsaturated or straight or branched or cyclic alkyl, saturated or unsaturated or straight or branched or cyclic heteroalkyl, aryl, or heteroaryl;

Q is hydrogen, saturated or unsaturated or straight or branched or cyclic alkyl, saturated or unsaturated or straight or branched or cyclic heteroalkyl, aryl, heteroaryl or $NHR_{11}$;

Z is hydrogen, saturated or unsaturated or straight or branched or cyclic alkyl, saturated or unsaturated or straight or branched or cyclic heteroalkyl, aryl, or heteroaryl;

$R_{10}$ is hydrogen, saturated or unsaturated or straight or branched or cyclic alkyl, saturated or unsaturated or straight or branched or cyclic heteroalkyl, aryl, heteroaryl, amide, sulfonamide, urea or carbamate;

$R_{11}$ is hydrogen, saturated or unsaturated or straight or branched or cyclic alkyl, saturated or unsaturated or straight or branched or cyclic heteroalkyl, aryl, or heteroaryl;

$R_2$ is hydrogen, saturated or unsaturated or straight or branched or cyclic alkyl, saturated or unsaturated or straight or branched or cyclic heteroalkyl, aryl, or heteroaryl;

$R_3$ is $R_1$, $R_2$, hydrogen, CH, or $(CH_2)_n$ where n is 0 or 1;

$R_4$ is =N—, =CH—, or $CH_2$;

$R_5$ is $(CH_2)_n$ wherein n is 0 or 1;

$R_6$ is hydrogen, $CH_3$, aryl, heteroaryl, $CH_2$-aryl, $CH_2$-heteroaryl, saturated or unsaturated or straight or branched or cyclic alkyl, or saturated or unsaturated or straight or branched or cyclic heteroalkyl;

$R_7$ is hydrogen, halogen, $CO_2Y$, COQ, $CF_3$, $SO_2Z$, or $NHR_{10}$;

$R_6$ and $R_7$ may optionally be bonded together in the structure above as $R_6$—$R_7$ forming a cyclic structure and $R_6$-$R_7$ is $CH_2$, O, S, or $NR_{11}$ forming a five membered ring, or $CH_2$—$CH_2$, $CH_2$—O, $CH_2$—S, $CH_2$—SO, $CH_2$—$SO_2$, $CH_2$—NH, or $CH_2$—$NR_{11}$ forming a six membered ring and wherein a heteroatom is not attached to or is unattached to a thiazolidine moiety;

$R_8$ is hydrogen, halogen, $NO_2$, $CO_2Y$, COQ, $CF_3$, $SO_2Z$, or $NHR_{10}$;

$R_9$ is hydrogen, halogen, $NO_2$, $CO_2Y$, COQ, $CF_3$, $SO_2Z$, or $NHR_{10}$.

The terms halogen, alkyl, heteroalkyl, aryl, heterocyclic (cyclic heteroalkyl) are as defined herein.

Exemplary embodiments within the scope of the above formula including compounds structurally related to RYF-292 including E isomers thereof and compound mimics of the E isomeric form include the following wherein X is $CH_2$, O, S, SO, $SO_2$, NH or $NR_{11}$:

(CXVII)

(CXVIII)

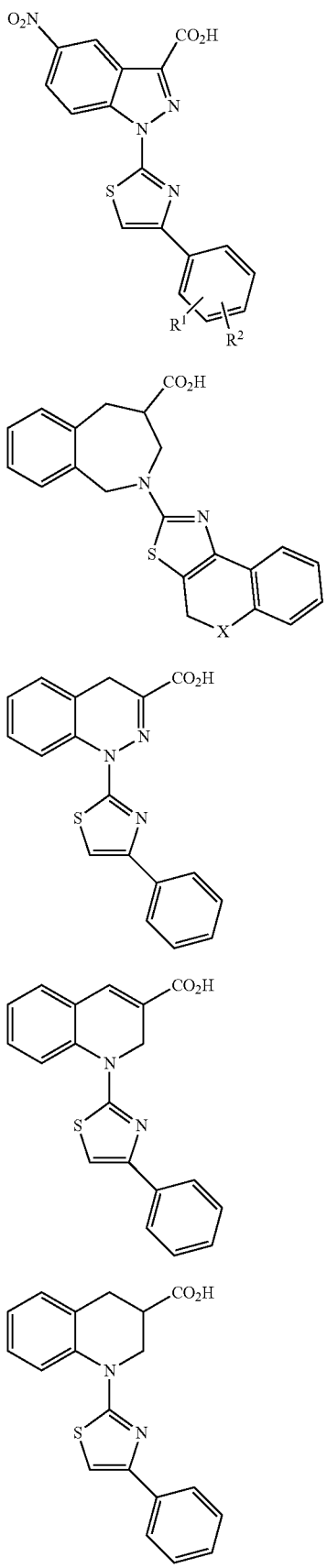
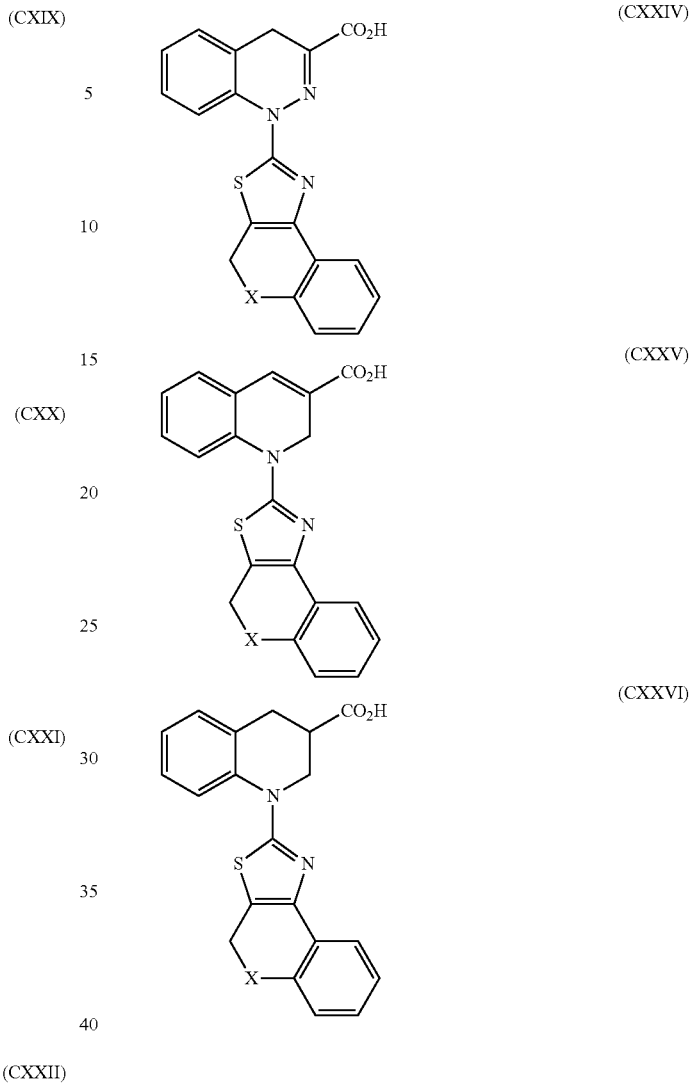

The present invention also features a method of inhibiting cap-dependent protein synthesis in a cell by contacting the cell with one or more of the compound described above. This inhibition in turn causes apoptosis, which results from the downregulation of growth-promoting proteins as well as the upregulation of apoptosis-promoting proteins and IRES-dependent proteins (e.g., Apaf-1, c-myc, XIAP, and DAP5). The compounds described herein bind a hydrophobic groove of eIF4E formed by the polypeptide segments 68-84 and 120-140 of human eIF4E (SEQ ID NO:1). The compounds inhibit the binding of eIF4G to eIF4E by blocking the eIF4G-binding site on eIF4E, displacing eIF4G from eIF4E by competitive binding or both. The different compounds investigated bind at slightly different but adjacent positions within the groove formed by segments 37-39, 68-84, and 120-140. 4EGI-1 (shown below) for example binds near residues L81, S82 and S83, whereas compound 6027288 (shown below) binds at an adjacent site near residues V69, F72, W73 and Y76. The adjacent binding sites also include H37, P38, L39, D127, L131, L135 and L138. These residues are in boldface in the sequence of human eIF4E below.

```
                                                         (SEQ ID NO: 1)
  1 MATVEPETTP TPNPPTTEEE KTESNQEVAN PEHYIKHPLQ NRWALWFFKN DKSKTWQANL

61 RLISKFDTVE DFWALYNHIQ LSSNLMPGCD YSLFKDGIEP MWEDEKNKRG GRWLITLNKQ

121 QRRSDLDRFW LETLLCLIGE SFDDYSDDVC GAVVNVRAKG DKIAIWTTEC ENREAVTHIG

181 RVYKERLGLP PKIVIGYQSH ADTATKSGST TKNRFVV
```

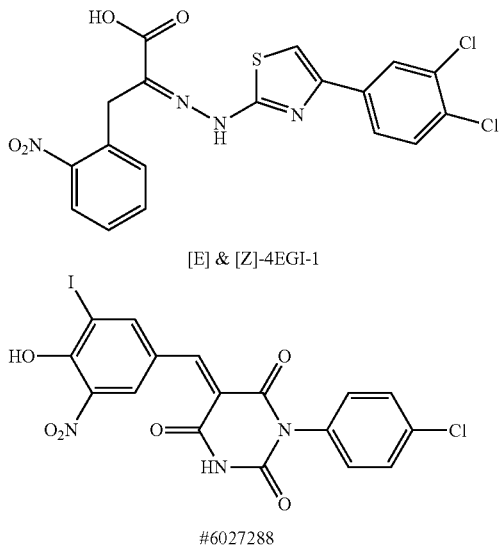

[E] & [Z]-4EGI-1

6027288

During apoptosis, 4E-BP1 undergoes caspase-dependent cleavage of its first 24 amino acids. The N-terminal segment that is eliminated contains a RAIP motif which is needed to start phosphorylation. Thus, the truncated form of 4E-BP 1 binds tightly to eIF4E but is not efficiently phosphorylated. The ectopic expression of eIF4E protects cells from apoptosis whereas the overexpression of 4E-BP 1 can induce apoptosis in transformed cells. Treatment of cultured cells with synthetic peptides containing the eIF4E-binding motif fused to a penetratin sequence has been shown to induce apoptosis.

By "adjacent to" is meant within 1, 2, 3, 4, or 5 positions upstream ($NH_2$) or downstream (COOH) of the reference amino acid in the reference sequences.

The compounds described herein are useful to inhibit protein synthesis thereby inhibiting proliferation of a cell such as a tumor cell or an abnormal cell (benign or malignant cell). An abnormal cell is a cell having an increased proliferation index, a decreased apoptotic index, or both relative to a normal non-cancerous cell. For example, the compounds, referred to as inhibitory compounds, preferentially or selectively inhibit tumor cell growth compared to normal cell growth. For example, protein synthesis and/or cell proliferation is inhibited at least 10%, 25%, 50%, 75%, 100%, and up to 5-fold, 10-fold and more in tumor cells compared to non-tumor cells. The method is carried out by administering to a patient in need thereof a pharmaceutical composition containing the inhibitory compound. According to one aspect, the patient or animal to be treated is identified as one that has a tumor cell containing an increased level of a cap-dependent translation initiation factor compared to the level in a normal non-tumor cell. For example, the patient is diagnosed as having a tumor or abnormal proliferating cells which is characterized by an increased amount of a cap-dependent translation factor compared to the level in a normal non-tumor cell. For example, the tumor cell contains an aberrantly high amount of eIF4E and/or eIF4G. Such tumor types include tumors of the lung, breast, skin, bone, head (neurological tissues such as brain and spinal cord), neck, bladder, colon, prostate, ovaries, uterus, cervix, larynx, gallbladder, pancreas, rectum, parathyroid, thyroid, adrenal gland, kidney, bronchi, liver, gastrointestinal tract, lymphomas, and neuroblastomas.

The compounds of the invention and the other pharmacologically active agent may be administered to a patient simultaneously, sequentially, or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms, which are taken simultaneously. The term "combination" further refers to the case where the compounds are provided in separate dosage forms and are administered sequentially.

"Combination therapy" (or "co-therapy") includes the administration of a compound of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, inhalation, oral routes, intravenous routes, intramuscular routes, subcutaneous, rectal, intraperitoneal, parenteral, transdermal, gastrointestinal, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, therapeutic agents may be administered orally or by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In at least certain examples, the compounds disclosed here can be used in the treatment of cellular proliferative disorders, such as cancer or non-cancer proliferative disorders. Treatment of cellular proliferative disorders is intended to include, but is not limited to, inhibition of proliferation including rapid proliferation. As used herein, the term "cellular proliferative disorder" includes, but is not limited to, disorders characterized by undesirable or inappropriate proliferation of one or more subset(s) of cells in a multicellular organism. The term "cancer" refers to various types of malignant neoplasms, most of which can invade surrounding tissues, and may metastasize to different sites (see, for example, PDR Medical Dictionary 1st edition (1995), incorporated herein by reference in its entirety for all purposes). The terms "neoplasm" and "tumor" refer to an abnormal tissue that grows by cellular proliferation more rapidly than normal and continues to grow after the stimuli that initiated proliferation is removed. Id. Such abnormal tissue shows partial or complete lack of structural organization and functional coordination with the normal tissue which may be either benign (i.e., benign tumor) or malignant (i.e., malignant tumor).

The language "treatment of cellular proliferative disorders" is intended to include, but is not limited to, the prevention of the growth of neoplasms in a subject or a reduction in the growth of pre-existing neoplasms in a subject. The inhibition also can be the inhibition of the metastasis of a neoplasm from one site to another. In certain embodiments, the neoplasms are sensitive to the compounds of the present invention. Examples of the types of neoplasms intended to be encompassed by the present invention include, but are not limited to, those neoplasms associated with cancers of the breast, skin, bone, prostate, ovaries, uterus, cervix, liver, lung, brain, larynx, gallbladder, pancreas, rectum, parathyroid, thyroid, adrenal gland, immune system, neural tissue, head and neck, colon, stomach, bronchi, and/or kidneys.

Examples of general categories of cancer include, but are not limited to, carcinomas (i.e., malignant tumors derived from epithelial cells such as, for example, common forms of breast, prostate, lung and colon cancer), sarcomas (i.e., malignant tumors derived from connective tissue or mesenchymal cells), lymphomas (i.e., malignancies derived from hematopoietic cells), leukemias (i.e., malignancies derived from hematopoietic cells), germ cell tumors (i.e., tumors derived from totipotent cells. In adults most often found in the testicle or ovary; in fetuses, babies and young children, most often found on the body midline, particularly at the tip of the tailbone), blastic tumors (i.e., a typically malignant tumor which resembles an immature or embryonic tissue) and the like.

Examples of specific neoplasms intended to be encompassed by the present invention include, but are not limited to, acute lymphoblastic leukemia; myeloid leukemia, acute myeloid leukemia, childhood; adrenocortical carcinoma; AIDS-related cancers; AIDS-related lymphoma; anal cancer; appendix cancer; astrocytoma (e.g., cerebellar, cerebral); atypical teratoid/rhabdoid tumor; basal cell carcinoma; bile duct cancer, extrahepatic; bladder cancer; bone cancer, osteosarcoma and malignant fibrous histiocytoma; brain tumor (e.g., brain stem glioma, central nervous system atypical teratoid/rhabdoid tumors, central nervous system embryonal tumors, cerebellar astrocytoma, cerebral astrocytoma/malignant glioma, craniopharyngioma, ependymoblastoma, ependymoma, medulloblastoma, medulloepithelioma, pineal parenchymal tumors of intermediate differentiation, supratentorial primitive neuroectodermal tumors and/or pineoblastoma, visual pathway and/or hypothalamic glioma, brain and spinal cord tumors); breast cancer; bronchial tumors; Burkitt lymphoma; carcinoid tumor (e.g., gastrointestinal); carcinoma of unknown primary; central nervous system (e.g., atypical teratoid/rhabdoid tumor, embryonal tumors (e.g., lymphoma, primary); cerebellar astrocytoma; cerebral astrocytoma/malignant glioma; cervical cancer; chordoma; chronic lymphocytic leukemia; chronic myelogenous leukemia; chronic myeloproliferative disorders; colon cancer; colorectal cancer; craniopharyngioma; cutaneous T-cell lymphoma; embryonal tumors, central nervous system; endometrial cancer; ependymoblastoma; ependymoma; esophageal cancer; Ewing family of tumors; extracranial germ cell tumor; extragonadal germ cell tumor; extrahepatic bile duct cancer; eye cancer (e.g., intraocular melanoma, retinoblastoma); gallbladder cancer; gastric cancer; gastrointestinal tumor (e.g., carcinoid tumor, stromal tumor (gist), stromal cell tumor); germ cell tumor (e.g., extracranial, extragonadal, ovarian); gestational trophoblastic tumor; glioma (e.g., brain stem, cerebral astrocytoma); hairy cell leukemia; head and neck cancer; hepatocellular cancer; Hodgkin lymphoma; hypopharyngeal cancer; hypothalamic and visual pathway glioma; intraocular melanoma; islet cell tumors; Kaposi sarcoma; kidney cancer; large cell tumors; laryngeal cancer (e.g., acute lymphoblastic, acute myeloid); leukemia (e.g., acute myeloid, chronic lymphocytic, chronic myelogenous, hairy cell); lip and/or oral cavity cancer; liver cancer; lung cancer (e.g., non-small cell, small cell); lymphoma (e.g., AIDS-related, Burkitt, cutaneous T-cell, Hodgkin, non-Hodgkin, primary central nervous system); macroglobulinemia, Waldenström; malignant fibrous histiocytoma of bone and/or osteosarcoma; medulloblastoma; medulloepithelioma; melanoma; merkel cell carcinoma; mesothelioma; metastatic squamous neck cancer; mouth cancer; multiple endocrine neoplasia syndrome; multiple myeloma/plasma cell neoplasm; mycosis fungoides; myelodysplastic syndromes; myelodysplastic/myeloproliferative diseases; myelogenous leukemia (e.g., chronic, acute, multiple); myeloproliferative disorders, chronic; nasal cavity and/or paranasal sinus cancer; nasopharyngeal cancer; neuroblastoma; non-Hodgkin lymphoma; non-small cell lung cancer; oral cancer; oral cavity cancer, oropharyngeal cancer; osteosarcoma and/or malignant fibrous histiocytoma of bone; ovarian cancer (e.g., ovarian epithelial cancer, ovarian germ cell tumor, ovarian low malignant potential tumor); pancreatic cancer (e.g., islet cell tumors); papillomatosis; paranasal sinus and/or nasal cavity cancer; parathyroid cancer; penile cancer; pharyngeal cancer; pheochromocytoma; pineal parenchymal tumors of intermediate differentiation; pineoblastoma and supratentorial primitive neuroectodermal tumors; pituitary tumor; plasma cell neoplasm/multiple myeloma; pleuropulmonary blastoma; primary central nervous system lymphoma; prostate cancer; rectal cancer; renal cell cancer; renal, pelvis and/or ureter, transitional cell cancer; respiratory tract carcinoma involving the nut gene on chromosome 15; retinoblastoma; rhabdomyosarcoma; salivary gland cancer; sarcoma (e.g., Ewing family of tumors, Kaposi, soft tissue, uterine); Sézary syndrome; skin cancer (e.g., non-melanoma, melanoma, merkel cell); small cell lung cancer; small intestine cancer; soft tissue sarcoma; squamous cell carcinoma; squamous neck cancer with occult primary, metastatic; stomach cancer; supratentorial primitive neuroectodermal tumors; T-cell lymphoma, cutaneous; testicular cancer; throat cancer; thymoma and/or thymic carcinoma; thyroid cancer; transitional cell cancer of the renal, pelvis and/or ureter; trophoblastic tumor; unknown primary site carcinoma; urethral cancer; uterine cancer, endometrial; uterine sarcoma; vaginal cancer; visual pathway and/or hypothalamic glioma; vulvar cancer; Waldenström macroglobulinemia; Wilms tumor and the like. For a review, see the National Cancer Institute's Worldwide Website (cancer.gov/cancer-topics/alphalist). One of skill in the art will understand that this list is exemplary only and is not exhaustive, as one of skill in the art will readily be able to identify additional cancers and/or neoplasms based on the disclosure herein.

Examples of noncancerous cellular proliferative disorders includes fibroadenoma, adenoma, intraductal papilloma, nipple adenoma, adenosis, fibrocystic disease or changes of breast, plasma cell proliferative disorder (PCPD), restenosis, atherosclerosis, rheumatoid arthritis, myofibromatosis, fibrous hamartoma, granular lymphocyte proliferative disorders, benign hyperplasia of prostate, heavy chain diseases (HCDs), lymphoproliferative disorders, psoriasis, idiopathic pulmonary fibrosis, sclroderma, cirrhosis of the liver, IgA nephropathy, mesangial proliferative glomerulonephritis, membranoproliferative glomerulonephritis, hemangiomas, vascular and non-vascular intraocular proliferative disorders and the like. One of skill in the art will understand that this list is exemplary only and is not exhaustive, as one of skill in the art will readily be able to identify additional noncancerous cellular proliferative disorders based on the disclosure herein.

In accordance with certain other examples, methods for treating viral infections are also disclosed. Treatment of viral infections is intended to include, but is not limited to, the use of a compound described herein to prevent the initiation of viral protein synthesis. The term "viral infection," as used herein, refers to one or more cells which have been infected with a virus, such as a DNA or RNA animal virus. As used herein, RNA viruses include, but are not limited to, virus families such as picornaviridae (e.g., polioviruses), reoviridae (e.g., rotaviruses), togaviridae (e.g., encephalitis viruses, yellow fever virus, rubella virus), orthomyxoviridae (e.g., influenza viruses), paramyxoviridae (e.g., respiratory syncytial virus, measles virus, mumps virus, parainfluenza virus), rhabdoviridae (e.g., rabies virus), coronaviridae, bunyaviridae, flaviviridae, filoviridae, arenaviridae, bunyaviridae, and retroviridae (e.g., human T-cell lymphotropic viruses (HTLV), human immunodeficiency viruses (HIV)). As used herein, DNA viruses include, but are not limited to, virus families such as papovaviridae (e.g., papilloma viruses), adenoviridae (e.g., adenovirus), herpesviridae (e.g., herpes simplex viruses), and poxyiridae (e.g., variola viruses). In certain embodiments, the viral infection is caused by hepatitis B virus, hepatitis C virus, and/or HIV. One of skill in the art will understand that this list is exemplary only and is not exhaustive, as one of skill in the art will readily be able to identify additional viral infections based on the disclosure herein.

In accordance with other examples, methods for treating disorders associated with viral infections are disclosed. Treatment of one or more disorders associated with viral infections is intended to include, but is not limited to, the use of a compound described herein to reduce or alleviate one or more symptoms of a viral infection. As used herein, the term "disorders associated with viral infection" refers to the host's response to infection by one or more viruses. Such responses include, but are not limited to neurological symptoms (e.g., encephalitis, meningoencephalitis, paralysis, myelopathy, neuropathy, aseptic meningitis, hemiparesis, dementia, dysphagia, lack of muscular coordination, impaired vision, coma, and the like), wasting symptoms (e.g., inflammatory cell infiltration, perivascular cuffing of blood vessels, demyelination, necrosis, reactive gliosis and the like), gastroenteritis symptoms (e.g., diarrhea, vomiting, cramps and the like), hepatitis symptoms (nausea, vomiting, right upper quadrant pain, raised liver enzyme levels (e.g., AST, ALT and the like), jaundice and the like), hemorrhagic fever symptoms (e.g., headache, fever, chills body pains, diarrhea, vomiting, dizziness, confusion, abnormal behavior, pharyngitis, conjunctivitis, red face, red neck, hemorrhage, organ failure and the like), oncogenic symptoms (e.g., sarcomas, leukemias and the like, as well as "rare" malignancies, e.g., Kaposi's sarcoma, oral hairy leukoplasia, lymphomas and the like), immunodeficiency symptoms (e.g., opportunistic infections, wasting, rare malignancies, neurological disease, fever, diarrhea, skin rashes and the like), lesions (e.g., warts (e.g., common wart, flat wart, deep hyperkaratotic palmoplantar wart, superficial mosaic type palmoplantar wart and the like), epidermodysplasia, mucosal lesions, ulcers and the like), and systemic symptoms (e.g., fever, chills, headache, muscle pain, bone pain, joint pain, pharyngitis, tonsillitis, sinusitis, otitis, bronchitis, pneumonia, bronchopneumonia, nausea, vomiting, increased salivation, rash, macules, lymphadenopothy, arthritis, ulcers, photosensitivity, weight loss, irritability, restlessness, anxiety, coma, death and the like). Disorders associated with viral infections are described in *Fields Virology* $4^{th}$ Ed. (2001) Lippincott, Williams & Wilkins, and the introduction to medical virology website (web.uct.ac.za/depts./mmi/jmoodie/introvi2.html), incorporated herein by reference in their entirety for all purposes. One of skill in the art will understand that this list is exemplary only and is not exhaustive, as one of skill in the art will readily be able to identify additional disorders associate with viral infections based on the disclosure herein.

In accordance with other examples, methods for treating non-proliferative, degenerative disorders associated with aberrant translation initiation using a compound described herein to alleviate and/or reduce one or more symptoms associated with a non-proliferative, degenerative disorder are disclosed. Treatment of non-proliferative, degenerative diseases is intended to include, but is not limited to, the use of compounds described herein. As used herein, the term "non-proliferative degenerative disorder" is intended to include, but is not limited to, diseases characterized by a loss of function of cells, tissues, and/or organs due to aberrant translation initiation. Non-proliferative degenerative disorders include, but are not limited to, disorders such as Alzheimer's disease, atherosclerosis, arthritis, keloid scars, psoriasis and insulin resistance. One of skill in the art will understand that this list is exemplary only and is not exhaustive, as one of skill in the art will readily be able to identify additional non-proliferative degenerative disorders based on the disclosure herein.

In accordance with other examples, methods for treating disorders characterized by unwanted synthesis and/or abnormal accumulation of one or more mutant and/or wild-type proteins are provided. Treatment of one or more disorders associated with unwanted synthesis and/or abnormal accumulation is intended to include, but is not limited to, the use of a compound of the present invention to reduce or alleviate one or more symptoms characterized by unwanted synthesis and/or abnormal accumulation. Without intending to be bound by scientific theory, contacting a subject afflicted with a disorder characterized by unwanted synthesis and/or abnormal accumulation of one or more mutant and/or wild-type proteins with a compound described herein (e.g., a compound that can inhibit translation initiation) can reduce the load on the protein-folding machinery and, accordingly, may reduce the severity of the disorder. Disorders associated with unwanted synthesis and/or abnormal accumulation of one or more mutant and/or wild-type proteins include, but are not limited to, Tay-Sachs disease, cystic fibrosis, phenylketonuria, Fabry disease, Alzheimer's disease, Huntington's disease, Parkinson's disease, congophilic angiopathy, prion related disorders (i.e., transmissible spongiform encephalopathies such as Creutzfeldt-Jacob disease, kuru, fatal familial insomnia, scrapie, bovine spongiform encephalopathy and the like) and the like. One of skill in the art will understand that this list is exemplary only and is not exhaustive, as one of skill in the art will readily be able to identify additional disorders characterized by unwanted synthesis and/or abnormal accumulation of one or more mutant and/or wild-type proteins based on the disclosure herein.

In accordance with certain other examples, kits for treating one or more (1) proliferative disorders, (2) non-proliferative, degenerative disorders, (3) viral infections, and/or (4) disorders associated with viral infections are provided. In one example, the kit may comprise one or more compounds of the present invention, or a combination of one or more compounds of the present invention. In another example, the kit may comprise a pharmaceutically acceptable carrier. In an additional example, the kit may also include instructions for treating (1) proliferative disorders, (2) non-proliferative, degenerative disorders, (3) viral infections, and/or (4) disorders associated with viral infections. In some examples, the kit may also comprise, e.g., a buffering agent, a preservative, or a protein stabilizing agent. In other examples, the kit may also contain a control sample or a series of control samples which can be assayed and compared to the test sample contained. Other suitable components for including in the kit will be selected by the person of ordinary skill in the art, given the benefit of this disclosure.

In accordance with certain examples, compounds of the present invention can be incorporated into pharmaceutical compositions suitable for administration. Such compositions typically comprise the compounds disclosed here and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In accordance with certain examples, a pharmaceutical composition of the invention is formulated to be compatible with its intended route of administration. Such pharmaceutical compositions may be administered by inhalation, transdermally, orally, rectally, transmucosally, intestinally, parenterally, intramuscularly, subcutaneously, intravenously or other suitable methods that will be readily selected by the person of ordinary skill in the art, given the benefit of this disclosure. For example, solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

In accordance with other examples, pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMPHOR EL™ (BASF, Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

In accordance with other examples, sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation can be vacuum drying and freeze-drying which yields a powder of the active ingredient plus any additional desired ingredient from a previously sterile-filtered solution thereof. Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In at least certain examples, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811, incorporated herein by reference in its entirety for all purposes.

According to certain exemplary embodiments, the compounds of the present invention can be chemically modified to include or attach polyethylene glycol (PEG) to the compound in a process referred to as PEGylation. Specific advantages of PEGylation include increased efficacy, reduced dosing frequency, reduced toxicity, reduced immunogenicity, reduced side effects, increased stability, increased shelf-life, increased half-life and enhanced solubility. The compounds may be PEGylated directly or through a linker according to the methods known to those of skill in the art such as Davis, *Adv. Drug Deliv. Rev.* 54, 457-458 (2002), Veronese, Bioorg. Med. Chem. Lett, 12, 177-180 (2002), Harris, Adv. Drug. Deliv. Rev, 54, 459-476 (2002), Chapman, Nature Biotechnology 17, 780-783 (1999), and Sato, Adv. Drug Deliv. Rev. 54, 487-504 (2002) hereby incorporated by reference in their entireties and other references readily available to those of skill in the art. Similarly, the compounds can be chemically glysocylated insofar as saccharides are linked to the compound using methods known to those of skill in the art. Examples of glycosylation include N-linked glycosylation and O-linked glycosylation. Specific advantages of glycosylation include increased efficacy, reduced dosing frequency, reduced toxicity, reduced immunogenicity, reduced side effects, increased stability, increased shelf-life, increased half-life and enhanced solubility. Further embodiments of the compounds include dimers, trimers, oligomers, etc. thereof. It is to be understood that modifications of the compounds of the present invention include modifications, chemical, physical or otherwise, to a core compound used by those of skill in the art to increase efficacy, reduce dosing frequency, reduced toxicity, reduced immunogenicity, reduced side effects, increased stability, increased shelf-life, increased half-life and enhanced solubility such as PEGylation or glycosylation or dimerization other methods known to those of skill in the art.

In accordance with certain examples, pharmaceutical compositions of the invention comprise one or more compounds of the present invention covalently linked to a peptide (i.e., a polypeptide comprising two or more amino acids). Peptides may be assembled sequentially from individual amino acids or by linking suitable small peptide fragments. In sequential assembly, the peptide chain is extended stepwise, starting at the C-terminus, by one amino acid per step. In fragment coupling, fragments of different lengths can be linked together, and the fragments can also be obtained by sequential assembly from amino acids or by fragment coupling of still shorter peptides.

In both sequential assembly and fragment coupling it is necessary to link the units (e.g., amino acids, peptides, compounds and the like) by forming an amide linkage, which can be accomplished via a variety of enzymatic and chemical methods. The methods described herein for formation of peptidic amide linkages are also suitable for the formation of non-peptidic amide linkages.

Chemical methods for forming the amide linkage are described in detail in standard references on peptide chemistry, including Muller, *Methoden der organischen Chemie* Vol. XV/2, 1-364, Thieme Verlag, Stuttgart, (1974); Stewart and Young, *Solid Phase Peptide Synthesis,* 31-34 and 71-82, Pierce Chemical Company, Rockford, Ill. (1984); Bodanszky et al., *Peptide Synthesis,* 85-128, John Wiley & Sons, New York, (1976); *Practice of Peptide Synthesis*, M. Bodansky, A. Bodansky, Springer-Verlag, 1994 and other standard works in peptide chemistry, incorporated herein by reference in their entirety for all purposes. Methods include the azide method, the symmetric and mixed anhydride method, the use of in situ generated or preformed active esters, the use of urethane protected N-carboxy anhydrides of amino acids and the formation of the amide linkage using coupling reagents, such as dicyclohexylcarbodiimide (DCC), diisopropylcarbodiimide (DIC), 1-ethoxycarbonyl-2-ethoxy-1,2-dihydroquinoline (EEDQ), pivaloyl chloride, 1-ethyl-3-(3-dimethylaminopropyl)carbodiimide hydrochloride (EDCI), n-propane-phosphonic anhydride (PPA), N,N-bis(2-oxo-3-oxazolidinyl) amido phosphoryl chloride (BOP-Cl), bromo-tris-pyrrolidinophosphonium hexafluorophosphate (PyBrop), diphenylphosphoryl azide (DPPA), Castro's reagent (BOP, PyBop), O-benzotriazolyl-N,N,N',N'-tetramethyluronium salts (HBTU), O-azabenzotriazolyl-N,N,N',N'-tetramethyluronium salts (TATU), diethylphosphoryl cyanide (DEPCN), 2,5-diphenyl-2,3-dihydro-3-oxo-4-hydroxythiophene dioxide (Steglich's reagent; HOTDO), 1,1'-carbonyldiimidazole (CDI) and the like. The coupling reagents can be employed alone or in combination with additives such as N,N-dimethyl-4-aminopyridine (DMAP), N-hydroxy-benzotriazole (HOBt), N-hydroxybenzotriazine (HOOBt), N-hydroxysuccinimide (HOSu), 2-hydroxypyridine and the like.

In accordance with other examples, methods of modulating translation initiation for therapeutic purposes are disclosed. In one example, a method involves contacting a cell with an agent that inhibits translation initiation. An agent that inhibits translation initiation can be any one of the compounds described herein. In at least certain examples, the compound modulates or otherwise inhibits the interaction of eIF4E and eIF4G. Methods of modulating translation initiation can be performed in vitro (e.g., by culturing a cell with the agent) or, alternatively, in vivo (e.g., by administering the agent to a subject). Certain examples disclosed herein are directed to methods of treating an individual afflicted with a disease or disorder characterized by aberrant translation initiation. Examples of such disorders are described herein. In one embodiment, the method involves administering a compound or a combination of compounds describe herein that inhibits translation initiation. As used herein, an individual afflicted with a disease or disorder is intended to include both human and non-human mammals. Examples of non-human mammals include, but are not limited to, non-human primates, horses, cows, goats, sheep, dogs, cats, mice, rats, hamsters, guinea pigs and the like.

The present invention provides for both prophylactic and therapeutic methods of treating a subject for one or more (1) proliferative disorders, (2) non-proliferative, degenerative disorders, (3) viral infections, (4) disorders associated with viral infection, and/or (5) nonproliferative metabolic disorders such as type II diabetes where inhibition of translation initiation is beneficial. In one aspect, the invention provides a method for preventing in a subject, a disease or condition associated with one or more (1) proliferative disorders, (2) non-proliferative, degenerative disorders, (3) viral infections, (4) disorders associated with viral infection, and/or (5) non-proliferative metabolic disorders such as type II diabetes where inhibition of translation initiation is beneficial by administering, to the subject one or more compounds described herein to modulate one or more (1) proliferative disorders, (2) non-proliferative, degenerative disorders, (3) viral infections, (4) disorders associated with viral infection, and/or (5) nonproliferative metabolic disorders such as type II diabetes where inhibition of translation initiation is beneficial. Administration of a prophylactic agent can occur prior to the manifestation of symptoms, such that a disease or disorder is prevented or, alternatively, delayed in its progression.

Another aspect of the invention pertains to therapeutic methods of treating one or more (1) proliferative disorders, (2) non-proliferative, degenerative disorders, (3) viral infections, (4) disorders associated with viral infection for therapeutic purposes, and/or (5) nonproliferative metabolic disorders such as type II diabetes where inhibition of translation initiation is beneficial. Accordingly, in an exemplary embodiment, a therapeutic method of the invention involves contacting a subject with one or more compounds described herein that therapeutically treats one or more (1) proliferative disorders, (2) non-proliferative, degenerative disorders, (3) viral infections, (4) disorders associated with viral infection and/or (5) nonproliferative metabolic disorders such as type II diabetes where inhibition of translation initiation is beneficial.

One embodiment of the present invention involves a method of treating a translation initiation-associated disease or disorder which includes the step of administering a therapeutically and/or prophylactically effective amount of a compound which inhibits translation initiation to a subject. In another embodiment, a subject is administered a therapeutically and/or prophylactically effective amount that is effective to inhibit interaction of eIF4E and eIF4G. As defined herein, a therapeutically and/or prophylactically effective amount of agent (i.e., an effective dosage) ranges from about 0.001 to 30 mg/kg body weight, from about 0.01 to 25 mg/kg body weight, from about 0.1 to 20 mg/kg body weight, from about 1 to 10 mg/kg, from about 2 to 9 mg/kg, from about 3 to 8 mg/kg, from about 4 to 7 mg/kg, or from about 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Treatment of a subject with a therapeutically and/or prophylactically effective amount of an inhibitor can include a single treatment or can include a series of treatments. It will also be appreciated that the effective dosage of in used for treatment may increase or decrease over the course of a particular treatment.

EXAMPLE I

Synthesizing eIF4E/eIF4G Inhibiting Compounds

Specific representative compounds within the scope of the present disclosure have been made and characterized as follows. Compounds described herein were purified either by re-crystallization or by column chromatography, and were characterized by $^1$H nuclear magnetic resonance (NMR) and liquid-chromatography-atmospheric pressure chemical ionization-mass spectrometry (LC-APCI-MS).

EXAMPLE II

Synthesis of 2-quinoline Triazole Derivatives

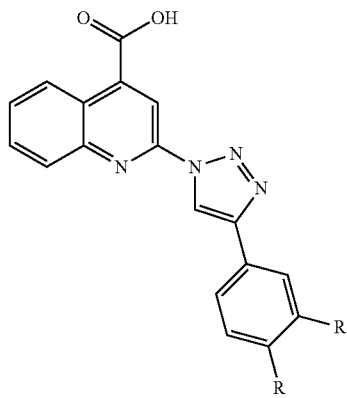

R = H
R = Cl

General Scheme:

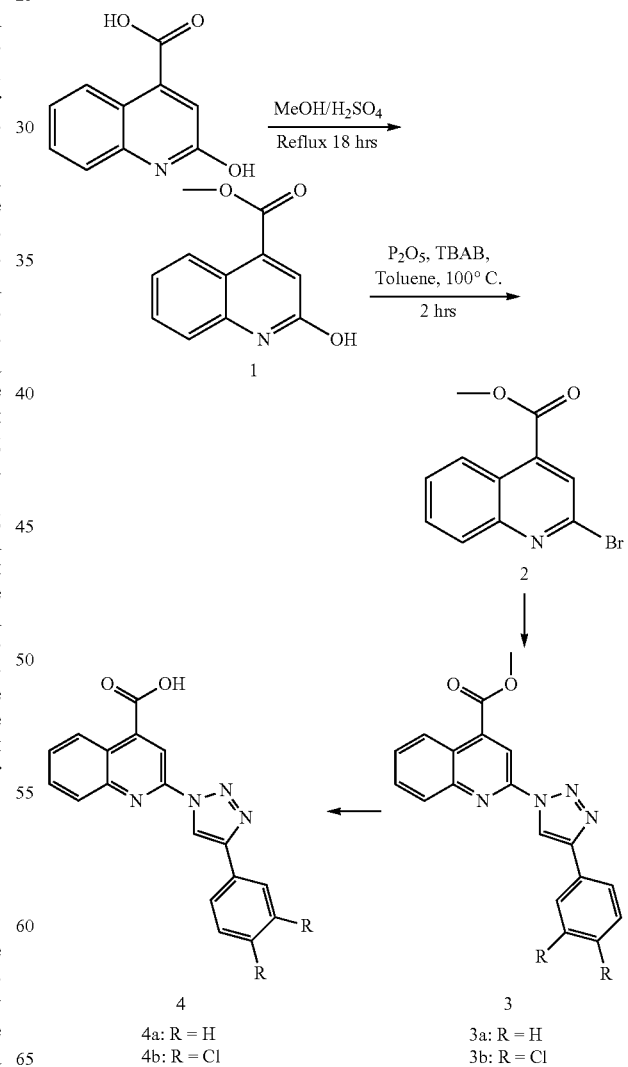

4a: R = H
4b: R = Cl

3a: R = H
3b: R = Cl

Methyl 2-hydroxyquinoline-4-carboxylate, 1: 500 mg of 2-hydroxyquinoline-4-carboxylic acid (2.65 mmol) were suspended in anhydrous methanol and 40 drops of concentrated H$_2$SO$_4$ (96%) were added. Then the reaction was heated to reflux, the solution became clear, it was allowed to stir under reflux for 18 hrs (until no starting material was observed in LC-MS). Then it was cooled to room temperature, a white precipitate was produced. The precipitate was filtrated and washed with diethylether. White solid, 70% (0.38 g) yield. $^1$H NMR (DMSO, INOVA-400): δ3.91 (s, 3H), 6.88 (d, 1H, J=1.6 Hz), 7.22 (td, 1H, J$_t$=7.5 Hz, J$_d$=0.8 Hz), 7.35 (d, 1H, J=8.4 Hz), 7.55 (td, 1H, J$_t$=7.2 Hz, J$_d$=1.2 Hz), 8.05 (d, 1H, J=8.4 Hz), 12.15 (s, 1H). $^{13}$C {$^1$H} NMR (DMSO, INOVA-400): δ 53.64, 116.10, 116.53, 123.05, 124.70, 126.58, 131.78, 140.10, 140.64, 161.45, 166.20; LC-MS (ES+): m/z 203.90, calcd 203.06 (M+).

Methyl 2-bromoquinoline-4-carboxylate, 2: 0.203 g of methyl 2-hydroxyquinoline-4-carboxylate (1 mmol) were dissolved in 20 ml of dry toluene, then 0.356 mg of P$_2$O$_5$ (2.5 mmol) were added and the reaction was heated to 100° C. for 2 hrs. After cooling to room temperature, toluene was washed with 25 ml of saturated NaHCO$_3$ then with 25 ml of brine, then dried over sodium sulfate and solvent evaporated to get the product. Yellowish solid, 89% (0.237 g). $^1$H NMR (DMSO, INOVA-500): δ4.00 (s, 3H), 7.81 (td, 1H, J$_t$=7.2 Hz, J$_d$=1.0 Hz), 7.92 (td, 1H, J$_t$=7.5 Hz, J$_d$=1.5 Hz), 8.06 (s, 1H), 8.08 (d, 1H, J=8.57 Hz), (d, 1H, J=8.0 Hz). $^{13}$C {$^1$H} NMR (DMSO, INOVA-500): δ 56.73, 123.84, 126.34, 127.03, 129.40, 129.54, 132.15, 138.60, 141.40, 149.43, 165.46; LC-MS (ES+): m/z 265.94, 267.94. calcd 265.97, 267.97 (M+).

General Procedure for Compounds 3: 1 mmol of methyl 2-bromoquinoline-4-carboxylate was dissolved 2 ml DMSO, then 1.05 equiv of Sodium azide were added, 1.0 equivalents of the desired phenylacetylene derivative, 0.1 equivalents of sodium ascorbate, 0.1 equiv of CuI and 0.15 equiv of N,N'-dimethylcyclohexane-1,2-diamine were added subsequently. The reaction was then allowed to reflux for 18 hrs. Then cooled to room temperature and 5 ml of brine were added, a precipitate was formed, which was then separated and washed with cold water. The product was purified using reversed phase column chromatography using gradient increase of methanol percentage in DDW-0.1% formic acid.

Methyl 2-(4-phenyl-1H-1,2,3-triazol-1-yl)quinoline-4-carboxylate, 3a: yellow solid, 85% (280 mg) yield, $^1$H NMR (DMSO, INOVA-400): δ4.01 (s, 3H), 7.44 (m, 2H), 7.88 (t, 1H, J=8.0 Hz), 7.88 (s, 1H), 8.04 (t, 1H, J=6.5 Hz), 8.60 (s, 1H), 8.68 (d, 1H, J=8.0 Hz), 8.72 (d, 1H, J=8.0 Hz).

Methyl 2-(4-(3,4-dichlorophenyl)-1H-1,2,3-triazol-1-yl) quinoline-4-carboxylate, 3b: yellow solid, 17% (67 mg) yield, $^1$H NMR (CDCl$_3$, INOVA-500): δ4.01 (s, 3H), 6.90 (d, 1H, J=8.0 Hz), 7.34 (m, 2H), 7.41 (m, 2H), 7.49 (d, 1H, J=8.0 Hz), 7.66 (d, 1H, J=8.5 Hz), 7.67 (s, 1H), 7.91 (s, 1H).

General Procedure for Compounds 4: 0.155 mmol of the ester derivative was dissolved in 1 mL MeOH, then 1 mL of DDW were added, and then 0.2 equiv of NaOH were added (2.64 mg). The reaction was stirred at room temperature for 4 hrs, the precipitate was separated and washed with ether and dried under vacuum pump.

4-(4-phenyl-1H-1,2,3-triazol-1-yl)quinoline-2-carboxylic acid, 4a: yellowish solid, 95% (45 mg) yield. $^1$H NMR (DMSO, INOVA-400): δ 7.45 (m, 2H), 7.58 (s, 1H), 7.60 (t, 1H, J=8.0 Hz), 7.73 (t, 2H, J=6.5 Hz), 7.87 (s, 1H), 7.89 (d, 2H, J=8.0 Hz), 8.57 (d, 1H, J=8.0 Hz), 8.89 (d, 1H, J=8.0 Hz). HPLC (30 to 70 ACN/DDW-0.1% TFA in 25 min): 13.715 min, 98.54%.

4-(4-(3,4-dichlorophenyl)-1H-1,2,3-triazol-1-yl)quinoline-2-carboxylic acid, 4b: yellow solid, 95% (27.5 mg), $^1$H NMR (CDCl$_3$, INOVA-500): δ 6.90 (d, 2H, J=8.0 Hz), 7.33 (d, 1H, J=7.0 Hz), 7.34 (s, 1H), 7.41 (m, 2H), 7.48 (d, 1H, J=8.5 Hz), 7.66 (dd, 1H, J$_1$=8.5 Hz, J$_2$=2.0 Hz), 7.67 (s, 1H), 7.91 (d, 1H, J=2.0 Hz). HPLC (30 to 70 ACN/DDW-0.1% TFA in 25 min): 9.072 min, 95.23%.

EXAMPLE III

Synthesis of 4-Quinoline Triazole Derivatives

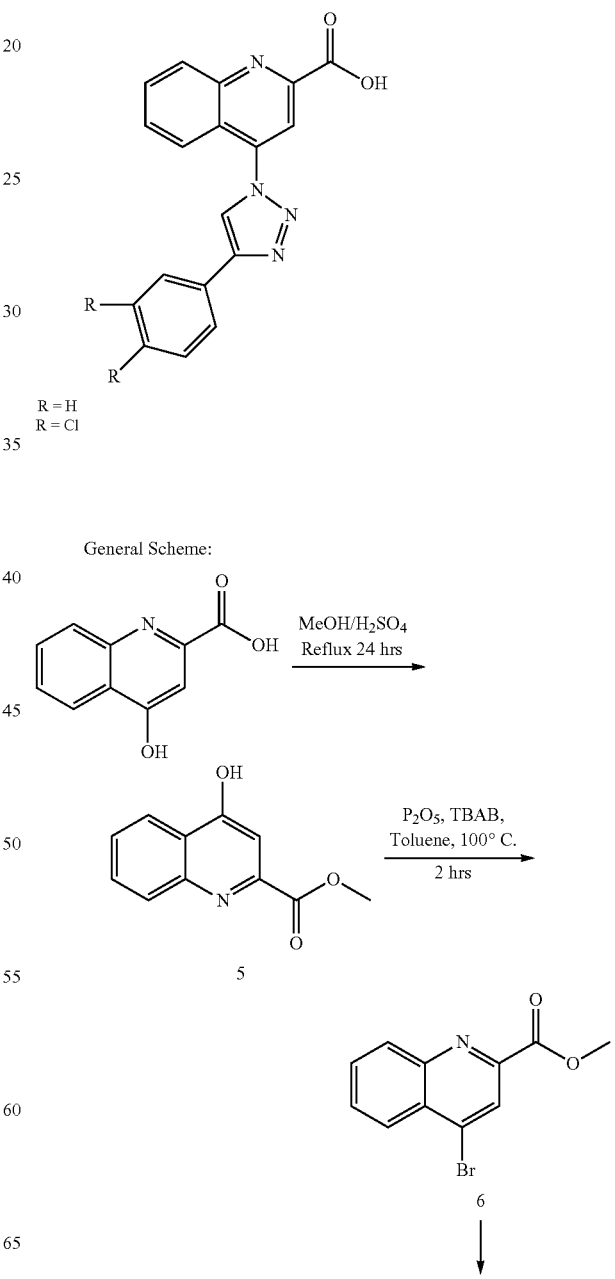

-continued

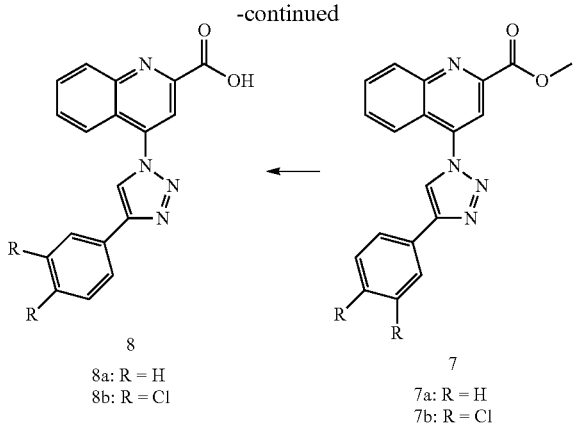

8
8a: R = H
8b: R = Cl 7
7a: R = H
7b: R = Cl

Methyl 4-hydroxyquinoline-2-carboxylate, 5: 500 mg of kynurenic acid (2.65 mmol) were suspended in anhydrous methanol and 40 drops of concentrated $H_2SO_4$ (96%) were added, the solution became clear. Then the reaction was heated to reflux and allowed to react under reflux for 24 hrs (until no starting material was observed in LC-MS). Then it was cooled to room temperature. The solvent was evaporated to dryness using rotatory evaporator. The produced solid was dissolved in 1 ml of methanol, and 10 ml of DDW were added. Addition of saturated sodium bicarbonate produced a white precipitate. The precipitate was filtrated and washed with diethylether. White solid, 65% (0.35 g). $^1$H NMR (DMSO, INOVA-500): δ3.52 (s, 3H), 6.48 (s, 1H), 7.25 (t, 1H, J=7.0 Hz), 7.58 (t, 1H, J=7.0 Hz), 7.96 (d, 1H, J=8.5 Hz), 8.05 (d, 1H, J=8.5 Hz), 11.32 (s, 1H); LC-MS (ES+): m/z 204.09, calcd 204.06 (M+).

Methyl 4-bromoquinoline-2-carboxylate, 6: 0.203 g of methyl 2-hydroxyquinoline-4-carboxylate (1 mmol) were dissolved in 20 ml of dry toluene, then 0.356 mg of $P_2O_5$ (2.5 mmol) were added and the reaction was heated to 100° C. for 2 hrs. After cooling to room temperature, toluene was washed with 25 ml of saturated $NaHCO_3$ then with 25 ml of brine, then dried over sodium sulfate and solvent evaporated to get the product. Yellowish solid, 50% (0.13 g). $^1$H NMR (DMSO, INOVA-500): δ 3.97 (s, 3H), 7.92 (t, 1H, J=7.0 Hz), 7.99 (t, 1H, J=7.0 Hz), 8.23 (d, 2H, J=7.5 Hz), 8.41 (s, 1H). $^{13}$C {$^1$H} NMR (DMSO, INOVA-500): δ 53.64, 125.27, 127.06, 131.34, 131.38, 132.55, 148.24, 165.46. LC-MS (ES+): m/z 265.94, 267.94, calcd 265.97, 267.97 (M+).

General Procedure for Compounds 7: 1 mmol of methyl 4-bromoquinoline-2-carboxylate was dissolved 2 ml DMSO, then 1.05 equiv of sodium azide and 1 equiv the desired phenylacetylene derivative were added. Then 0.1 equiv of sodium ascorbate, 0.1 equiv of CuI and 0.15 equiv of N,N'-dimethylcyclohexane-1,2-diamine were added and the reaction was allowed to reflux for 18 hrs. Then 5 ml of brine were added, a precipitate was formed, which was then separated and washed with cold water. The product was purified using reversed phase column chromatography using gradient increase of methanol percentage in DDW-0.1% formic acid.

General Procedure for Compounds 8. 30 mg of the ester derivative was dissolved in 1.5 ml of 1:1 MeOH/DDW solution, and then 10 equiv of NaOH were added. The reaction was stirred at room temperature for 4 hrs, then solvent evaporated. The compound was purified using reversed phase column chromatography using gradient increase of methanol percentage in DDW as eluent.

EXAMPLE IV

Synthesis of Naphthalic Triazole Derivatives

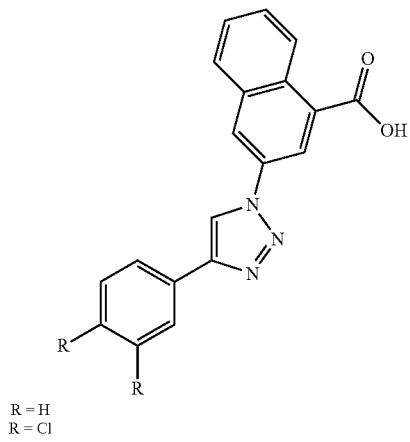

R = H
R = Cl

General Scheme:

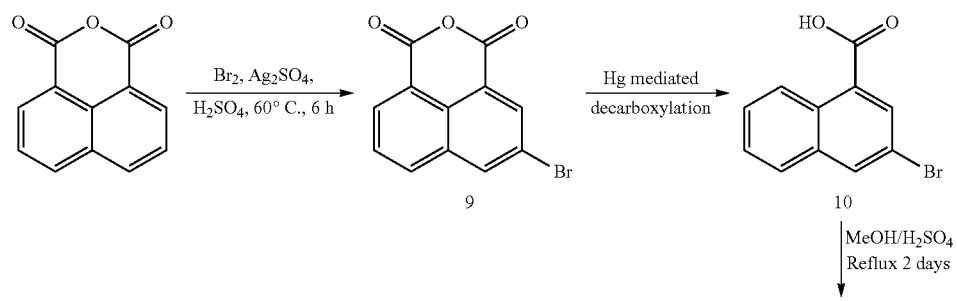

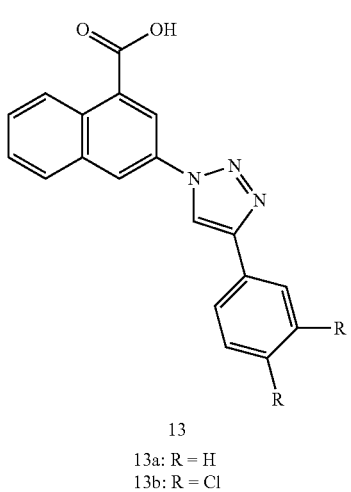

13
13a: R = H
13b: R = Cl 12
12a: R = H
12b: R = Cl 3-bromonaphthoic anhydride, 9: To a solution of (0.4 g, 1 mmol) of naphthalic anhydride in 8 ml of Sulfuric acid, (0.312 g, 0.5 mmol) of silver sulfate was added. Then 2.5 mmol of Bromine was added drop-wisely. After addition was complete the reaction was heated to 65° C. under stirring for 6 hrs. After cooling to room temperature, the reaction mixture was filtrated, and the filtrate was poured carefully into 50 ml of ice-distilled water. A precipitate was immediately formed, which was then filtrated and washed with cold water and Ethanol. TLC in 7% MeOH/DCM showed new product ($R_f$=0.84). $R_f$ for starting material was 0.75. White solid, 80% (0.428 g) yield. $^1$H NMR (CDCl$_3$, INOVA-400): δ 7.86 (t, 1H, J=7.6 Hz), 8.25 (d, 1H, J=8.0 Hz), 8.50 (d, 1H, J=1.6 Hz), 8.64 (dd, 1H, $H_1$=7.2 Hz, $J_2$=1.2 Hz), 8.69 (d, 1H, J=2.0 Hz).

3-bromonaphthalic acid, 10: 0.25 g of 3-bromonaphthoic anhydride (0.9 mmol) were dissolved in 15 ml of 0.4 N NaOH, then heated to 60° C., and followed by LC-MS until the peak in the UV detection almost disappeared (it doesn't ionize). Then 0.21 g of HgO (1.1 equiv) were dissolved in 2 ml of 50% AcOH aqueous solution, then the reaction mixture was heated to 100° C. and allowed to react for 5 days. It was then cooled to room temperature and 50 ml of 5 N HCl were added, and the reaction was reheated to 100° C. and stirred for additional 4 hrs. It was then cooled to 0° C. in an ice-bath, a precipitate was produced. The precipitate was collected and washed with cold water. White solid, 58% (0.13 g) yield. $^1$H NMR (DMSO, INOVA-400): δ 7.94 (t, 1H, J=7.6 Hz), 8.48 (d, 1H, J=8.0 Hz), 8.49 (s 1H), 8.52 (dd, 1H, $J_1$=7.6 Hz, $J_2$=1.2 Hz), 8.85 (d, 1H, J=2.0 Hz). LC-MS (ES-): m/z 248.84, 250.84, Calcd: 248.96, 250.96 (M$^-$).

Methyl 3-bromo-1-naphthoate, 11: 500 mg of 3-bromo-1-naphthoic acid were dissolved in 25 mL of anhydrous Methanol and 50 drops of conc. H$_2$SO$_4$ was added, then the reaction heated to reflux for 24 hrs. Then cooled to room temperature, no precipitate was formed, so methanol was evaporated to get a white precipitate. White solid, 80% (0.42 g) yield. $^1$H NMR (DMSO, INOVA-500): δ 3.36 (s, 3H), 7.90 (t, 1H, J=7.6 Hz), 8.43 (d, 1H, J=8.0 Hz), 8.48 (s 1H), 8.46 (dd, 1H, $J_1$=7.6 Hz, $J_2$=1.2 Hz), 8.79 (d, 1H, J=2.0 Hz).

General Procedure for Compounds 12: 0.2 g of methyl 3-bromo-1-naphthoate (0.76 mmol) was dissolved 2 ml DMSO, then 1.05 equiv of Sodium azide were added (51.7 mg), then 1 equiv of the desired phenylacetylene derivative were added. Then 0.1 equiv of sodium ascorbate (11.3 mg), 0.1 equiv of CuI (14.5 mg), and 0.15 equiv of N,N'-dimethylcyclohexane-1,2-diamine (16.2 mg) were added subsequently and the reaction allowed to reflux for 18 hrs, then 5 ml of brine were added, a precipitate was formed. The precipitate was filtrated and washed with cold water. The product was purified using reversed phase column chromatography using gradient increase of methanol percentage in DDW-0.1% formic acid.

Methyl 3-(4-phenyl-1H-1,2,3-triazol-1-yl)-1-naphthoate, 12a: yellow solid, 15% yield. LC-MS (ES+): m/z 330.08, Calcd: 330.12 (M+). HPLC (30 to 70 ACN/DDW-0.1% TFA in 25 min): 13.983 min, 95.87%.

Methyl 3-(4-(3,4-dichlorophenyl)-1H-1,2,3-triazol-1-yl)-1-naphthoate, 12b: yellow solid, 16% yield. LC-MS (ES+): m/z 398.01, 400.29, Calcd: 398.04, 400.04 (M+).

General Procedure for Compounds 13: compound 12 was dissolved in 15 ml of 1:1 MeOH/DDW solution and then 10 equiv of NaOH were added. The reaction was stirred at room temperature for 4 hrs, then solvent evaporated. The product was purified using reversed phase column chromatography using gradient increase of methanol percentage in DDW-0.1% formic acid.

EXAMPLE V

Synthesis of Templated Click 4EGI-1-Triazole Analogues

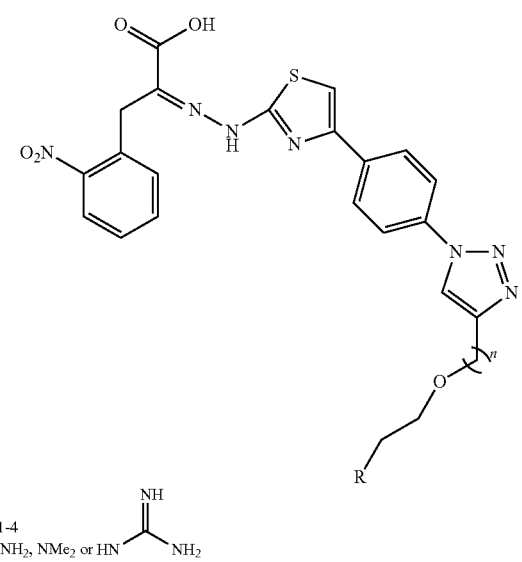

n = 1-4
R = NH$_2$, NMe$_2$ or HN–C(=NH)–NH$_2$

General Scheme:

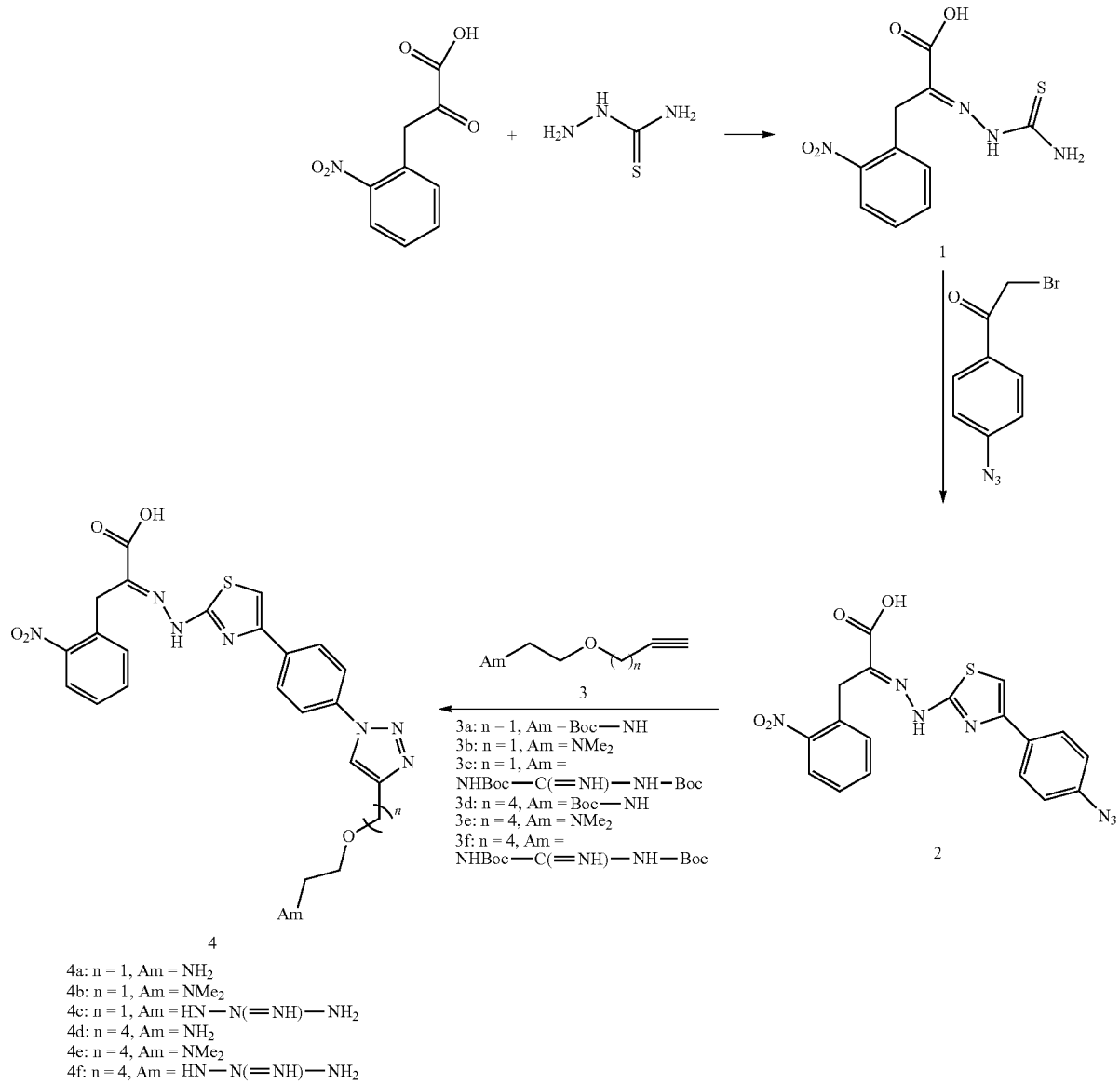

4a: n = 1, Am = NH₂
4b: n = 1, Am = NMe₂
4c: n = 1, Am = HN—N(=NH)—NH₂
4d: n = 4, Am = NH₂
4e: n = 4, Am = NMe₂
4f: n = 4, Am = HN—N(=NH)—NH₂

2-(2-carbamothioylhydrazono)-3-(2-nitrophenyl) propanoic acid, 1: 1 g (4.781 mmol) of 2-Nitrophenylpyruvic acid and 0.436 g (4.781 mmol) of Thiosemicarbazide were dissolved in 40 mL of Ethanol, then 20 mL of 5% AcOH/DDW were added and the reaction was refluxed for 2 hours. Then cooled to R.T then cooled to room temperature, a precipitate was formed, which was filtrated, washed with cold water and dried under vacuum. Light yellow solid, 99.8% (1.345 g) yield. Isomer E: $^1$H NMR (DMSO, INOVA-500): δ4.36 (s, 2H), 6.98 (s, 1H), 7.51 (m, 2H), 7.63 (t, 1H, J=7.5 Hz), 8.05 (d, 1H, J=7.5 Hz), 8.82 (s, 2H), 11.21 (s, 1H). $^{13}$C {$^1$H} NMR (DMSO, INOVA-500): δ 29.38, 125.77, 128.54, 129.69, 131.71, 134.50, 137.65, 149.51, 165.31, 180.70. Isomer Z: $^1$H NMR (DMSO, INOVA-500): δ4.09 (s, 2H), 6.96 (s, 1H), 7.51 (t, 1H, J=7.5 Hz), 7.63 (m, 2H), 7.96 (d, 1H, J=7.5 Hz), 8.76 (s, 2H), 12.13 (s, 1H). $^{13}$C {$^1$H} NMR (DMSO, INOVA-500): δ 36.08, 125.08, 128.86, 132.18, 132.72, 134.02, 135.18, 150.05, 164.15, 179.28. LC-MS (ES+): two peaks with m/z 282.96 were obtained, which corresponds to E and Z isomers, calcd 283.04 (M+).

2-(2-(4-(4-azidophenyl)thiazol-2-yl)hydrazono)-3-(2-nitrophenyl)propanoic acid, 2: 300 mg of 2-(2-carbamothioylhydrazono)-3-(2-nitrophenyl) propanoic acid (1.06 mmol), and 255 mg of 4-azidophenacyl bromide (1.06 mmol), were dissolved in 2 mL of Dry Dioxane, then allowed to react at room temperature for 18 hrs, a precipitate was formed, the precipitate was collected, washed with Dioxane and cold water then dried under vacuum. White solid, 98% (0.44 g) yield. Isomer E: $^1$H NMR (DMSO, INOVA-500): δ4.196 (s, 2H), 7.13 (d, 2H, J=8.5 Hz), 7.36 (s, 1H), 7.54 (m, 2H), 7.72 (t, 1H, J=7.5 Hz), 7.84 (d, 2H, J=8.5 Hz), 8.07 (d, 1H, J=8.5 Hz), 12.76 (s, 1H). $^{13}$C {$^1$H} NMR (DMSO, INOVA-500): δ 36.86, 106.18, 110.91, 120.07, 125.29, 127.88, 128.92, 131.56, 132.62, 133.65, 134.79, 139.52, 141.15, 149.80, 146.72. LC-MS (ES+): m/z 424.00, calcd: 424.07 (M+).

General Procedure for Amine Protection: 1 mmol of the desired amine derivative was dissolved in 20 ml of methanol, then 1.1 equivalents of di-tert-butyldicarbonate was dissolved in additional 20 ml of methanol and then added drop wise to the reaction mixture, and allowed to stir at room temperature for 18 hrs or until TLC (5% MeOH/DCM) showed total conversion. Then solvent evaporated to dryness.

General Procedure for 3: 0.04 g of 60% NaH dispersion in mineral oil (1.0 mmol) were suspended in 20 mL of dry Hexane, then hexane was removed using double ended needle (under nitrogen) to wash out the mineral oil, this was repeated 3 times, then NaH was dried under vacuum. NaH was dissolved in 20 mL of dry THF, and 1.0 equivalent of the desired amino ethanol (1.0 mmol) was added drop wise, then 1.1 mL of the desired n-haloalkyne was drop wisely added to the reaction mixture, and the reaction allowed reacting at room temperature for 2 hrs. The precipitate formed was discarded and the THF was extracted with 20 mL of brine then organic layer was dried over sodium sulfate, then solvent evaporated and vacuum dried to get the desired product.

Tert-butyl 2-(prop-2-ynyloxy)ethylcarbamate, 3a: colorless oil, 43% (0.86 g) yield. $R_f$ (5% MeOH/DCM)=0.77.

N,N-dimethyl-2-(prop-2-ynyloxy)ethanamine, 3b: brown oil, 15% (0.19 g) yield. $R_f$ (10% MeOH/DCM)=0.16. LC-MS (ES+): m/z 127.99, calcd 128.10 (M+).

Di-Boc-2-(2-(prop-2-ynyloxy)ethyl)guanidine, 3c: orange solid, 50% (0.34 g) yield.

Tert-butyl 2-(hex-5-ynyloxy)ethylcarbamate, 3d: white solid, 75% (0.18 g) yield.

2-(hex-5-ynyloxy)-N,N-dimethylethanamine, 3e: orange solid, 75% (0.13 g) yield. (LC-MS (ES+): m/z 170.08, calcd 170.15 (M+).

Di-boc-2-(2-(hex-5-ynyloxy)ethyl)guanidine, 3f: white solid, 80% (0.30 g) yield.

General Procedure for 4: 0.75 mmol 2-(2-(4-(4-azidophenyl)thiazol-2-yl)hydrazono)-3-(2-nitrophenyl)propanoic acid; 2, was dissolved in 3.5 ml of acetonitrile, then 1.5 ml of tert-butanol was added. 150 µL of diisopropylamine was added. Then (1 mmol) of 3 was added. Then 0.33 equiv of CuI and sodium ascorbate were added and the reaction stirred for 18 hrs at room temperature. Then solvent was partially evaporated. Then 20 ml of cold water were added, a precipitate formed. The precipitate was separated and washed with cold water and ether. Then it was dried over vacuum pump. The product was purified using reversed phase column chromatography using gradient increase of methanol percentage in DDW-0.1% formic acid. In protected amines the product was dissolved in 5 ml of dry DCM, then 5 ml TFA were added and the reaction was stirred at room temperature for 1-2 hrs. Then the solvent evaporated to dryness and the product purified using reversed phase column chromatography using gradient increase of methanol percentage in DDW-0.1% formic acid.

Table 1 below includes experimental data for the synthesized 4EGI-1 derivatives with the following general structure:

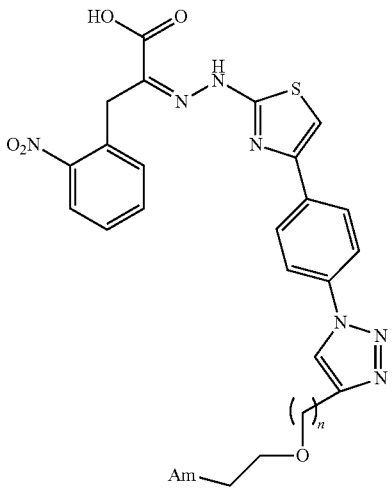

| | | | | HPLC | | | SRB-IC50 (µM) | |
| Compound | n | Am | RT(min)[a] | LC-MS (ES+) | Yield* | 2351 | 2813 |
|---|---|---|---|---|---|---|---|
| 4a | KH41 | 1 | NH$_2$ | 15.076 | Calc: 526.14. Found M+: 523.21. | Yellow solid 65% | NA | NA |
| 4b | KH22 | 1 | NMe$_2$ | 15.000 | Calc: 551.17. Found M+: 551.20 | Pale yellow solid 50% | NA | NA |
| 4c | KH28B | 1 | Boc—NC(=NH)—NH—Boc | | Calc: 756.27. Found M+: 765.27 | Pale yellow solid 65% | | |
| 4d | KH30B | 4 | Boc—NH | | Calc: 665.24. Found M+: 665.97 | Pale yellow solid 60% | | |
| 4e | KH29B | 4 | NMe$_2$ | F: 15.115 S: 15.978 | Calc: 593.22. Found M+: | Yellow solid 75% | NA | NA |
| 4f | KH31B | 4 | Boc—NC(=NH)—NH—Boc | | Calc: 806.32. Found M+: | Brown solid 75% | | |
| 4EGI-1 | | | | | | | 6.5 | 1.3 |

*Isolated Yield,
[a] 30 to 70 ACN/DDW in 25 min.

EXAMPLE VI
Synthesis of Templated Click 4EGI-1-Triazole Analogues with Spacer
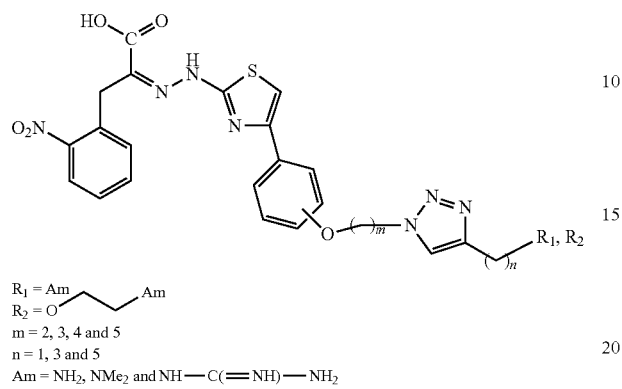
R₁ = Am$\underset{\hspace{2em}}{\diagup\hspace{-0.5em}\diagdown}$Am
R₂ = O$\underset{\hspace{2em}}{\diagup\hspace{-0.5em}\diagdown}$
m = 2, 3, 4 and 5
n = 1, 3 and 5
Am = NH₂, NMe₂ and NH—C(=NH)—NH₂
General Scheme:
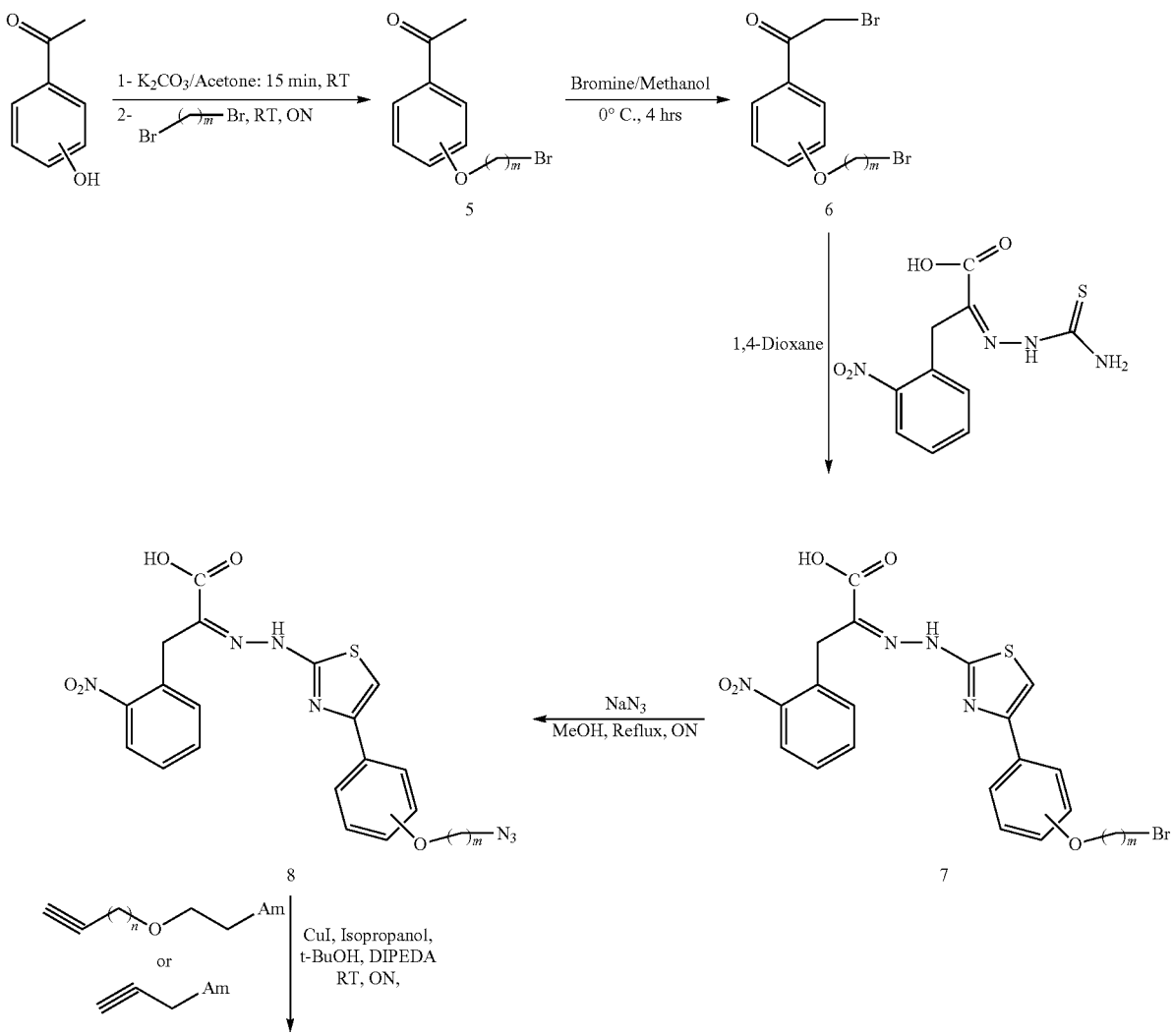

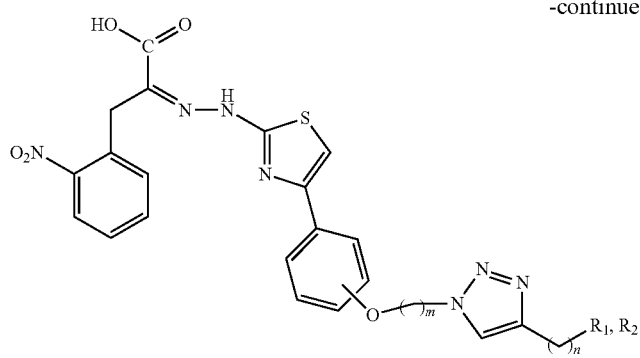

9

$R_1$ = Am

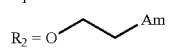 Am m = 2, 3, 4 and 5
n = 1, 3 and 5
Am = $NH_2$, $NMe_2$ and NH—C(=NH)—$NH_2$ General Procedure for the Synthesis of Bromoalkoxyacetophenones, 5: 1 g of 4'-hydroxyacetophenone (7.345 mmol) was dissolved in 20 ml of dry acetone. Then 3 equiv of potassium carbonate were added (3 g). and the reaction was stirred for 15 min, then 1.1 equiv of 1, m-dibroalkane were added and the reaction stirred at room temperature for 18 hrs. Then the precipitate was discarded and the filtrate was evaporated to dryness. The product was purified using normal phase column chromatography using gradient increase of methanol in DCM as mobile phase.

Table 2 includes experimental data for the synthesized bromoalkoxyacetophenones, 5:

| | Position on the ring | Chain length (n) | $^1$H-NMR (CDCl$_3$) | $^{13}$C {1H}-NMR (CDCl$_3$) | Yield* |
|---|---|---|---|---|---|
| KH125 | p- | 2 | δ 2.56 (s, 3H), 3.66 (t, 2H, J = 6.0 Hz), 4.36 (t, 2H, J = 6.0 Hz), 6.95 (d, 2H, J = 9.0 Hz), 7.94 (d, 2H, J = 9.0 Hz). | δ 26.61, 28.82, 68.09, 114.53, 130.90, 131.14, 162.16, 196.99. | 36%, yellow oil |
| KH126 | p- | 3 | δ 2.32 (m, 2H), 2.53 (s, 3H), 3.59 (t, 2H, J = 6.0 Hz), 4.15 (t, 2H, J = 5.5 Hz), 6.92 (d, 2H, J = 8.5 Hz), 7.91 (d, 2H, J = 8.5 Hz). | δ 26.58, 29.97, 32.34, 65.74, 114.38, 114.61, 130.77, 162.78, 196.90. | 53%, yellow oil |
| KH101 | p- | 4 | δ 1.99 (p, 2H, J = 6.0 Hz), 2.09 (p, 2H, J = 7.0 Hz), 2.58 (s, 3H), 3.50 (t, 2H, J = 6.5 Hz), 4.07 (t, 2H, J = 6.0 Hz), 6.93 (d, 2H, J = 9.0 Hz), 7.94 (d, 2H, J = 8.5 Hz). | δ 26.58, 27.98, 29.58, 33.50, 67.33, 114.34, 130.60, 130.83, 162.99, 196.94. | 81%, yellow oil |
| KH127 | p- | 5 | δ 1.58 (p, 2H, J = 6.5 Hz), 1.78 (p, 2H, J = 7.0 Hz), 1.88 (p, 2H, J = 7.0 Hz), 2.49 (s, 3H), 3.38 (t, 2H, J = 6.5 Hz), 3.97 (t, 2H, J = 6.0 Hz), 6.86 (d, 2H, J = 9.0 Hz), 7.87 (d, 2H, J = 9.0 Hz). | δ 24.96, 26.55, 28.48, 32.62, 33.80, 68.03, 114.32, 130.39, 130.77, 163.10, 196.84. | 81%, yellow oil |
| KH128 | o- | 2 | δ 2.68 (s, 3H), 3.70 (t, 2H, J = 6.0 Hz), 4.38 (t, 2H, J = 6.0 Hz, 6.89 (d, 1H, J = 7.0 Hz), 6.96 (m, 1H), 7.54 (m, 1H), 7.72 (d, 1H, J = 7.0 Hz). | δ 26.53, 32.23, 68.14, 112.14, 118.26, 128.47, 130.66, 133.57, 157.18, 199.46. | 44%, yellow oil |
| KH116 | o- | 4 | δ 2.05 (p, 2H, J = 6.0 Hz), 2.09 (p, 2H, J = 7.0 Hz), 2.63 (s, 3H), 3.50 (t, 2H, J = 6.5 hz), 4.11 (t, 2H, J = 6.0 Hz), 6.95 (d, 1H, J = 7.0 Hz), 7.00 (m, 1H), 7.44 (m, 1H), 7.74 (d, 1H, J = 7.0 Hz). | δ 28.10, 29.71, 32.18, 32.26, 33.41, 67.66, 112.44, 120.89, 128.62, 130.65, 133.86, 158.33, 199.97. | 84%, yellow oil |

-continued

| | Position on the ring | Chain length (n) | $^1$H-NMR (CDCl$_3$) | $^{13}$C {$^1$H} -NMR (CDCl$_3$) | Yield* |
|---|---|---|---|---|---|
| KH131 | m- | 2 | δ 2.57 (s, 3H), 3.64 (t, 2H, J = 6.0 Hz), 4.32 (t, 2H, J = 6.0 Hz), 7.11 (dm, 1H, J = 8.0 Hz), 7.36 (t, 1H, J = 8.0 Hz), 7.46 (m, 1H), 7.55 (dm, 1H, J = 6.0 Hz). | δ 26.69, 29.30, 66.24, 113.48, 120.40, 122.01, 129.97, 138.77, 158.57, 197.88. | 30%, yellow oil |
| KH132 | m- | 3 | δ 2.31 (m, 2H), 2.57 (s, 3H), 3.59 (t, 2H, J = 6.0 hz), 4.13 (t, 2H, J = 5.5 Hz), 7.10 (dm, 1H, J = 5.0 Hz), 7.35 (t, 1H, J = 7.5 Hz), 7.47 (s, 1H), 7.52 (dm, 1H, J = 5.0 Hz). | δ 26.97, 30.11, 32.47, 65.73, 113.36, 120.14, 121.54, 129.95, 138.72, 159.12, 198.02. | 35%, yellow oil |
| KH133 | m- | 4 | δ 1.93 (m, 2H), 2.05 (m, 2H), 2.56 (s, 3H), 3.46 (t, 2H, J = 6.5 Hz), 4.01 (t, 2H, J = 6.5 Hz), 7.07 (ddd, 1H, J$_1$ = 8.5, J$_2$ = 3.0, J$_3$ = 1.0 Hz), 7.34 (t, 1H, J = 8.0 Hz), 7.44 (dd, 1H, J$_1$ = 2.5, J$_2$ = 1.5 Hz), 7.50 (ddd, 1H, J$_1$ = 7.5, J$_2$ = 1.5, J$_3$ = 1.0 Hz). | δ 26.97, 29.05, 29.65, 33.64, 67.29, 113.25, 120.16, 121.37, 129.83, 138.67, 159.29, 198.12. | 28%, orange oil |
| KH134 | m- | 5 | δ 1.62 (p, 2H, J = 7.5 Hz), 1.81 (p, 2H, , J = 7.0 Hz), 1.92 (p, 2H, J = 7.5 Hz), 2.57 (s, 3H), 3.42 (t, 2H, J = 6.5 Hz), 4.00 (t, 2H, J = 6.0 Hz), 7.39 (ddd, 1H, J$_1$ = 8.5, J$_2$ = 2.0, J$_3$ = 1.0 Hz), 7.34 (t, 1H, J = 8.5 Hz), 7.45 (m, 1H), 7.50 (dm, 1H, J = 7.50 Hz). | δ 25.03, 26.96, 28.58, 32.67, 33.81, 68.00, 113.28, 130.16, 121.25, 129.79, 138.67, 1598.40, 198.09. | 27%, yellow oil |

*Isolated Yield

General Procedure for the Synthesis of Bromoalkoxyphenacyl Bromides, 6: 1 mmol of bromoalkoxyacetophenones, 5, was dissolved in 10 ml of MeOH, and cooled to 0° C. Then 1 equiv of bromine were dissolved in 10 of MeOH and then added drop wise to the reaction mixture. Then the reaction allowed warming gradually to room temperature with stirring in a period of 4 hrs. The precipitate was collected and washed with DCM. The product was purified, using normal phase column chromatography (Hexane/ethyl acetate).

Table 3 includes experimental data for the synthesized bromoalkoxyphenacyl bromides:

| | Position on the ring | Chain length (n) | $^1$H-NMR (CDCl$_3$) | $^{13}$C {$^1$H} -NMR (CDCl$_3$) | Yield* |
|---|---|---|---|---|---|
| KH135 | p- | 2 | 3.68 (t, 2H, J = 6.0 Hz), 4.38 (t, 2H, J = 6.0 Hz), δ 4.41 (s, 3H), 6.99 (d, 2H, J = 9.0 Hz), 7.99 (d, 2H, J = 9.0 Hz) | δ 28.70, 30.86, 68.16, 114.53, 127.74, 131.66, 162.78, 190.11, | 44% |
| KH136 | p- | 3 | δ 2.37 (p, 2H, J = 6.5 Hz), 3.62 (t, 2H, J = 6.5 Hz), 4.21 (t, 2H, J = 6.0 Hz), 4.41 (s, 3H), 6.98 (d, 2H, J = 9.0 Hz), 7.98 (d, 2H, J = 9.0 Hz) | δ 29.83, 30.90, 32.29, 65.86, 114.76, 127.34, 131.62, 163.45, 190.14 | 32% |
| KH111 | p- | 4 | δ 2.00 (p, 2H, J = 6.0 Hz), 2.09 (p, 2H, J = 7.0 Hz), 3.50 (t, 2H, J = 6.5 Hz), 4.09 (t, 2H, J = 6.0 Hz), 4.41 (s, 3H), 6.95 (t, 2H, J = 9.0 Hz), 7.97 (d, 2H, J = 9.0 Hz) | δ 27.63, 29.22, 30.63, 33.14, 67.17, 114.39, 126.85, 131.30, 163.34, 189.82. | 54% |

-continued

| | Position on the ring | Chain length (n) | $^1$H-NMR (CDCl$_3$) | $^{13}$C {$^1$H}-NMR (CDCl$_3$) | Yield* |
|---|---|---|---|---|---|
| KH137 | p- | 5 | δ 1.65 (p, 2H, J = 8.5 Hz), 1.97 (m, 4H), 3.46 (t, 2H, J = 6.5 Hz), 4.06 (t, 2H, J = 6.0 Hz), 4.38 (s, 3H), 6.93 (d, 2H, J = 9.5 Hz), 7.93 (d, 2H, J = 8.5 Hz) | δ 24.97, 28.48, 30.98, 32.61, 33.72, 69.40, 114.71, 131.59, 134.63, 163.80, 190.14 | 85% |
| KH138 | o- | 2 | δ 3.77 (t, 2H, J = 6.0 Hz), 4.47 (t, 2H, J = 6.0 Hz), 4.70 (s, 3H), 6.95 (d, 1H, J = 8.0 Hz), 7.10 (td, 1H, J$_t$ = 7.5, J$_a$ = 1.0 Hz), 7.53 (m, 1H), 7.87 (dd, 1H, J$_1$ = 8.0, J$_2$ = 2.0 Hz), | δ 29.08, 37.80, 68.55, 112.29, 122.00, 125.03, 132.12, 134.90, 157.24, 192.63. | 10% |

*Isolated Yield

General Procedure for the Synthesis of 7: 1 mmol of the previously prepared bromoalkoxyphenacyl bromide, 6, was dissolved in 2 ml of 1,4-dioxane, then 1 equiv of the previously prepared 2-(2-carbamothioylhydrazono)-3-(2-nitrophenyl) propanoic acid, 1, were added and the reaction was stirred at room temperature for 12 hrs. Then 10 ml of DDW were added which produced a precipitate. The precipitate was separated and washed with DDW then dried over vacuum pump. The product was then purified using reversed phase chromatography (MeOH/DDW).

Table 4 includes experimental data for the synthesized 4EGI-1 derivatives, 7:

| | | | | HPLC | | | SRB-IC50 (μM) | |
|---|---|---|---|---|---|---|---|---|
| | Compound | Position | n | RT(min) | LC-MS | Yield* | 2351 | 2813 |
| 1 | KH146-f | p- | 2 | 18.411$^a$ | Calc: 506.01 (100.0%), 504.01 (96.8%). Found M+: 506.85 (100.0%), 504.83 (96.8%) | 26% | <0.54 | 2.1 |
| 2 | KH146-s | p- | 2 | 20.378$^a$ | Calc: 506.01 (100.0%), 504.01 (96.8%). Found M+: 506.85 (100.0%), 504.83 (96.8%) | | 14.5 | 14.0 |
| 3 | KH147-f | p- | 3 | 17.499$^b$ | Calc: 520.02 (100.0%), 518.03 (98.2%). Found M+: 520.91 (100.0%), 518.89 (96.8%) | 35% | 0.5 | 1.1 |
| 4 | KH147-s | p- | 3 | 19.872$^b$ | Calc: 520.02 (100.0%), 518.03 (98.2%). Found M+: 520.91 (100.0%), 518.969 (96.8%) | | 11.2 | 5.5 |
| 5 | KH112 | p- | 4 | 10.326, 11.806$^c$ | Calc: 534.04 (100.0%), 532.04 (97.7%). Found M+: 535.10 (100.0%), 533.01 (97.7%) | 85% | | |

-continued

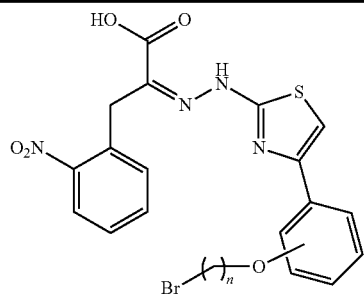

| | Compound | Position | n | HPLC RT(min) | LC-MS | Yield* | SRB-IC50 (µM) 2351 | 2813 |
|---|---|---|---|---|---|---|---|---|
| 6 | KH148 | p- | 5 | 11.614, 13.478[c] | Calc: 548.06 (100.0%), 546.06 (98.1%). Found M+: 549.20 (100.0%), 547.16 (98.1%). | 45% | <0.54 | 0.8 |
| 8 | KH149-f | o- | 2 | 8.597[c] | Calc: 506.01 (100.0%), 504.01 (96.8%). Found M+: 507.04 (100.0%), 505.02 (96.8%). | 20% | 1.0 | 1.0 |
| 9 | KH149-s | o- | 2 | 9.442[c] | Calc: 506.01 (100.0%), 504.01 (96.8%). Found M+: 506.98 (100.0%), 504.96 (96.8%). | | 6.0 | 11.5 |
| 10 | KH150 | o- | 3 | 9.143, 10.466[c] | Calc: 520.02 (100.0%), 518.03 (98.2%). Found M+: 521.04 (100.0%), 519.02 (98.2%). | 42% | 2.8 | 0.9 |
| 11 | KH151 | o- | 4 | 12.974, 14.974[c] | Calc: 534.04 (100.0%), 532.04 (97.7%). Found M+: 535.03 (100.0%), 533.03 (97.7%). | 60% | | |
| 12 | KH152-f | o- | 5 | 9.943[c] | Calc: 548.06 (100.0%), 546.06 (98.1%). Found M+: 549.06 (100.0%), 547.06 (98.1%). | 60% | 2.4 | <1.0 |
| 13 | KH152-s | o- | 5 | 11.943[c] | Calc: 548.06 (100.0%), 546.06 (98.1%). Found M+: 549.09 (100.0%), 547.09 (98.1%). | | 7.8 | 4.5 |
| 14 | KH153-f | m- | 2 | 8.461[c] | Calc: 506.01 (100.0%), 504.01 (96.8%). Found M+: 507.23 (100.0%), 505.23 (96.8%) | 63% | 13.2 | 8.0 |
| 15 | KH153-s | m- | 2 | 9.951[c] | Calc: 506.01 (100.0%), 504.01 (96.8%). Found M+: 507.23 (100.0%), 505.23 (96.8%) | | 14.0 | |
| 16 | KH154-f | m- | 3 | 9.770[c] | Calc: 520.02 (100.0%), 518.03 (98.2%). Found M+: 521.16 (100.0%), 519.21 (98.2%). | 42% | 3.5 | 0.7 |
| 17 | KH154-s | m- | 3 | 11.291[c] | Calc: 520.02 (100.0%), 518.03 (98.2%). Found M+: 521.16 (100.0%), 519.21 (98.2%). | | 1.5 | |
| 18 | KH155 | m- | 4 | 10.331, 11.182[d] | Calc: 534.04 (100.0%), 532.04 (97.7%). Found M+: 535.10 (100.0%), 533.01 (97.7%). | 30% | 8.6 | 10.8 |
| 19 | KH156 | m- | 5 | 13.495, 16.007[d] | Calc: 548.06 (100.0%), 546.06 (98.1%). Found M+: 549.16 (100.0%), 547.16 (98.1%). | 80% | 9.1 | 6.0 |
| | 4EGI-1 | | | | | | 6.5 | 1.3 |

*Isolated Yield,
[a]30 to 70 ACN/DDW in 25 min,
[b]40 to 70 ACN/DDW in 25 min,
[c]50 to 70 ACN/DDW in 25 min,
[d]50 to 100 ACN/DDW in 25 min General Procedure for the Synthesis of 8: 1 mmol of the previously prepared 7 was dissolved in 2 ml of methanol. Then 2 equiv of sodium azide were added and the reaction was refluxed for 18 hrs. And then solvent evaporated to dryness. The product was purified using reversed phase column chromatography using gradient increase of methanol percentage in DDW-0.1% formic acid.

Table 5 includes experimental data for the synthesized 4EGI-1 derivatives with the following general structure, 8:

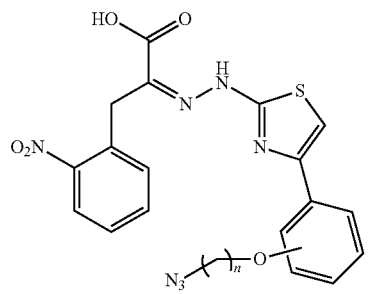

| | Compound | Position | n | HPLC RT(min)$^a$ | LC-MS | Yield* | SRB-IC50 (μM) 2351 | 2813 |
|---|---|---|---|---|---|---|---|---|
| 1 | KH166-f | p- | 2 | 9.070 | Calc: 467.10. Found M+: 468.01. | 58% | 5.0 | 9.0 |
| 2 | KH167-f | p- | 3 | 10.155 | Calc: 481.12. Found M+: 482.07 | 73% | NA | 18.6 |
| 3 | KH167-s | p- | 3 | 10.378 | Calc: 481.12. Found M+: 482.07 | | 2.8 | 11.9 |
| 4 | KH113-f | p- | 4 | | Calc: 495.13. Found M+: 496.01 | 75% | 2.1 | 1.5 |
| 5 | KH113-s | p- | 4 | 11.293 | Calc: 495.13. Found M+: 496.01 | | 11.0 | 12.5 |
| 6 | KH168-f | p- | 5 | 11.016 | Calc: 509.15. Found M+: 510.07 | 78% | 2.4 | 3.1 |
| 7 | KH168-s | p- | 5 | 12.866 | Calc: 509.15. Found M+: 510.07 | | NA | 16.0 |
| 8 | KH169 | o- | 2 | 8.005, 10.435 | Calc: 467.10. Found M+: 468.01. | 78% | 2.9 | 3.2 |
| 9 | KH170 | o- | 3 | 7.161, 9.860 | Calc: 481.12. Found M+: 482.14. | 58% | 0.8 | 16.5 |
| 10 | KH172 | o- | 5 | 12.360 | Calc: 509.05. Found M+: 510.13 | 64% | 0.54 | 0.9 |
| 12 | KH174 | m- | 2 | 9.829 | Calc: 467.10. Found M+: 468.08. | 65% | 1.3 | 11.0 |
| | 4EGI-1 | | | | | | 6.5 | 1.3 |

*Isolated Yield,
$^a$30 to 70 ACN/DDW in 25 min.

General Procedure for the Synthesis of 9: 1 mmol of 8 was dissolved in 2 ml of acetonitrile, then 1 ml of tert-butanol was added. 50 μL of diisopropylamine was added. Then 1.2 equiv of 3 were added followed by 0.33 equivalents of CuI (and the reaction stirred for overnight at room temperature. Then solvent evaporated partially and 5 ml of DDW were added, a precipitate usually forms and if not then solvent evaporated to dryness. The product was purified using reversed phase column chromatography using gradient increase of methanol percentage in DDW-0.1% formic acid.

Table 6 includes experimental data for the synthesized 4EGI-1 derivatives with the following general structure 9:

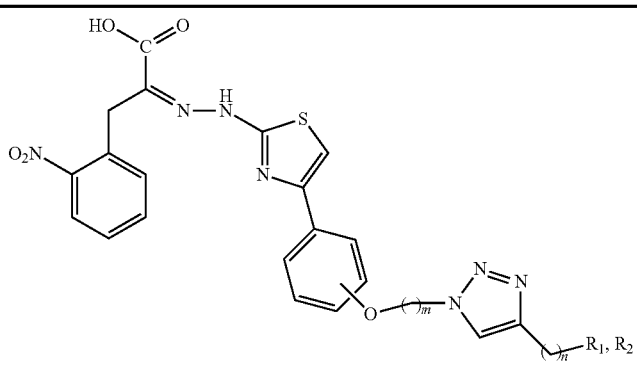

R₁ = Am
R₂ = O-CH₂CH₂-Am
m = 2, 3, 4 and 5
n = 1, 3 and 5
Am = NH₂, NMe₂ and
NH—C(=NH)—NH₂

|   | Compound | Position | m | n | R | Am | HPLC RT(min)[a] | LC-MS | Yield* |
|---|----------|----------|---|---|---|----|-----------------|-------|--------|
| 1 | KH120 | p- | 4 | 1 | R₂ | NH₂ | 10.332, 10.689 | Calc: 594.20. Found M+: 595.24. | 75% |
| 2 | KH179 | p- | 3 | 1 | R₁ | NH₂ | 8.140, 8.865 | Calc: 536.16. Found M+: 537.24. | 20% |
| 3 | KH180 | p- | 4 | 1 | R₁ | NH₂ | 8.793, 15.160 | Calc: 550.17. Found M+: 551.30. | 50% |
| 4 | KH181 | p- | 5 | 1 | R₁ | NH₂ | 9.580, 16.649 | Calc: 564.19. Found M+: 564.23. | 35% |
| 5 | KH183 | P- | 3 | 1 | R₂ | NMe₂ | 9.116 | Calc: 608.22. Found M+: 609.24. | 55% |
| 6 | KH117 | p- | 4 | 1 | R₂ | NMe₂ | 10.832, 11.054 | Calc: 622.23. Found M+: 623.24 | 60% |
| 7 | KH185 | p- | 5 | 1 | R₂ | NMe₂ | 10.913, 11.054 | Calc: 636.25. Found M+: 637.30 | 56% |
| 8 | KH189 | p- | 3 | 1 | R₁ | NMe₂ | 8.140, 8.865 | Calc: 564.19. Found M+: 565.17 | 60% |
| 9 | KH190 | p- | 4 | 1 | R₁ | NMe₂ | 8.684, 9.278 | Calc: 578.21. Found M+: 579.17 | 62% |
| 10 | KH191 | p- | 5 | 1 | R₁ | NMe₂ | 9.532, 9.901 | Calc: 592.22, Found M+: 593.16 | 65% |

*Isolated Yield,
[a] 30 to 100 in 25 min ACN/DDW

EXAMPLE VII

Synthesis of Oxazole Compounds

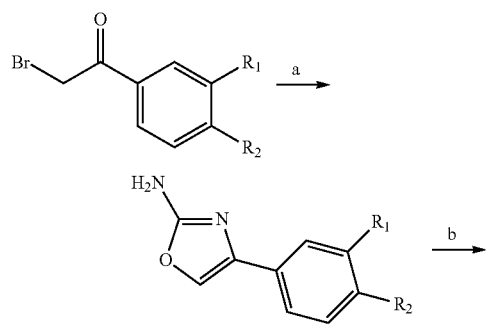

RYF-330 R₁ = R₂ = Cl, Mw = 229.06
RYF-358 R₁ = H, R₂ = OMe, Mw = 190.20
RYF-381 R₁ = H, R₂ = H, Mw = 160.17

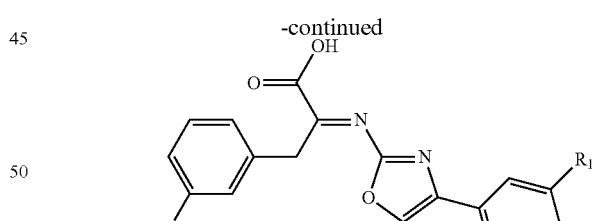

RYF-341 R₁ = R₂ = Cl, Mw = 420.20
RYF-359 R₁ = H, R₂ = OMe, Mw = 381.84
RYF-382 R₁ = H, R₂ = H, Mw = 351.31 a. Urea, acetonitrile, reflux, overnight
b. 3-(3-nitrophenyl)-2-oxopropanoic acid, 5% Acetic acid in ethanol General Procedure for the Preparation of 2-amino-oxazoles: 2-bromoacetophenone (2.18 mmole) and urea (10 eq) were refluxed overnight in acetonitrile (25 ml). The reaction mixture was cooled, the solvent evaporated and the residue purified on silica gel using mixture of ethyl acetate/hexane (3:7). Yields (70% RYF-330, 94% RYF-358, 85% RYF-381). RYF-330 (methanol-d₄, 600 MHz) ¹H-nmr δ=7.79 (d, J=2.4

Hz, 1H), 7.71 (s, 1H), 7.53 (dd, J=7.8, 2.4 Hz, 1H), 7.48 (d, J=7.8 Hz, 1H). $^{13}$C-nmr: RYF-358 (methanol-d$_4$, 600 MHz) $^1$H-nmr δ=7.52 (dt, J=9.0, 2.4 Hz, 2H), 7.49 (s, 1H), 6.91 (dt, J=9.0, 2.4 Hz, 2H), 3.79 (s, 3H).

General Procedure for the Preparation of 3-nitrophenyl-2-(4-phenyloxazol-2-ylimino)-propanoic acids 2-amino-oxazole and 3-(3-nitrophenyl)-2-oxopropanoic acid: (2 eq) were stirred overnight at 50 C in a mixture of 5% acetic acid in ethanol. After evaporation of the solvents the residue was loaded on RP Biotage and eluted with a gradient of 50 to 20% methanol in water. The relevant fractions were collected and evaporated to give a moderate yield of orange powder. RYF-341 (DMSO-d$_6$, 600 MHz) $^1$H-nmr δ=13.25 (bs, 1H), 8.13 (dd, J=8.4, 1.2 Hz, 1H), 7.32 (dt, J=7.8, 1.2 Hz, 1H), 7.66 (d, J=1.8 Hz, 1H), 7.60 (dd, J=8.4 Hz, 1H), 7.59 (dt, J=7.8, 1.2 Hz, 1H), 7.47 (dd, J=8.4, 2.4 Hz, 1H), 7.46 (d, J=7.8 Hz, 1H), 7.36 (s, 1H), 3.3 (s, 2H). $^{13}$C-nmr: 167.0, 161.4, 147.7, 136.6, 136.3, 134.5, 133.8, 132.2, 131.7, 131.2, 131.1, 131.0, 130.9, 130.0, 129.5, 127.9, 126.0, 125.3, 41.1. RYF-359 (methanol-d$_4$, 600 MHz) $^1$H-nmr δ=8.11 (dd, J=8.4, 1.2 Hz, 1H), 7.62 (dt, J=7.8, 1.2 Hz, 1H), 7.52 (dt, J=7.8, 1.2 Hz, 1H), 7.48 (dd, J=7.8, 1.2 Hz, 1H), 7.42 (d, J=9.0 Hz, 2H), 7.35(s, 1H), 6.90 (d, J=8.4 Hz, 2H), 3.78 (s, 2H). RYF-382 (DMSO-d$_6$, 600 MHz) $^1$H-nmr δ=13.25 (bs, 1H), 8.13 (dd, J=8.4, 1.2 Hz, 1H), 7.32 (dt, J=7.8, 1.2 Hz, 1H), 7.66 (d, J=1.8 Hz, 1H), 7.60 (dd, J=8.4 Hz, 1H), 7.59 (dt, J=7.8, 1.2 Hz, 1H), 7.47 (dd, J=8.4, 2.4 Hz, 1H), 7.46 (d, J=7.8 Hz, 1H), 7.36 (s, 1H), 3.3 (s, 2H). $^{13}$C-nmr: 167.0, 161.4, 147.7, 136.6, 136.3, 134.5, 133.8, 132.2, 131.7, 131.2, 131.1, 131.0, 130.9, 130.0, 129.5, 127.9, 126.0, 125.3, 41.1.

EXAMPLE VIII

Synthesis of C4-C5 Thiazolyl Fused Mimetics of 4EGI-1

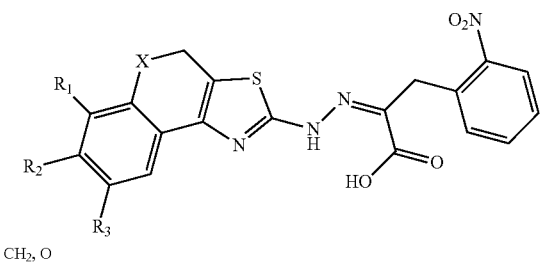

X = CH$_2$, O

Scheme 1: 2-(2-(7,8-dichloro-4,5-dihydronaphtho[1,2-d]thiazol-2-yl)hydrazono)-3-(2-nitrophenyl) propanoix acid (PC159):

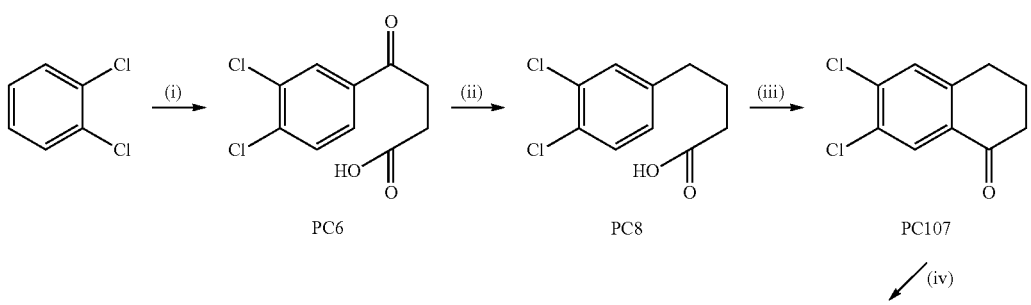

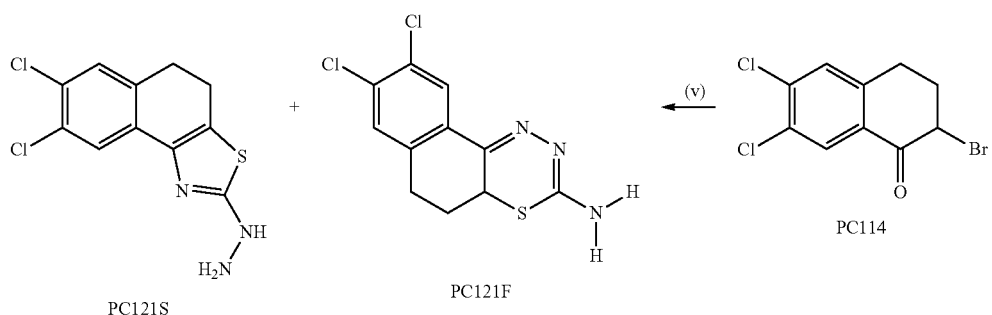

 (vi) 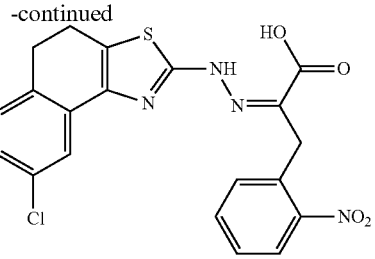

PC121S → PC159F

Reagents and Conditions:
(i) Succinic anhydride, Aluminium Chloride, 65° C., 4 h, 80%
(ii) Zn—Hg, Con. HCl, Toluene, reflux, 36 h, 30%
(iii) Polyphosphoric acid, 130° C., 12 h, 20%
(iv) Bromine, Ether, 30 min, 90%
(v) Thiosemicarbazide, Dioxane, 48 h, 52%
(vi) 2-Nitrophenylpyruvic acid, 5% Acetic acid-Ethanol (1:2), reflux, 1 h. 38%

Synthesis of 4-(3,4-Dichlorophenyl-1-oxo-butyric acid (PC6): Procedure: Aluminium chloride (19.9 g, 0.15 mol) was added to a solution of succinic anhydride (5 g, 0.05 mol) in 1,2-dichlorobenzene (44.1 g, 0.03 mol) at ambient temperature. The reaction was heated to 60° C. for 2.5 h them inverse quenched onto cold water (120 ml) maintaining the temperature less than 50° C. and stirred for 30 minutes. Then 60 ml of hexane was added and the stirring continued for 2 hrs to afford a off white solid. The compound 4-(3,4-Dichlorophenyl)-1-oxo-butyric acid was filtered and dried at the pump for twelve hours. The product was analyzed by LCMS. The LCMS analysis showed the formation of the required compound (m/e: 247.01).

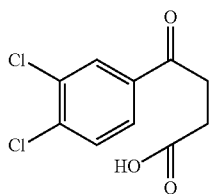

PC06

PC06: White powder, Yield: 59.3 g (80%); $^1$H NMR (DMSO-$d_6$, 400 MHz) in ppm: δ 2.54-2.57 (t, 2H), 3.24 (t, 2H), 7.79 (d, J=8 Hz, 1H), 7.90-7.93 (dd, J=8 Hz and 4 Hz, 1H), 8.12 (d, J=4 Hz, 1H); $^{13}$C NMR (DMSO-$d_6$, 100 MHz) in ppm: δ 28.4, 33.9, 128.6, 130.4, 131.7, 136.6, 137.2, 174.3, 197.5; ESI-MS (MW calcd. 247.01) m/z=248.82 (M−H)$^+$.

Synthesis of 4-(3,4-Dichlorophenyl)butyric acid (PC08): Procedure: Pure Zn dust (98%) (2.6 g) 0.04 mol and Mercuric Chloride, 0.180 g (0.66 mmol) were stirred with 0.25 ml of Con. HCl and 0.5 ml of water for 10 minutes. The aqueous solution was then syringed out leaving amalgamated zinc as a solid melt. To this material were added 4 ml of water and 8 ml of Con. HCl. To this stirred suspension was added 4 mmole (1 g) of 4-(3,4-Dichlorophenyl)-1-oxo-butyric acid followed by 8 ml of toluene. The reaction mixture was then refluxed with stirring for 36 hours with the addition of 4 ml of Con. HCl for in each 5 hours interval. The reaction mixture was cooled to room temperature and filtered. The reaction mixture was partitioned by extraction with ethyl acetate. The ethyl acetate layer was dried and concentrated to give the butyric acid derivative as oil. It was then column chromatographed using, Hexane-Ethyl acetate mixture as eluent. The LCMS analysis of the product showed the required mass, m/e: 232.98

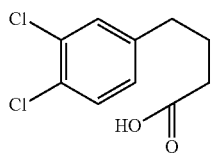

PC08

PC08: White solid, Yield: 0.28 g (30%); $^1$H NMR (CDCl$_3$, 400 MHz) in ppm: δ 1.91-1.97 (m, 2H), 2.35-2.39 (t, 2H), 2.61-2.64 (t, 2H), 7.00-7.02 (dd, J=8 Hz and 4 Hz, 1H), 7.26 (d, J=4 Hz, 1H), 7.34 (d, J=8 Hz, 1H); $^{13}$C NMR (CDCl$_3$, 100 MHz) in ppm: δ 26.0, 33.3, 34.2, 123.2, 125.7, 128.1, 130.5, 131.8, 141.6, 179.9; ESI-MS (MW calcd. 232.98) m/z=233.00 (M−H)$^+$.

Synthesis of 6,7-dichloro tetralone (PC107): Procedure: Polyphosphoric acid (35 g) was heated to melt at 120° C. for 30 minutes. To this was added 1.2 g (5.1 mmol) 4-(3,4-dichlorophenyl)butanoic acid (PC08) and this mixture was heated further with stirring for 10 h at 130° C. LCMS analysis showed the formation of the product and the disappearance of starting material. The reaction mixture was then cooled and water (100 ml) was added. It was then extracted with ethylacetate (100 ml) and then was washed with saturated Sodium bicarbonate (50 ml). The organic phase was dried and evaporated in vacuum. The oily residue was subjected to column chromatography with Hexane-ethylacetate (98:2) to obtain the tetralone.

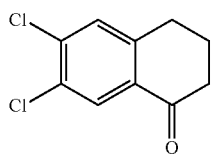

PC107

PC107: White solid, Yield: 320 mg (30%); $^1$H NMR (CDCl$_3$, 400 MHz) in ppm: δ 2.11-2.66 (m, 2H), 2.64 (t, 2H), 2.91 (t, 1H), 7.37 (s, 1H), 8.08 (s, 1H).

Synthesis of 2-bromo-6,7-dichloro tetralone: Procedure: To a solution of 100 mg (0.46 mmol) 6,7-dichloro tetralone in 5 ml of dry diethyl ether was added 0.074 g (0.024 ml, 0.46 mmol) of bromine in 1 ml of ether. The reaction mixture was stirred at rt for 30 min. LCMS analysis showed the formation of the product and the disappearance of the starting material. The solvent was then evaporated in vacuum and 5% aqueous sodium bicarbonate (10 ml) was added to the residue and was extracted with dichloromethane. The organic layer was dried and concentrated under vacuum. The residue was then column chromatographed with 5% ethyl acetate-hexane to afford the bromide.

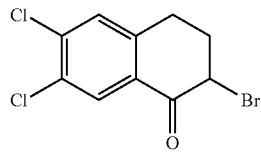

PC114

PC114: White powder, Yield: 120 mg (88%); $^1$H NMR (CDCl$_3$, 400 MHz) in ppm: δ 2.83-2.88 (m, 2H), 3.22-3.29 (m, 2H), 4.69 (t, 1H), 7.40 (s, 1H), 8.12 (s, 1H); $^{13}$C NMR (CDCl$_3$, 100 MHz) in ppm: δ 25.4, 31.4, 49.2, 129.6, 130.5, 130.8, 132.1, 138.8, 142.3, 188.8.

Synthesis of 8,9-dichloro-5,6-dihydro-4aH-naphtho[1,2-e][1,3,4]thiadiazin-3-amine (PC 121F) and 1-(7,8-dichloro-4,5-dihydronaphtho[1,2-d]thiazol-2-yl)hydrazine (PC121S): Procedure: A solution of 400 mg (1.36 mmol) of 2-bromo-6,7-dichloro-3,4-dihydronaphthalen-1(2H)-one and thiosemicarbazide (124 mg, 1.36 mmol) in 20 ml of anhydrous dioxane was heated to 80 C for 1 h and then stirred at room temperature for 48 hours. The resulting precipitate was filtered and washed with dioxane (10 ml). The dried precipitate was then basified with 2 M Sodium Carbonate (15 ml) solution. The formed pale greenish yellow product was filtered at the pump and washed with water. The LCMS analysis showed the formation of the required 1-(7,8-dichloro-4,5-dihydronaphtho[1,2-d]thiazol-2-yl)hydrazine (PC121S) m/e=286.18, along with 8,9-dichloro-5,6-dihydro-4aH-naphtho[1,2-e][1,3,4]thiadiazin-3-amine (PC121F), m/e=286.18. These two products were isolated by preparative HPLC.

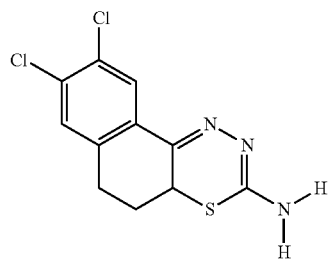

PC121F

PC121F: Pale pinkish solid, Yield: 50 mg (13%); $^1$H NMR (DMSO-d$_6$, 400 MHz) in ppm: δ 1.73-1.84 (m, 2H), 2.77-2.95 (m, 2H), 4.31-4.35 (m, 1H), 7.66 (s, 1H), 8.05 (s, 1H); $^{13}$C NMR (DMSO-d$_6$, 100 MHz) in ppm: δ 25.8, 27.1, 34.3, 127.0, 129.2, 130.5, 131.4, 134.3, 141.6, 148.0, 164.4.

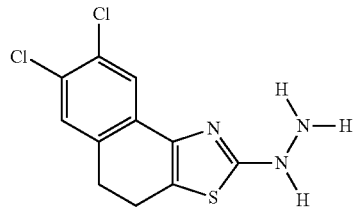

PC121S

PC121S: Dull white solid, Yield: 150 mg (39%); $^1$H NMR (DMSO-d$_6$, 400 MHz) in ppm: δ 2.86-2.95 (m, 4H), 7.49 (s, 1H), 7.67 (s, 1H), 9.27 (bs, 2H).

Synthesis of 2-(2-(7,8-dichloro-4,5-dihydronaphtho[1,2-d]thiazol-2-yl)hydrazono)-3-(2-nitrophenyl)propanoic acid (PC159F and PC159S): Procedure: A suspension of 1-(7,8-dichloro-4,5-dihydronaphtho[1,2-d]thiazol-2-yl)hydrazine, 186 mg (0.649 mmol) in 7 mL of 5% acetic acid was added to 2-nitro phenyl pyruvic acid (135 mg, (0.649 mmol) in 14 mL ethanol. The resulting mixture was refluxed for 1 h at 90-100° C. The two isomers, PC159F and PC159S were purified by reverse phase silica gel column chromatography from 300 mg of the crude mixture using Triethylammonium bicarbonate buffer (50 mmol) and methanol as eluent system. The respective fractions for each isomer were acidified with 10% HCl and the products were precipitated. The solids were centrifuged and repeatedly washed with 5% HCl, filtered and dried.

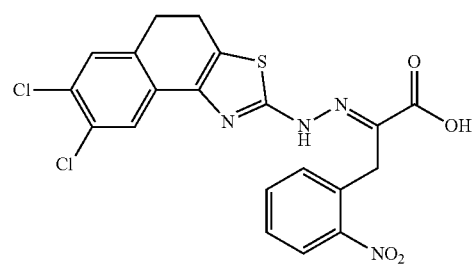

PC159F

Yellow powder. Yield: 60 mg (20%). M.P: 255-256° C.; $^1$H NMR (DMSO-d$_6$, 400 MHz) in ppm: δ 2.85-2.89 (m, 2H), 2.93-2.97 (m, 2H), 4.27 (s, 2H), 7.05 (d, J=8.0 Hz, 1H), 7.47-7.51 (m, 2H), 7.55 (s, 1H), 7.60-7.65 (m, 1H), 8.04-8.06 (m, 1H), 12.44 (bs, 1H); $^{13}$C NMR (DMSO-d$_6$, 100 MHz) in ppm: δ 21.3, 27.7, 29.8, 123.6, 125.7, 128.5, 129.2, 129.5, 129.7, 130.5, 131.7, 134.5, 136.0, 149.6, 166.0; RP-HPLC on a C18 Xbridge column (4.6×100 mm, 1 mL/min), t$_R$=8.37 min, purity of 100%, employing a linear gradient system of acetonitrile-water: 50%-100% B in A for 20 min. Where A is 0.1% Trifluoroacetic acid in water and B is 0.1% Trifluoroacetic acid in acetonitrile. HRMS (ESI) calcd for: MW 476.01128. Found: m/z=477.01951 [M+H]$^+$.

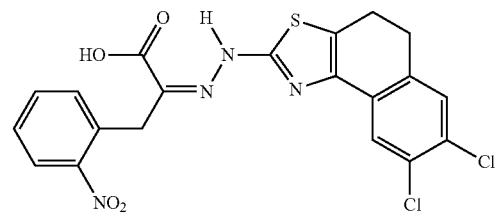

PC159S

Yellow powder. Yield: 55 mg (18%). 254-255° C.; $^1$H NMR (DMSO-d$_6$, 400 MHz) in ppm: δ 2.73-2.80 (m, 2H), 2.88-2.92 (m, 2H), 4.15 (s, 2H), 7.46-7.55 (m, 3H), 7.59 (s, 1H), 7.66-7.70 (m, 1H), 8.02-8.05 (m, 1H), 12.72 (bs, 1H); $^{13}$C NMR (DMSO-d$_6$, 100 MHz) in ppm: δ 21.2, 27.7, 36.7, 123.3, 125.2, 128.9, 129.3, 129.8, 130.4, 132.5, 133.60, 134.2, 135.9, 149.7, 164.7; RP-HPLC on a C18 Xbridge column (4.6×100 mm, 1 mL/min), t$_R$=8.23 min, purity of 99.24%, employing a linear gradient system of acetonitrile-water: 50%-100% B in A for 20 min. Where A is 0.1% Trifluoroacetic acid in water and B is 0.1% Trifluoroacetic acid in acetonitrile. HRMS (ESI) calcd for: MW 476.01128. Found: m/z=477.01929 [M+H]$^+$.

to the n-butyl lithium solution for the period of 10 minutes with keeping the temperature below –78° C. The mixture was stirred for half an hour to form a pale yellow color. Then a solution of succinic anhydride 1 g (0.01 mol) in 10 ml THF Scheme 2: Synthesis of 2-(2-(6,7-dichloro-4,5-dihydronaphtho[1,2-d]thiazol-2-yl)hydrazono)-3-(2-nitrophenyl)propanoic acid (PC163):

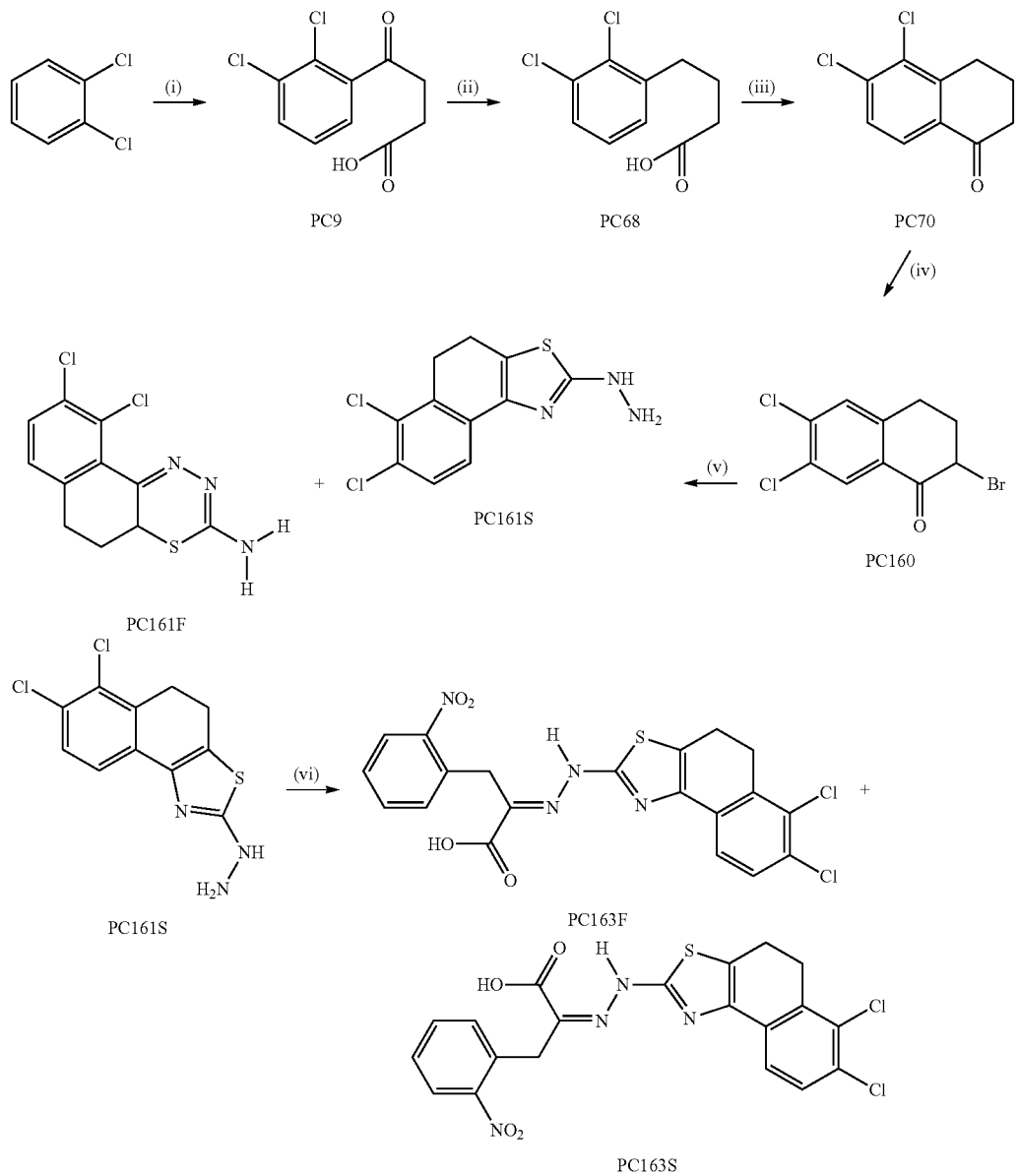

Reagents and Conditions:
(i) Succinic anhydride, n-Butyl Lithium, -78° C., 4 h, 30%
(ii) Zn—Hg, Con. HCl, Toluene, reflux, 24 h, 55%
(iii) Polyphosphoric acid, 130° C., 12 h, 30%
(iv) Bromine, Ether, 30 min, 90%
(v) Thiosemicarbazide, Dioxane, 48 h, 55%
(vi) 2-Nitrophenylpyruvic acid, 5% Acetic acid-Ethanol (1:2), reflux, 1 h.

Synthesis of 4-(2,3-Dichlorophenyl)butyric acid (PC09): Procedure: In a 100 ml three necked RB flask equipped with a nitrogen gas inlet and an additional funnel, was taken 4 ml of n-butyl lithium (4 ml, 1.8 M in hexanes). Then 10 ml of dry THF was added and the reaction mixture was kept in –80° C. for 0.5 h. A solution of orthodichlorobenzene (0.01 mol, 1.47 g) in 10 ml THF was added in drops by the additional funnel was added slowly for the period of 15 minutes. As the addition continued the reaction mixture turned to yellow color. After one hour water 20 ml was added to quench the reaction and acidified with 5 N HCl. It was then extracted with DCM. The organic layer was dried and evaporated to give the required product as oil which was recrystallized from toluene. LCMS analysis revealed the formation of the product. m/e: 246.98

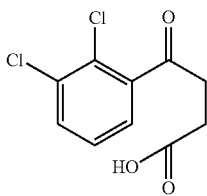

PC09

PC09: pale yellow solid, Yield: 0.74 g (30%); $^1$H NMR (CDCl$_3$, 400 MHz) in ppm: δ 2.81 (t, 2H), 3.20 (t, 2H), 7.25-7.29 (m, 1H), 7.34-7.36 (m, 1H), 7.53-7.55 (m, 1H); $^{13}$C NMR (CDCl$_3$, 100 MHz) in ppm: δ 28.4, 37.6, 126.9, 127.9, 132.5, 134.3, 141.4, 178.7, 200.8.

Synthesis of 4-(2,3-dichlorophenyl)butanoic acid (PC68): Procedure: Pure Zn dust (98%) (4 g) and Mercuric Chloride, 0.4 g were stirred with 0.2 ml of Con. HCl and 6.6 ml of water for 10 minutes. The aqueous solution was then syringed out leaving amalgamated zinc as a solid melt. To this material were added 2.5 ml of water and 6 ml of Con. HCl and 3.5 ml toluene. To this stirred solution was added 0.009 mole (2.3 g) of 4-(3,4-Dichlorophenyl)-1-oxo-butyric acid. The reaction mixture was then refluxed for 24 hours with the addition of Con. HCl, (2 ml) for every 6 hrs. The reaction mixture was cooled to room temperature and filtered. The reaction mixture was partitioned by extraction with ethyl acetate. The ethyl acetate layer was dried and concentrated to give the butyric acid as a white solid. The LCMS analysis of the product showed the required mass, m/e: 233.03.

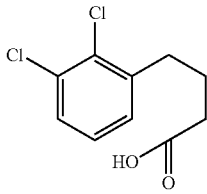

PC68

PC68: white solid, Yield: 1.2 g (57%).

Synthesis of 5,6-dichloro-3,4-dihydronaphthalen-1(2H)-one (PC70): Procedure: Polyphosphoric acid (35 g) was heated to melt at 120 C for 30 minutes. To this was added 1.2 g (5.1 mmol) 4-(2,3-dichlorophenyl)butanoic acid (PC68) and this mixture was heated further with stirring for 10 h at 130 C. LCMS analysis showed the formation of the product and the disappearance of starting material. The reaction mixture was then cooled and water (100 ml) was added. It was then extracted with ethylacetate (100 ml) and then was washed with Saturated Sodium bicarbonate (50 ml). The organic phase was dried and evaporated in vacuum. The oily residue was subjected to column chromatography with Hexane-ethylacetate (98:2) to obtain the tetralone as a yellow solid.

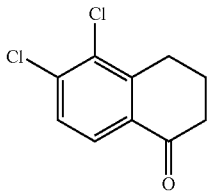

PC70

PC70: pale yellow solid, Yield: 320 mg (30%); $^1$H NMR (CDCl$_3$, 400 MHz) in ppm: δ 2.12-2.17 (m, 2H), 2.59-2.62 (t, 2H), 3.01-3.04 (t, 2H), 7.38 (d, J=8.0 Hz, 1H), 7.86 (d, J=8.0 Hz, 1H); $^{13}$C NMR (CDCl$_3$, 100 MHz) in ppm: δ 22.3, 28.1, 38.0, 126.4, 128.4, 128.5, 132.6, 138.5, 143.9, 196.7.

Synthesis of 2-bromo-5,6-dichloro-3,4-dihydronaphthalen-1(2H)-one, (PC160): Procedure: To a solution of 250 mg (1.1 mmol) 6,7-dichloro tetralone in 20 ml of dry diethyl ether was added 74 mg (1 equiv, 62 microliter, 1.1 mmol) of bromine in 2 ml of ether. The reaction mixture was stirred at rt for 40 min. The LCMS analysis showed the formation of the product and the disappearance of the starting material. The solvent was then evaporated in vacuum. 5% aqueous sodium bicarbonate was (10 ml) was added to the residue and was extracted with dichloromethane. The organic layer was dried and concentrated under vacuum. The crude was sufficiently pure to be used in the next step.

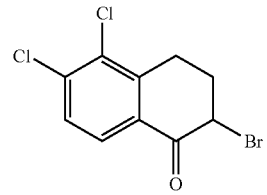

PC160

PC160: White powder, Yield: 130 mg (90%); $^1$H NMR (CDCl$_3$, 400 MHz) in ppm: δ 2.49-2.59 (m, 2H), 3.16-3.19 (m, 2H), 4.67-4.69 (m, 1H), 7.47 (d, J=8.0 Hz, 1H), 7.95 (d, J=8.0 Hz, 1H); $^{13}$C NMR (CDCl$_3$, 100 MHz) in ppm: δ 24.9, 30.6, 48.6, 127.7, 129.0, 132.5, 139.5, 142.5, 189.3.

Synthesis of 9,10-dichloro-5,6-dihydro-4aH-naphtho[1,2-e][1,3,4]thiadiazin-3-amine (PC161F) and 1-(8,9-dichloro-4,5-dihydronaphtho[1,2-d]thiazol-2-yl)hydrazine (PC161S): Procedure: A solution of 250 mg (0.85 mmol) of 2-bromo-6,7-dichloro-3,4-dihydronaphthalen-1(2H)-one and thiosemicarbazide (78 mg, 0.85 mmol) in 15 ml of anhydrous dioxane was heated to 80 C for 1 h and then stirred at room temperature for 48 hours. The resulting precipitate was filtered and washed with dioxane (10 ml). The dried precipitate was then basified with 2 M Sodium Carbonate (15 ml) solution. The formed pale greenish yellow product was filtered at the pump and washed with water. The LCMS analysis showed the formation of the required 1-(7,8-dichloro-4,5-dihydronaphtho[1,2-]thiazol-2-yl)hydrazine (PC161S) m/e=286.18, along with 8,9-dichloro-5,6-dihydro-4aH-naphtho[1,2-e][1,3,4]thiadiazin-3-amine (PC 161F), m/e=286.18.

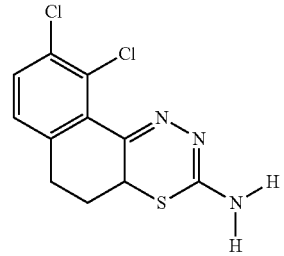

PC161F

PC161F: Off white solid, Yield: mg (%); $^1$H NMR (DMSO-d$_6$, 500 MHz) in ppm: δ 1.83-1.90 (m, 2H), 2.79-2.85 (m, 2H), 3.19-3.23 (m, 2H), 4.31-4.35 (m, 1H), 7.62 (d, J=5.0 Hz, 1H), 7.99 (d, J=5.0 Hz, 1H); $^{13}$C NMR (DMSO-d$_6$, 125 MHz) in ppm: δ 25.5, 26.1, 34.0, 125.6, 129.5, 129.7, 131.6, 135.1, 140.6, 148.5.

PC161S

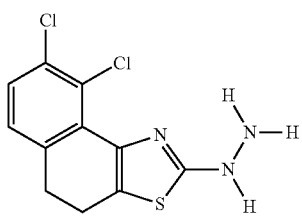

PC163F

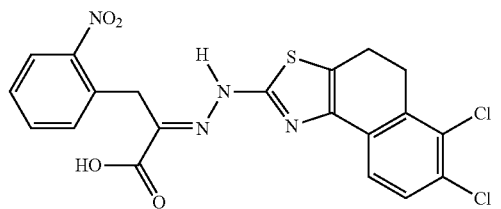

PC161S: Dull white solid; $^1$H NMR (DMSO-d$_6$, 400 MHz) in ppm: δ 2.88-2.95 (m, 2H), 3.09-3.15 (m, 2H), 7.53 (d, J=8.0 Hz, 1H), 7.61 (d, J=8.0 Hz, 1H), 9.74 (bs, 2H); $^{13}$C NMR (DMSO-d$_6$, 100 MHz) in ppm: δ 20.9, 26.7, 122.6, 123.0, 129.1, 130.3, 131.0, 131.9, 134.9, 143.1, 168.2.

Synthesis of 2-(2-(6,7-dichloro-4,5-dihydronaphtho[1,2-d]thiazol-2-yl)hydrazono)-3-(2-nitrophenyl)propanoic acid (PC163)

PC163F

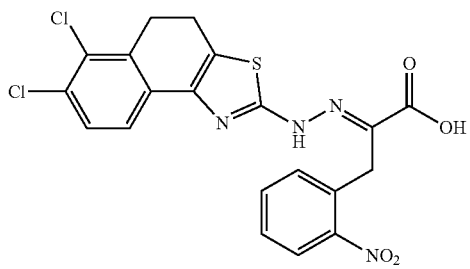

Procedure: A suspension of 1-(8,9-dichloro-4,5-dihydronaphtho[1,2-d]thiazol-2-yl)hydrazine, 130 mg (0.454 mmol) in 5 mL of 5% acetic acid was added to 2-nitro phenyl pyruvic acid (94 mg, (0.454 mmol) in 10 mL ethanol. The resulting mixture was refluxed for 1 h at 90-100° C. The reaction mixture was cooled and the precipitated yellow product was filtered and washed with water. The two isomers, PC163F and PC163S were purified by reverse phase silica gel column chromatography from 300 mg of the crude mixture using Triethylammonium bicarbonate buffer (50 mmol) and methanol as eluent system. The respective fractions for each isomer were acidified with 10% HCl and the products were precipitated. The solids were centrifuged and repeatedly washed with 5% HCl, filtered and dried.

Yellow powder. M.P: 254-255° C.; $^1$H NMR (DMSO-d$_6$, 500 MHz) in ppm: δ 2.92-2.97(m, 2H), 3.11-3.15 (m, 2H), 4.20 (s, 2H), 7.05-7.08 (m, 1H), 7.45-7.50 (m, 3H), 7.62-7.68 (m, 1H), 8.04-8.07 (m, 1H), 12.3 (bs, 1H); $^{13}$C NMR (DMSO-d$_6$, 125 MHz) in ppm: δ 20.9, 26.6, 29.8, 122.2, 125.7, 128.4, 129.1, 129.5, 130.3, 131.0, 131.8, 134.5, 135.0, 149.7, 166.1; RP-HPLC on a C18 Xbridge column (4.6×100 mm, 1 mL/min), t$_R$=8.69 min, purity of 98.74%, employing a linear gradient system of acetonitrile-water: 50%-100% B in A for 20 min. Where A is 0.1% Trifluoroacetic acid in water and B is 0.1% Trifluoroacetic acid in acetonitrile. HRMS (ESI) calcd for: MW 476.01128. Found: m/z=477.01923 [M+H]$^+$.

PC163S

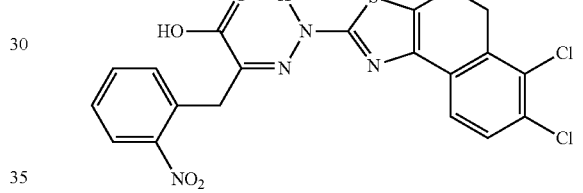

PC163S: Yellow powder. M.P: 261-262° C.; $^1$H NMR (DMSO-d$_6$, 500 MHz) in ppm: δ 2.84 (t, 2H), 3.06 (t, 2H), 4.15 (s, 2H), 7.44 (d, J=5 Hz 1H), 7.49-7.55 (m, 3H), 7.67-7.70 (m, 1H), 8.03-8.05 (m, 1H), 12.70 (bs, 1H); $^{13}$C NMR (DMSO-d$_6$, 125 MHz) in ppm: δ 20.9, 26.5, 36.7, 122.5, 125.2, 128.8, 129.0, 130.4, 130.9, 132.5, 134.1, 134.8, 149.7, 164.7; RP-HPLC on a C18 Xbridge column (4.6×100 mm, 1 mL/min), t$_R$=11.39 min, purity of 100%, employing a linear gradient system of acetonitrile-water: 50%-100% B in A for 20 min. Where A is 0.1% Trifluoroacetic acid in water and B is 0.1% Trifluoroacetic acid in acetonitrile; HRMS (ESI) calcd for: MW 476.01128. Found: m/z=477.01961 [M+H]$^+$, Scheme 3: Synthesis of 2-(2-(6,7-dichloro-4H-chromeno[4,3-d]thiazol-2-yl)hydrazono)-3-(2-nitrophenyl)propanoic acid (PC202):

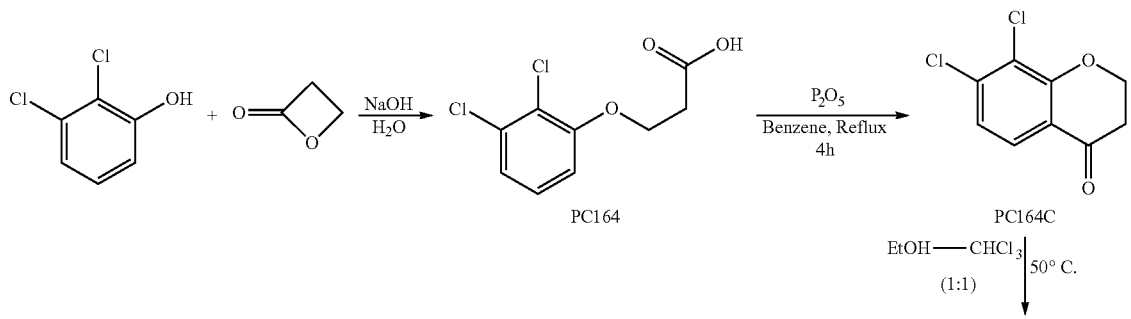

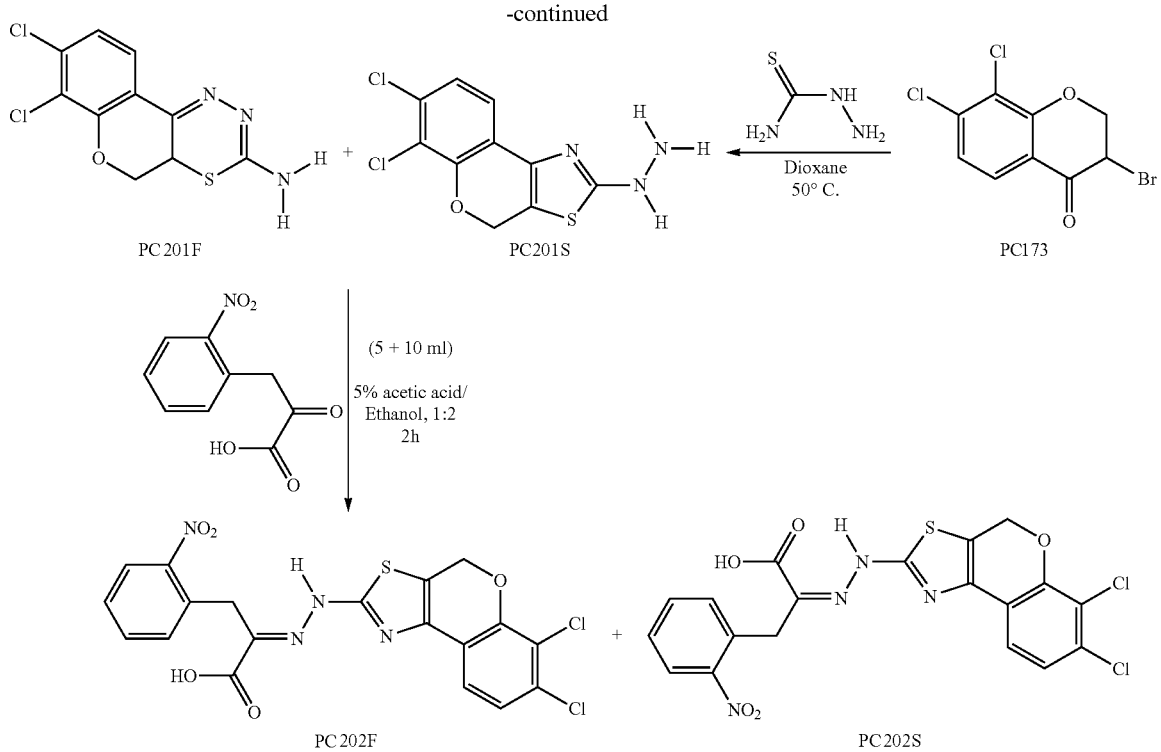

Synthesis of 3-(2,3-dichlorophenoxy)propanoic acid (PC164): Procedure: 0.4 g (0.01 mol) of Sodium hydroxide was dissolved in 4 ml of water. To this stirred solution was added 1.63 g (0.01 mol) of 2,3-dichloro phenol was added. Once the solid had dissolved the alkaline solution was kept stirring at 100 C for 1 hour. After that β-propiolactone 0.72 g (0.628 ml, 0.01 mol) was added slowly in drops for 5 minutes. The reaction mixture was further continued heating for 12 h. The reaction mixture was cooled to room temperature and water 10 ml was added. This diluted mixture was acidified by the addition of Con. HCl. The product was extracted twice with diethyl ether (20 ml). The ether layer was then washed with 10% Sodium bicarbonate. The aqueous layer was acidified to pH=2. The precipitated solid was filtered and dried to afford the required product 3-(2,3-dichlorophenoxy)propanoic acid.

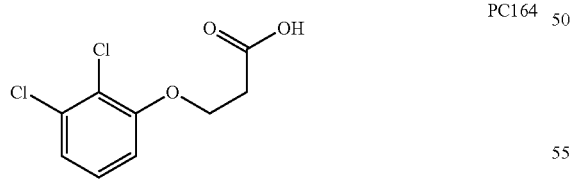

PC164

PC164: White solid, Yield: 1 g (42%); $^1$H NMR (CD$_3$OD, 400 MHz) in ppm: δ 2.00 (t, 2H), 4.28 (t, 2H), 6.98-7.00 (m, 1H), 7.06-7.08 (m, 1H), 7.17-7.21 (m, 1H); $^{13}$C NMR (CD$_3$OD, 100 MHz) in ppm: δ 33.9, 65.2, 11.6, 121.4, 122.2, 127.7, 133.3, 155.8, 173.3;

Synthesis of 7,8-dichloro-2,3-dihydrochromen-4-one (PC164C): Procedure: 500 mg of 3-(2,3-dichlorophenoxy) propionic acid, is stirred in 50 ml. of liquid hydrogen fluoride surrounded by a solid carbon dioxide/acetone bath. This slurry is allowed to stir overnight without replenishing the cooling bath. The hydrogen fluoride is removed by a stream of air. The residual solid was then dissolved in ether and washed with 10% aqueous sodium carbonate solution. The organic layer is dried over anhydrous magnesium sulphate and the solvent is evaporated to give the required chromanone with sufficient purity.

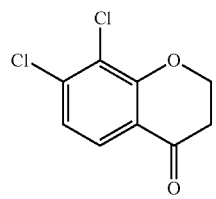

PC164C

PC164C: White solid, Yield: 350 mg (76%); $^1$H NMR (CDCl$_3$, 400 MHz) in ppm: δ 2.82 (t, 2H), 4.65 (t, 2H), 7.10 (d, J=8.0 Hz, 1H), 7.12 (d, J=8.0 Hz, 1H); $^{13}$C NMR (CDCl$_3$, 100 MHz) in ppm: δ 37.2, 68.2, 120.8, 122.0, 122.9, 125.6, 140.5, 158.5, 190.2;

Synthesis of 3-bromo-7,8-dichloro-2,3-dihydrochromen-4-one (PC173): Procedure: A mixture of 100 mg. (0.46 mmol) 7,8-dichlorochroman-4-one was dissolved in anhydrous ethanol (5 ml) and Chloroform (5 ml). To this solution was added pyridinium tribromide (0.442 g, 1.38 mmol, 3 equiv). The reddish brown mixture was heated with stirring at 50 C for 30 min. The reaction mixture was then cooled and the solvent was evaporated. Then water (20 ml) was added to the residue and it was then extracted with 20 ml of dichloromethane. The dichloromethane layer was then washed with 5% sodium bicarbonate solution followed by water (20 ml). The organic layer was then dried and the solvent was evaporated in vacuum to yield the crude product which was purified by column chromatography.

PC173

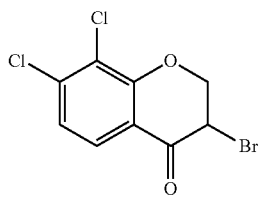

PC173: Pale yellow solid, Yield: 100 mg (74%); $^1$H NMR (CDCl$_3$, 400 MHz) in ppm: δ 4.62-4.64 (m, 1H), 4.75-4.80 (m, 1H), 7.20 (d, J=8.0 Hz, 1H), 7.79 (d, J=8.0 Hz, 1H); $^{13}$C NMR (CDCl$_3$, 100 MHz) in ppm: δ 44.0, 72.2, 118.2, 122.2, 123.9, 126.6, 141.5, 157.3, 184.0.

Synthesis of 1-(6,7-dichloro-4H-chromeno[4,3-d]thiazol-2-yl)hydrazine (PC201)

PC201F

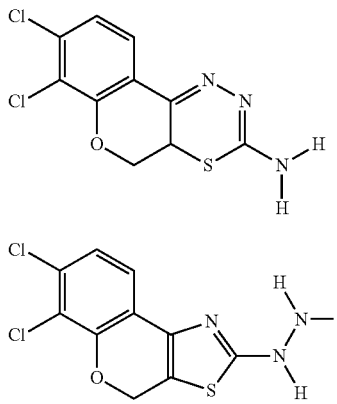

PC201S

Procedure: A solution of 200 mg (0.7 mmol) of the bromide and thiosemicarbazide (70 mg, 0.7 mmol) in 15 ml of anhydrous dioxane was stirred at 60° C. for 24 h. The resulting yellow precipitate was filtered and washed with dioxane (10 ml). The dried precipitate was then basified with 2 M sodium carbonate (20 ml) solution. The formed pale brown product was filtered at the pump and washed with water. The LCMS analysis showed the formation of the required 1-(6,7-dichloro-4H-chromeno[4,3-d]thiazol-2-yl)hydrazine along with minor amount of thiadiazine. The crude product was used as such in the next step. Yield: 80 mg Synthesis of 2-(2-(6,7-dichloro-4H-chromeno[4,3-d]thiazol-2-yl)hydrazono)-3-(2-nitrophenyl)propanoic acid (PC202): Procedure: A suspension of 1-(6,7-dichloro-4H-chromeno[4,3-d]thiazol-2-yl)hydrazine, 80 mg (0.27 mmol) in 3.5 mL of 5% acetic acid was added to 2-nitro phenyl pyruvic acid (58 mg, (0.27 mmol) in 7 mL ethanol. The resulting mixture was refluxed 1 h. The precipitated yellow product was filtered and subjected to column chromatography. LCMS analysis showed the formation of the two isomers of the product with m/e=479.29. (Ratio 65:35, crude yield: 80 mg). The product was purified by reverse-phase column chromatography, using triethylammonium bicarbonate buffer (50 mmol) and methanol as eluents.

PC202F

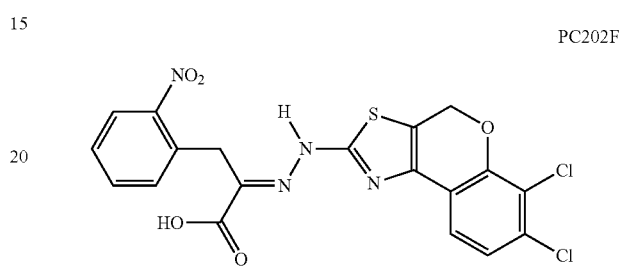

Yellow powder. $^1$H NMR (DMSO-d$_6$, 400 MHz) in ppm: δ 4.27 (s, 2H), 5.58 (s, 2H), 7.21 (d, 1H), 7.35 (d, 1H), 7.49-7.51 (m, 1H), 7.61-7.65 (m, 1H), 8.05 (d, 1H); $^{13}$C NMR (DMSO-d$_6$, 100 MHz) in ppm: δ 29.9, 66.3, 119.8, 121.4, 123.5, 125.7, 128.5, 129.5, 131.4, 131.6, 134.5, 149.6, 150.7, 165.9; RP-HPLC on a C18 Xbridge column (4.6×100 mm, 1 mL/min), t$_R$=7.03 min, purity of 98.94%, employing a linear gradient system of acetonitrile-water: 50%400% B in A for 20 min. Where A is 0.1% Trifluoroacetic acid in water and B is 0.1% Trifluoroacetic acid in acetonitrile; HRMS (ESI) calcd for: MW 477.99055. Found: m/z=479.00179 [M+H]$^+$.

PC202S

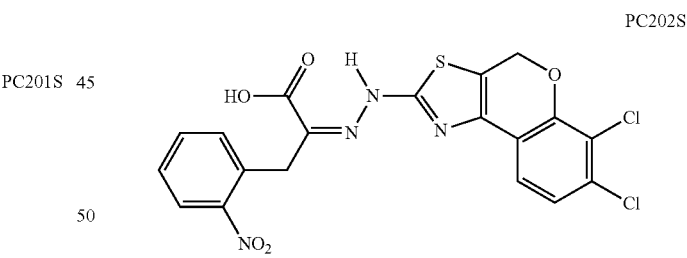

Yellow powder. $^1$H NMR (DMSO-d$_6$, 400 MHz) in ppm: δ4.17 (s, 2H), 5.47 (s, 2H), 7.18-7.20 (m, 1H), 7.40 (d, 1H, J=5 Hz), 7.51-7.56 (m, 2H), 7.68-7.71 (m, 1H), 8.05 (d, 1H, J=5 Hz), 12.72 (bs, 1H); $^{13}$C NMR (DMSO-d$_6$, 100 MHz) in ppm: δ 36.8, 66.2, 119.7, 121.8, 123.5, 125.3, 128.9, 131.5, 132.4, 133.7, 134.2, 149.6, 150.6, 164.7; RP-HPLC on a C18 Xbridge column (4.6×100 mm, 1 mL/min), t$_R$=9.22 min, purity of 99.51% employing a linear gradient system of acetonitrile-water: 50%-100% B in A for 20 min. Where A is 0.1% TFA in water and B is 0.1% TFA in acetonitrile; HRMS (ESI) calcd for: MW 477.99055. Found: m/z=479.02029 [M+H]$^+$.

Scheme 4: Synthesis of 2-(2-(7,8-dichloro-4H-chromeno[4,3-d]thiazol-2-yl)hydrazono)-3-(2-nitrophenyl)propanoic acid (PC204):

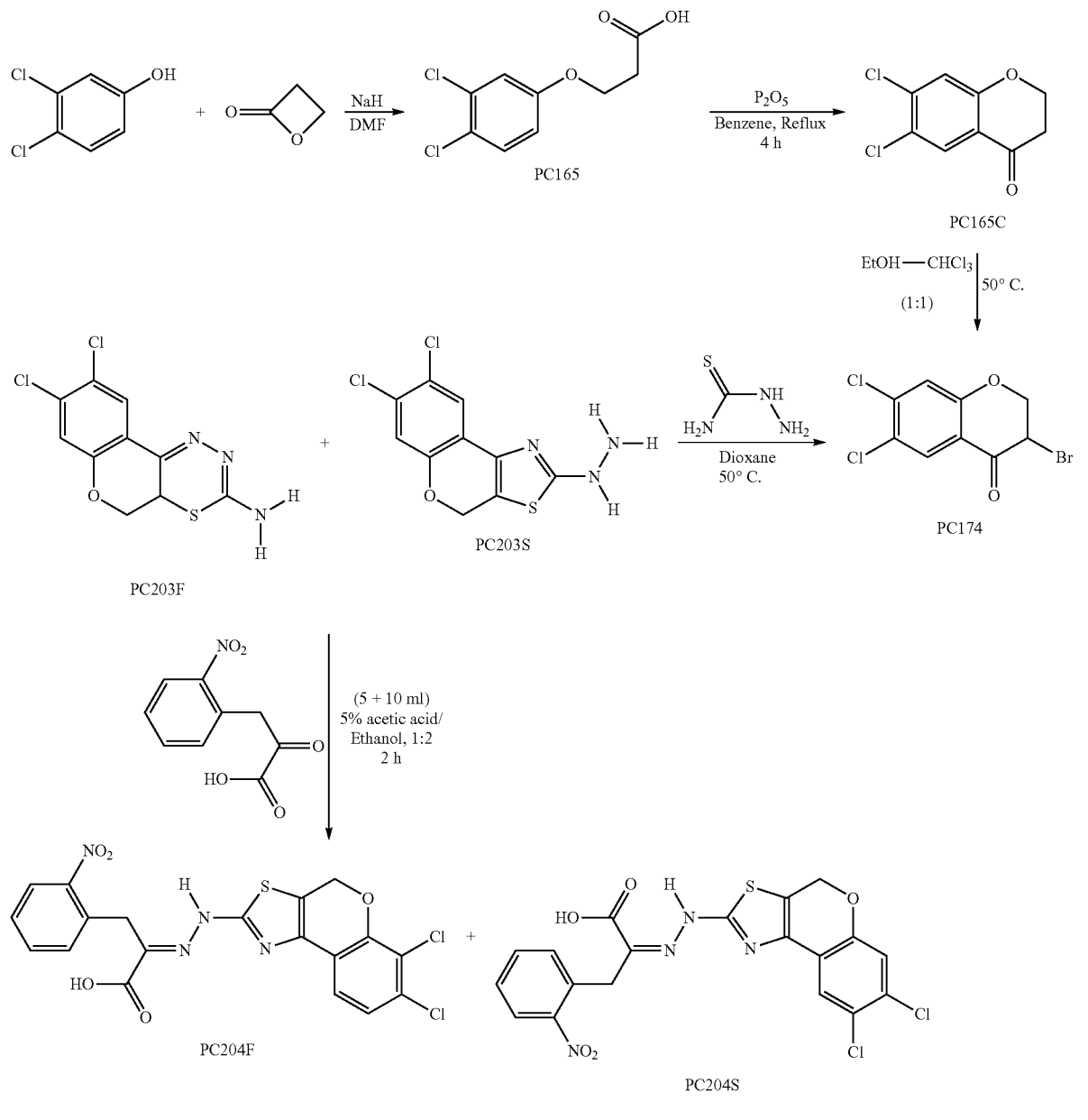

Synthesis of 3-(3,4-dichlorophenoxy)propanoic acid (PC165): Procedure: Sodium hydride 0.24 g (0.01 mol) was dissolved in 10 ml of dry DMF. After 30 min, a solution of 3,4-dichloro phenol 1.63 g (0.01 mol) dissolved in 5 ml of DMF was added in drops. The reaction mixture was heated to 100 C. After 1 hour, β-propiolactone, 0.72 g (0.628 ml, 0.01 mol) was added slowly for 5 minutes. The reaction mixture was further continued heating for 12 h. The reaction mixture was cooled to room temperature and poured over ice-cold water 10 ml was added. This diluted mixture was acidified by the addition of Con. HCl. The product was extracted twice with diethyl ether (20 ml). The ether layer was then washed with 10% Sodium bicarbonate. The aqueous layer was acidified to pH=2. The precipitated solid was filtered and dried to afford the required product 3-(3,4-dichlorophenoxy)propanoic acid (PC165).

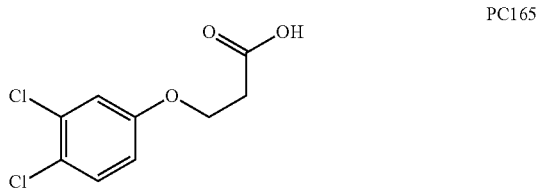 [SMILES: O=C(O)CCOc1ccc(Cl)c(Cl)c1]

PC165: White solid, Yield: 1.2 g (50%); $^1$H NMR (CD$_3$OD, 400 MHz) in ppm: δ 2.74 (t, 2H), 4.19 (t, 2H), 6.83-6.86 (m, 1H), 7.06 (d, J=4.0 Hz, 1H), 7.35 (d, J=8.0 Hz, 1H); $^{13}$C NMR (CD$_3$OD, 100 MHz) in ppm: δ 33.9, 64.3, 114.7, 116.3, 123.6, 130.6, 132.5, 158.2, 173.4;

Synthesis of 6,7-dichloro-2,3-dihydrochromen-4-one (PC165C): Procedure: 500 mg of 3-(3,4-dichlorophenoxy)

propionic acid, is stirred in 50 ml. of liquid hydrogen fluoride surrounded by a solid carbon dioxide/acetone bath. This slurry is allowed to stir overnight without replenishing the cooling bath. The hydrogen fluoride is removed by a stream of air. The residual solid was then dissolved in ether and washed with 10% aqueous sodium carbonate solution. The organic layer is dried over anhydrous magnesium sulphate and the solvent is evaporated to give the required chromanone with sufficient purity.

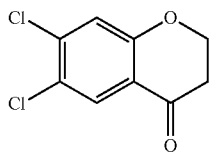

PC165C

PC165C: Off white solid, Yield: 350 mg (76%); $^1$H NMR (CDCl$_3$, 400 MHz) in ppm: δ 2.79 (t, 2H), 4.52 (t, 2H), 7.10 (s, 1H), 7.90 (s, 1H); $^{13}$C NMR (CDCl$_3$, 100 MHz) in ppm: δ 37.4, 67.6, 118.0, 120.2, 120.9, 126.0, 128.3, 140.0, 160.3, 189.9;

Synthesis of 3-bromo-6,7-dichloro-2,3-dihydrochromen-4-one (PC174): Procedure: A mixture of 100 mg (0.46 mmol) 6,7-dichlorochroman-4-one was dissolved in anhydrous ethanol (5 ml) and Chloroform (5 ml). To this solution was added pyridinium tribromide (0.442 g, 1.38 mmol, 3 equiv). The reddish brown mixture was heated with stirring at 50 C for 30 min. The reaction mixture was then cooled and the solvent was evaporated. Then water (20 ml) was added to the residue and it was then extracted with 20 ml of dichloromethane. The dichloromethane layer was then washed with 5% sodium bicarbonate solution followed by water (20 ml). The organic layer was then dried and the solvent was evaporated in vacuum to yield the crude product which was purified by column chromatography.

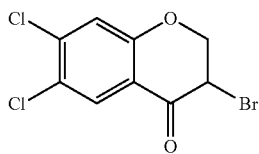

PC174

PC174: White powder, Yield: 104 mg (76%); $^1$H NMR (CDCl$_3$, 400 MHz) in ppm: δ 4.59-4.66 (m, 3H), 7.20 (s, 1H), 7.98 (s, 1H); $^{13}$C NMR (CDCl$_3$, 100 MHz) in ppm: δ 44.3, 71.7, 118.4, 120.2, 127.1, 129.3, 141.1, 159.0, 183.5.

Synthesis of 1-(7,8-dichloro-4H-chromeno[4,3-d] thiazol-2-yl)hydrazine (PC203)

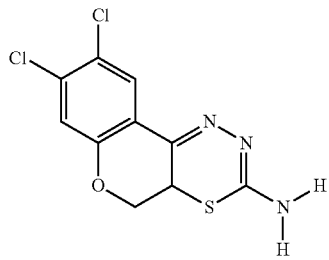

PC203F

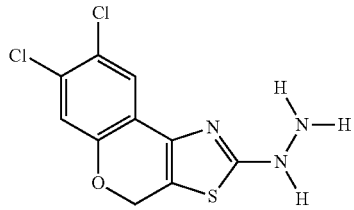

PC203S

Procedure: A solution of 250 mg (0.84 mmol) of the bromide and thiosemicarbazide (77 mg, 0.84 mmol) in 15 ml of anhydrous dioxane was stirred at 60° C. for 24 h. The resulting yellow precipitate was filtered and washed with dioxane (10 ml). The dried precipitate was then basified with 2 M Sodium Carbonate (20 ml) solution. The formed pale brown product was filtered at the pump and washed with water. The LCMS analysis showed the formation of the required 1-(7,8-dichloro-4H-chromeno[4,3-d]thiazol-2-yl)hydrazine along with minor amount of diazine. The crude product was used as such in the next step. Yield: 140 mg Synthesis of 2-(2-(7,8-dichloro-4H-chromeno[4,3-d]thiazol-2-yl)hydrazono)-3-(2-nitrophenyl)propanoic acid (PC204): Procedure: A suspension of 1-(7,8-dichloro-4H-chromeno[4,3-d]thiazol-2-yl)hydrazine, 140 mg (0.48 mmol) in 3.5 mL of 5% acetic acid was added to 2-nitro phenyl pyruvic acid 101 mg, (0.48 mmol) in 7 mL ethanol. The resulting mixture was refluxed 1 h. The precipitated yellow product was filtered and subjected to column chromatography. LCMS analysis showed the formation of the two isomers of the product. The product was purified by reverse-phase column chromatography, using triethylammonium bicarbonate buffer (50 mmol) and methanol as eluents.

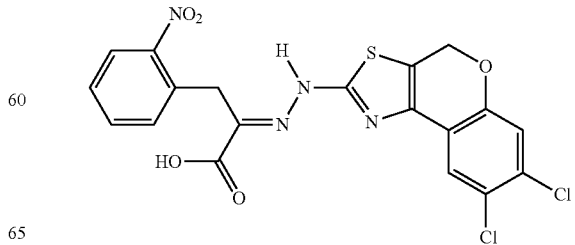

PC204F

Yellow powder. $^1$H NMR (DMSO-d$_6$, 500 MHz) in ppm: δ 4.28 (s, 2H), 5.45 (s, 2H), 7.06 (d, J=5.0 Hz, 1H), 7.17 (s, 1H), 7.43 (s, 1H), 7.50 (t, 1H), 7.64 (t, 1H), 8.05 (d, J=10.0 Hz, 1H); $^{13}$C NMR (DMSO-d$_6$, 125 MHz) in ppm: δ 30.0, 65.6, 118.8, 123.2, 124.2, 125.7, 128.5, 129.6, 130.6, 131.7, 134.5, 149.6, 152.9, 165.9. RP-HPLC on a C18 Xbridge column (4.6×100 mm, 1 mL/min), t$_R$=7.82 min, purity of 99.25%, employing a linear gradient system of acetonitrile-water: 50%-100% B in A for 20 min. Where A is 0.1% Trifluoroacetic acid in water and B is 0.1% Trifluoroacetic acid in acetonitrile. HRMS (ESI) calcd for: MW 477.99055. Found: m/z=478.99796 [M+H]$^+$.

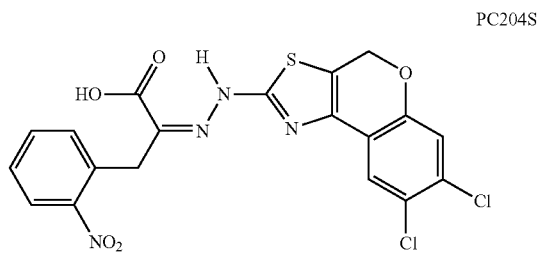 [SMILES: O=C(O)/C(Cc1ccccc1[N+](=O)[O-])=N\Nc1nc2c(s1)COc1cc(Cl)c(Cl)cc1-2]

PC204S

Yellow powder. $^1$H NMR (DMSO-d$_6$, 500 MHz) in ppm: δ 4.17 (s, 2H), 5.38 (s, 2H), 7.16 (s, 1H), 7.51-7.56 (m, 3H), 7.69 (s, 1H), 8.04 (d, J=10.0 Hz, 1H); $^{13}$C NMR (DMSO-d$_6$, 125 MHz) in ppm: δ 36.8, 65.5, 118.7, 123.6, 124.3, 125.2, 129.0, 130.7, 132.4, 133.7, 134.2, 149.6, 152.8, 164.6. RP-HPLC on a C18 Xbridge column (4.6×100 mm, 1 mL/min), t$_R$=10.20 min, purity of 100%, employing a linear gradient system of acetonitrile-water: 50%-100% B in A for 20 min. Where A is 0.1% Trifluoroacetic acid in water and B is 0.1% Trifluoroacetic acid in acetonitrile. HRMS (ESI) calcd for: MW 477.99055. Found: m/z=478.99785 [M+H]$^+$.

Scheme 5: 2-(2-(7,8-dimethoxy-4,5-dihydronaphtho[1,2-d]thiazol-2-yl)hydrazono)-3-(2-nitrophenyl)propanoic acid (PC195)

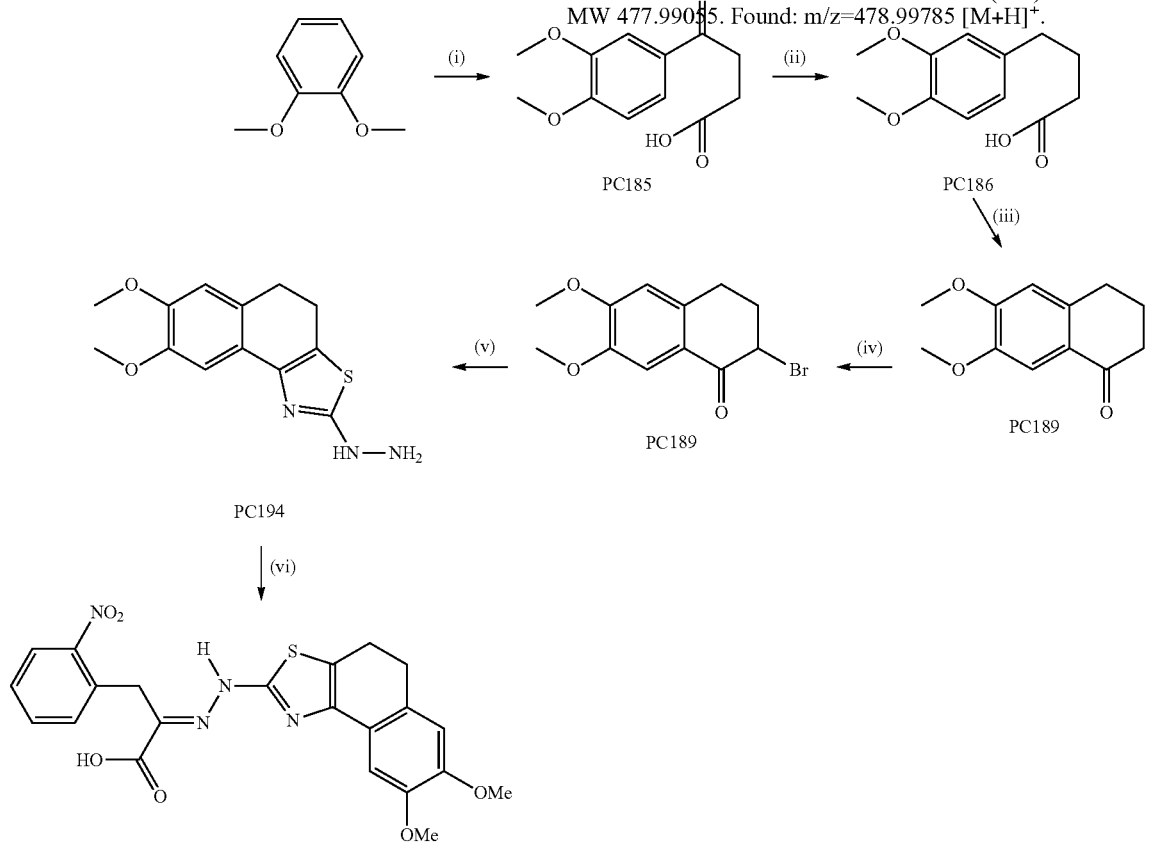

Reagents and Conditions:
(i) Succinic anhydride, Aluminum Chloride, Nitrobenzene, 10-35° C., 12 h, 46%
(ii) Zn—Hg, Con. HCl, Toluene, reflux 24 h, 70%
(iii) Polyphosphoric acid, 90° C., 6 h, 74%
(iv) Pyridinium tribromide, 20 min, 74%
(v) Thiosemicarbazide, Dioxane, 24 h, 52%
(vi) 2-Nitrophenylpyruvic acid, 5% Acetic acid-Ethanol (1:2), reflux, 1 h, 60%

Synthesis of 4-(3,4-dimethoxyphenyl)-4-oxobutanoic acid (PC185): Procedure: Veratrole (7 g, 0.05 mol) was added dropwise over 30 min to a stirred suspension of succinic anhydride (6 g, 0.6 mol) and Aluminium chloride (16 g, 0.12 mol) in 40 ml of nitrobenzene at 10° C. The temperature was then slowly raised to room temperature and was stirred at room temperature for 12 hours. The reaction mixture was then poured over ice cold water and then acidified with Con HCl. The solid product was filtered off and then redissolved in 1 N NaOH and extracted with ether. The ethereal layer was discarded and the aqueous layer was acidified with Con. HCl to obtain the required product. The pale yellow product was filtered and dried.

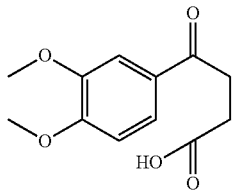

PC185

PC185: Pale yellow solid, Yield: 5.4 g (46%); $^1$H NMR (CDCl$_3$, 400 MHz) in ppm: δ 2.52-2.55 (t, 2H), 3.17-3.20 (t, 2H), 3.79 (s, 3H), 3.82 (s, 3H), 7.04 (d, J=8.0 Hz, 1H), 7.43 (d, J=4.0 Hz, 1H), 7.62-7.64 (m, 1H); $^{13}$C NMR (CDCl$_3$, 100 MHz) in ppm: δ 28.6, 33.3, 56.1, 56.3, 110.7, 11.5, 123.1, 130.0, 149.1, 153.6, 174.5, 197.4.

Synthesis of 4-(3,4-dimethoxyphenyl)butanoic acid (PC186): Procedure: Pure Zn dust (98%) (10.5 g) 0.12 mol and Mercuric Chloride, 1.05 g (3.9 mmol) were stirred with 3.5 ml of Con. HCl and 18 ml of water for 10 minutes. The aqueous solution was then syringed out leaving amalgamated zinc as a solid melt. To this material were added 6 ml of water and 13.5 ml of Con. HCl. To this stirred suspension was added 15 ml of toluene followed by 0.018 mol (4.5 g) of 4-(3,4-dimethoxyphenyl)-4-oxobutanoic acid. The reaction mixture was then refluxed with stirring for 24 hours. After each 5 hours time interval was added 3.5 ml of Con. HCl. The reaction mixture was cooled to room temperature. The toluene layer was separated and the aqueous layer was extracted with ethyl acetate. The toluene layer and ethyl acetate fractions were combined, dried and evaporated give the butyric acid as a oily substance. The LCMS analysis of the product showed the required mass, m/e: 224.25.

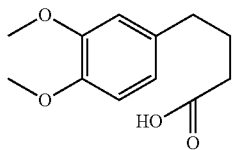

PC186

PC186: Brownish oil, Yield: 3 g (70%).

Synthesis of 6,7-dimethoxy-3,4-dihydronaphthalen-1 (2H)-one (PC189): Procedure: Polyphosphoric acid (50 g) was heated to melt at 90° C. for 30 minutes. To this was added 3 g (0.013 mol) 4-(3,4-dimethoxyphenyl)butanoic acid and this mixture was heated further with stirring for 6 h at 90° C. The reaction mixture was then cooled and ice cold water (200 ml) was added. It was then extracted with ethylacetate (100 ml) and then was washed with Saturated Sodium bicarbonate (100 ml). The organic phase was dried and evaporated in vacuum. The cyclized product 6,7-dimethoxy-3,4-dihydronaphthalen-1(2H)-one, was recrystallized from hexane-ethylacetate mixture. LCMS analysis showed the formation of the product and the disappearance of starting material.

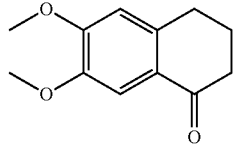

PC189

PC189: Colorless solid, Yield: 2 g (74%); $^1$H NMR (CDCl$_3$, 400 MHz) in ppm: δ 2.03-2.08 (m, 2H), 2.50-2.54 (m, 2H), 2.81-2.84 (m, 2H), 3.84 (s, 3H), 3.87 (s, 3H), 6.61 (s, 1H), 7.45 (s, 1H); $^{13}$C NMR (CDCl$_3$, 100 MHz) in ppm: δ 23.8, 29.6, 30.7, 56.1, 56.2, 108.6, 110.3, 125.9, 139.5, 148.0, 153.6, 197.3.

Synthesis of 2-bromo-6,7-dimethoxy-3,4-dihydronaphthalen-1(2H)-one (PC190): Procedure: A mixture of 500 mg. (2.4 mmol) 6,7-dimethoxy-3,4-dihydronaphthalen-1(2H)-one was dissolved in anhydrous ethanol (10 ml) and Chloroform (10 ml). To this solution was added pyridinium tribromide (0.768 g, 2.4 mmol). The reddish brown mixture was heated with stirring at 50° C. for 20 min. The reaction mixture was then cooled and the solvent was evaporated. Then water (20 ml) was added to the residue and it was then extracted with 50 ml of dichloromethane. The dichloromethane layer was then washed with 10% sodium bicarbonate solution (50 ml) followed by water (50 ml). The organic layer was then dried and the solvent was evaporated in vacuum to yield the crude product, 2-bromo-6,7-dimethoxy-3,4-dihydronaphthalen-1(2H)-one which was purified by column chromatography.

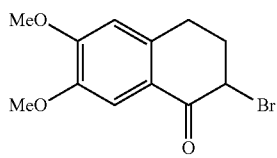

PC190

PC190: Off white solid, Yield: 500 mg (74%); $^1$H NMR (CDCl$_3$, 400 MHz) in ppm: δ 2.39-2.49 (m, 2H), 2.75-2.81 (m, 1H), 3.18-3.24 (m, 1H), 3.86 (s, 3H), 3.90 (s, 3H), 4.64-4.65 (m, 1H), 6.64 (s, 1H), 7.47 (s, 1H); $^{13}$C NMR (CDCl$_3$, 100 MHz) in ppm: δ 26.0, 32.4, 56.2, 56.3, 109.7, 110.2, 123.1, 138.3, 148.5, 154.4, 189.7.

Synthesis of 1-(7,8-dimethoxy-4,5-dihydronaphtho[1,2-d] thiazol-2-yl)hydrazine (PC194): Procedure: A solution of 400 mg (1.4 mmol) of 2-bromo-6,7-dimethoxy-3,4-dihydronaphthalen-1(2H)-one and thiosemicarbazide (127 mg, 1.4 mmol) in 20 ml of anhydrous dioxane was stirred at 80° C. for 24 h. The resulting yellow precipitate was filtered and washed with dioxane (10 ml). The dried precipitate was then basified with 2 M Sodium Carbonate (20 ml) solution. The formed pale brown product was filtered at the pump and washed with water. The LCMS analysis showed the formation of the required 1-(7,8-dimethoxy-4,5-dihydronaphtho[1, 2-d]thiazol-2-yl)hydrazine along with 7,8-dimethoxy-4,5-dihydro-4aH-naphtho[1,2-e][1,3,4]thiadiazin-3-amine.

PC194

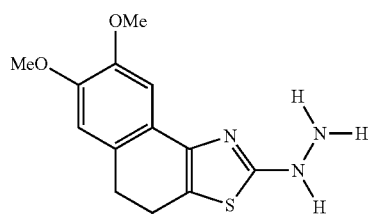

PC194: Off white powder, Yield: 250 mg.

Synthesis of (E)-2-(2-(7,8-dimethoxy-4,5-dihydronaphtho[1,2-d]thiazol-2-ylhydrazono)-3-(2-nitrophenyl)propanoic acid and (Z)-2-(2-(7,8-dimethoxy-4,5-dihydronaphtho[1,2-d]thiazol-2-yl)hydrazono)-3-(2-nitrophenyl) propanoic acid (PC195)

PC195S

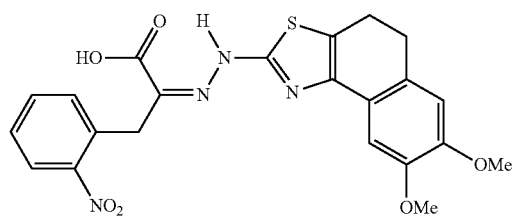

Procedure: A suspension of 1-(7,8-dimethoxy-4,5-dihydronaphtho[1,2-d]thiazol-2-yl)hydrazine, 250 mg (0.5 mmol) in 7 mL of 5% acetic acid was added to 2-nitro phenyl pyruvic acid (119 mg, (0.5 mmol) in 14 mL ethanol. The resulting mixture was refluxed 1 h. The precipitated yellow product was filtered and subjected to column chromatography. LCMS analysis showed the formation of the two isomers of the product with m/e=468.26. (Crude yield: 250 mg).

Yellow powder. $^1$H NMR (DMSO-$d_6$, 500 MHz) in ppm: δ 2.71 (t, 2H), 2.84 (t, 2H), 3.73 (s, 6H), 4.16 (s, 2H), 6.84 (s, 1H), 7.15 (s, 1H), 7.49-7.56 (m, 2H), 7.67-7.71 (m, 1H), 8.03-8.05 (m, 1H); $^{13}$C NMR (DMSO-$d_6$, 125 MHz) in ppm: δ21.8, 28.3, 36.6, 56.2, 125.2, 127.4, 128.8, 132.7, 133.5, 134.1, 148.0, 148.4, 149.7, 164.6. RP-HPLC on a C18 Xbridge column (4.6×100 mm, 1 mL/min), $t_R$=13.21 min, purity of 98.79%, employing a linear gradient system of acetonitrile-water: 20%-80% B in A for 20 min. Where A is 0.1% Trifluoroacetic acid in water and B is 0.1% Trifluoroacetic acid in acetonitrile.

EXAMPLE IX

Synthesis of Piperazine Derivatives

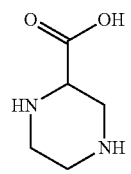

Molecular Weight: 130.15

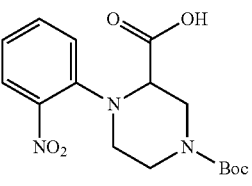

RYF-220
Chemical Formula: $C_{16}H_{21}N_3O_6$
Molecular Weight: 351.35

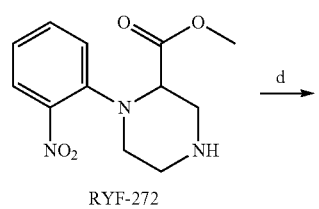

RYF-272
Chemical Formula: $C_{12}H_{15}N_3O_4$
Molecular Weight: 265.27

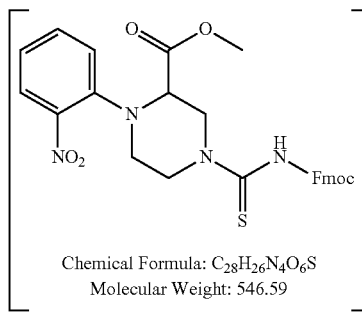

Chemical Formula: $C_{28}H_{26}N_4O_6S$
Molecular Weight: 546.59

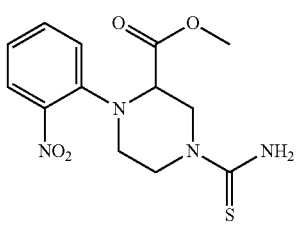

Chemical Formula: $C_{13}H_{16}N_4O_4S$
Molecular Weight: 324.36

-continued

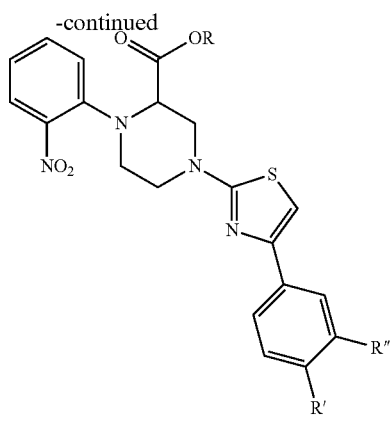

R = Me
RYF-273 R' = Cl, R" = Cl
RYF-402 R' = OMe, R" = H
RYF-405 R' = H, R" = H

R = H
RYF-276 R' = Cl, R" = Cl
RYF-404 R' = OMe, R" = H
RYF-408 R' = H, R" = H a: Boc-ON, NaOH, Dioxane
b: 2-flouronitrobenzene, K$_2$CO$_3$, DMSO
c: SOCl$_2$, methanol, reflux, 2 hrs
d: Fmoc-NCS, CH$_2$Cl$_2$/DMF; 20% piperidine in methanol
e: appropriate bromoacetophenone
f: 1N NaOH, Dioxane, reflux, 0.5 hrs

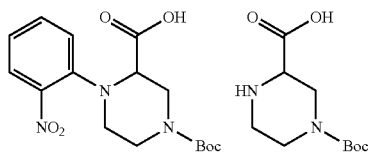

Chemical Formula: C$_{10}$H$_{18}$N$_2$O$_4$
Molecular Weight: 230.26
4-(tert-butoxycarbonyl)piperazine-2-carboxylic acid 4-(tert-butoxycarbonyl)piperazine-2-carboxylic acid: To a solution of 2-piperazine-carboxylic acid dihydrochloride (1.0 g, 4.92 mmol) in 20 mL of water/dioxane 1:1, NaOH 6N was added to adjust the pH to 11. A solution of BOC-ON (1.34 g, 5.41 mmol) in dioxane (5 mL) was then added dropwise, while maintaining the pH=11 during the addition and the resulting solution was stirred overnight at room temperature. Another 0.134 g of BOC-ON were added and the reaction mixture was stirred for 2 h. The solvent was evaporated under reduced pressure and the residue was diluted with diethyl ether/water (60 mL). The phases were separated and the pH of the aqueous layer was adjusted to 7 by slow addition of HCl 1N. Evaporation of water under reduced pressure afforded the title compound as a white solid which was dried in a vacuum oven at 50 C and used without further purification for the next step.

Alternatively, to a solution of 2-piperazine-carboxylic acid dihydrochloride (1.17 g, 5.79 mmol) in 20 mL of water/dioxane 1:1, NaOH 6N was added till pH basic. A solution of BOC-ON (1.57 g, 12.0 mmol) in dioxane (5 mL) was then added dropwise, while maintaining the basic during the addition and the resulting solution was stirred for 18 hrs at room temperature. The solvent was evaporated under reduced pressure and the residue was diluted with diethyl ether/water (60 mL). Separation of the phases and evaporation of water under reduced pressure afforded the compound as a white solid which was and used without further purification for the next step.

RYF-206, 220: 1-Fluoro-2-nitrobenzene (0.14 gr, 0.98 mmole, 0.1 ml) was added to a suspension of potassium carbonate (0.55 gr, 4 mmole) and 4-(tert-butoxycarbonyl) piperazine-2-carboxylic acid (0.2 gr, 0.89 mmole) in dry DMSO (4 ml), under N$_2$ atm. The reaction mixture was stirred overnight at 110° C. After cooling the reaction mixture to rt, HCl (1N) was added dropwise till pH acidic. The mixture was diluted with water and washed with ethyl acetate three times. The combined organic layers were dried (MgSO$_4$) and the solvents evaporated. The residue was loaded on Biotage (RP, gradient of 0 to 100% methanol in water in 8 CV), to give the desired product in 76% yield (0.24 gr).

RYF-206: $^1$H-nmr (methanol-d$_4$, 600 MHz): δ=7.73 (dd, J=8.4, 1.8 Hz, 1H, Ar), 7.50 ("td", J=8.4, 1.8 Hz, 1H, Ar), 7.36 (d, J=8.4 Hz, 1H, Ar), 7.09 ("td", J=7.8, 1.2 Hz, 1H, Ar), 4.01 (bs, 1H), 3.81 (t, J=4.2 Hz, 1H), 3.74-3.63 (m, 3H), 3.39 (bs, 1H), 3.35 (s, 1H), 2.88 (m, 1H), 1.41 (s, 9H, CH$_3$). LCMS: Calcd. for C$_{16}$H$_{21}$N$_3$O$_6$: 351.35, found: 352.20 [MH$^+$].

RYF-251, 272: SOCl$_2$ (2.2 ml) was added dropwise to a solution of RYF-220 (0.54 gr, 1.54 mmole) in dry methanol (15 ml) at 0 C. After the addition was complete, the reaction mixture was heated to reflux for 1.5 hrs. According to LCMS the SM was fully converted to the desired product. The methanol was evaporated to dryness to give RYF-251 in 92% yield (0.38 gr), which was used in the next step without further purification.

RYF-206ester: $^1$H-nmr (D$_2$O, 600 MHz): δ=7.85 (dd, J=8.4, 1.8 Hz, 1H, Ar), 7.57 ("td", J=8.4, 1.8 Hz, 1H, Ar), 7.34 (dd, J=8.4, 1.2 Hz, 1H, Ar), 7.19 ("td", J=7.8, 1.2 Hz, 1H, Ar), 4.41 (t, J=4.2 Hz, 1H), 3.65 (dd, J=13.2, 3.6 Hz, 1H), 3.57 (s, 3H), 3.55 (t, J=3.6 Hz, 1H), 3.53 (dd, J=8.4, 4.2 Hz, 1H), 3.35 (m, 1H), 3.28 (m, 2H), 1.41 (s, 9H, CH$_3$). $^{13}$C-nmr (D$_2$O, 600 MHz): δ=171.0, 143.7, 135.0, 126.2, 125.2, 124.5, 59.0, 53.1, 45.0, 44.2, 43.5. LCMS: Calcd. for C$_{12}$H$_{15}$N$_3$O$_4$: 265.27, found: 266.14 [MH$^+$].

RYF-267 (0.36 to 0.45 gr of urea): RYF-251 (0.36 gr, 1.36 mmole) was dissolved in dry DMF (2 ml) under N$_2$ atm. and added to a solution of Fmoc-isothiocyanate (fluorenylmethyloxycarbonyl isothiocyanate, 0.38 gr, 1.36 mmole) in dry CH$_2$Cl$_2$, at 0 C, under N$_2$ atm. The mixture was left to warm up spontaneously to rt and left to stir overnight. LCMS indicated the full conversion of 251 to the desired Fmoc derivative. A solution of 10% piperidine in methanol (1 ml) was added slowly and after stirring at rt for 3 hrs, the solvents were removed under high pressure. LCMS for Fmoc derivative: Calcd. for C$_{28}$H$_{26}$N$_4$O$_6$S: 546.59, found: 547.24 [MH$^+$]. LCMS for thiourea derivative: Calcd. for C$_{13}$H$_{16}$N$_4$O$_4$S: 324.36, found: 325.09 [MH$^+$].

General Procedure for the Thiazole Ring Formation: Appropriate bromoacetophenone (2.1 mmole) was dissolved in dioxane (2 ml) and added to a solution of RYF-251 (2 mmole) in dioxane. The reaction mixture was left to stir overnight at rt. LCMS indicated the full consumption of the thiourea, the solvents were removed under vacuum, and the residue separated on Biotage (NP, gradient of 0 to 80 ethyl acetate in hexane in 12 CV), to give the desired product as yellow-brown oil. (Yield: RYF-273 (48%), 402 (34%), 405 (56%)).

RYF-273: $^1$H-nmr (CDCl$_3$, 400 MHz): δ=7.93 (s, 1H, Ar), 7.82 (d, J=8.0 Hz, 1H, Ar), 7.63 (d, J=8.0 Hz, 1H, Ar), 7.23 (t, J=7.8 Hz, 1H, Ar), 7.42 (d, J=8.4 Hz, 2H, Ar), 7.14 (d, J=8.0 Hz, 1H, Ar), 6.82 (s, 1H, H-thiazole), 4.34 (d, J=12.0 Hz, 1H), 4.0 (s, 1H), 4.07 (d, J=12.0 Hz, 1H), 3.95 (t, J=11.2 Hz, 1H), 3.73 (dd, J=12.4, 1.6 Hz, 1H), 3.62 (s, 3H, CH$_3$), 3.40 (t, J=12.0 Hz, 1H), 3.14 (d, J=12.0 Hz, 1H). $^{13}$C-nmr (CDCl$_3$, 600 MHz): δ=170.7, 170.6, 149.3, 177.7, 144.3, 134.8, 133.6, 132.6, 131.2, 131.0, 130.4, 127.9, 125.7, 125.1, 124.8, 124.5, 123.6, 103.5, 60.9, 52.1, 50.7, 48.3, 46.9. LCMS: Calcd. for C$_{21}$H$_{18}$Cl$_2$N$_4$O$_4$S: 494.04, 492.04, found: 494.93, 492.98[MH$^+$].

RYF-402: $^1$H-nmr (CDCl$_3$, 600 MHz): δ=7.82 (d, J=8.4 Hz, 1H, Ar), 7.77 (d, J=8.4 Hz, 2H, Ar), 7.53 (t, J=7.8 Hz, 1H, Ar), 7.42 (d, J=7.8 Hz, 1H, Ar), 7.14 (t, J=7.8 Hz, 1H, Ar), 6.90 (d, 9.0 Hz, 2h, Ar), 6.68 (s, 1H, H-thiazole), 4.35 (d, J=12.0 Hz, 1H), 4.20 (s, 1H), 4.06 (d, J=12.6 Hz, 1H), 3.95 (td, J=11.4, 2.4 Hz, 1H), 3.83 (s, 3H, CH$_3$), 3.73 (dd, J=12.0, 3.6 Hz, 1H), 3.62 (s, 3H, CH$_3$), 3.40 (td, J=14.4, 3.0 Hz, 1H), 3.14 (d, J=12.0 Hz, 1H). $^{13}$C-nmr (CDCl$_3$, 600 MHz): δ=170.7, 170.6, 159.3, 151.5, 144.8, 144.3, 133.6, 127.9, 127.3, 125.7, 124.4, 123.5, 113.9, 100.4, 61.0, 55.3, 52.1, 50.8, 48.4, 46.9. LCMS: Calcd. for C$_{22}$H$_{22}$N$_4$O$_5$S: 454.50, found: 455.11 [MH$^+$].

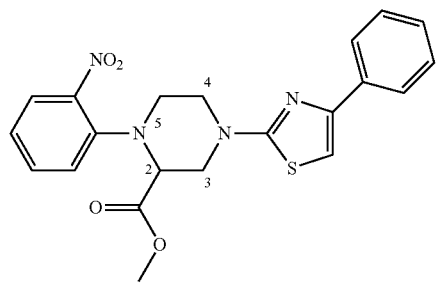 [SMILES: COC(=O)C1CN(c2nc(-c3ccccc3)cs2)CCN1c1ccccc1[N+](=O)[O-]]

RYF-405: $^1$H-nmr (CDCl$_3$, 600 MHz): δ=7.84 (d, J=7.8 Hz, 2H, Ar), 7.82 (d, J=8.4 Hz, 1H, Ar), 7.52 (td, J=8.4, 1.0 Hz, 1H, Ar), 7.41 (d, J=8.4 Hz, 1H, Ar), 7.34 ("t", J=7.8 Hz, 2H, Ar), 7.27, ("dd", J=14.4, 7.2 Hz, 1H, Ar), 7.13 (t, J=7.8 Hz, 6.81 (s, 1H, H-thiazole), 4.36 (dd, J=12.0, 1.2 Hz, 1H, H-3), 4.20 (s, 1H, H-2), 4.07 ("dt", J=12.6 Hz, 1H, H-5), 3.94 (td, J=11.4, 3.0 Hz, 1H, H-4), 3.73 (dd, J=12.0, 3.6 Hz, 1H, H-3), 3.61 (s, 3H, CH$_3$), 3.40 (td, J=14.4, 2.4 Hz, 1H, H-5), 3.13 (d, J=12.0 Hz, 1H, H-4). $^{13}$C-nmr (CDCl$_3$, 600 MHz): δ=170.7, 170.6, 151.7, 144.8, 144.3, 134.9, 133.5, 128.5, 127.7, 126.0, 125.6, 124.4, 123.4, 102.2, 61.0, 52.1, 50.8, 48.4, 46.9. LCMS: Calcd. for C$_{21}$H$_{22}$N$_4$O$_4$S: 424.47, found: 425.06 [MH$^+$].

General Procedure for the Ester Hydrolysis: The methyl ester (0.87 mmole) was dissolved in a 1:1 solution of dioxane and 2N NaOH (3.6 ml) and the reaction mixture was refluxed for 30 min. The solution was cooled to rt and acidified with HCl (1N), the solvents removed and the residue purified on Biotage (RP, gradient of 0 to 100 methanol (containing 0.1% acetic acid) in water, in 12 CV). After removal of the solvents the final product was obtained as yellow-orange foam. Yields: RYF-276 (51%), 404 (69%), 408 (78%)).

RYF-408: $^1$H-nmr (CDCl$_3$, 600 MHz): δ=7.08 (m, 3H, Ar), 7.30 (d, 4H, Ar), 7.24 (t, J=7.2 Hz, 1H, Ar), 7.03 (d, J=7.8 Hz, 1H, Ar), 6.71 (s, 1H, H-thiazole), 4.32 (d, J=16.8 Hz, 1H), 4.13 (s, 1H), 4.01 (d, J=17.4 Hz, 1H), 3.86 (t, J=9.6 Hz, 1H), 3.67 (dd, J=12.0, 3.0 Hz, 1H), 3.36 (t, J=14.4, 2.4 Hz, 1H), 3.08 (d, J=11.4 Hz, 1H). $^{13}$C-nmr (CDCl$_3$, 600 MHz): δ=171.2, 151.8, 145.2, 143.9, 135.0, 133.8, 128.7, 127.9, 126.2, 125.9, 124.2, 123.0, 102.4, 61.3, 51.1, 48.4, 47.4. LCMS: Calcd. for C$_{20}$H$_{18}$N$_4$O$_4$S: 410.45, found: 411.14 [MH$^+$].

EXAMPLE X

Synthesis of Fused Benzothiazole Analogs of 4EGI-1

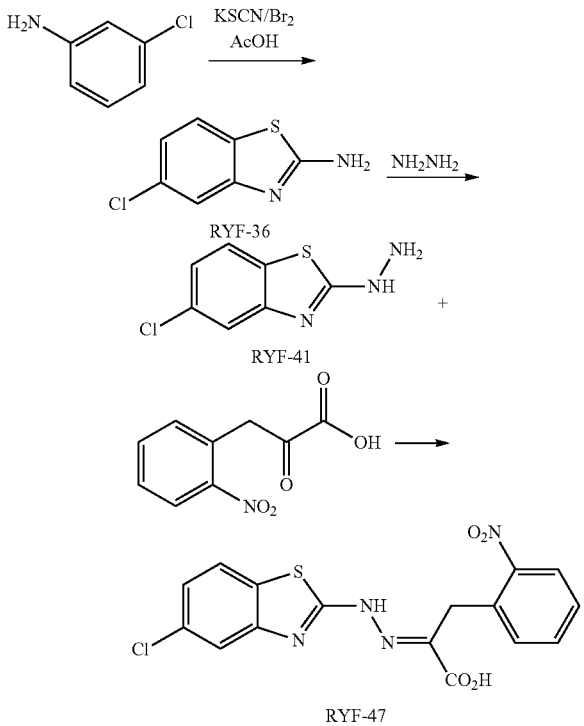

A solution of bromine (2.67 gr, 0.017 mole) in acetic acid (60 ml) was added dropwise to a solution of potassium thiocyanate (0.43 gr, 0.025 mole) and 3-chloroanilin (2.12 gr, 0.017 mole) in acetic acid (50 ml) at 0 C The ice bath was removed and the mixture was left to stir for additional 7 hrs at rt. The reaction mixture was poured into water, the pH brought to 11 with ammonium hydroxide, and the precipitate that was formed was filtered.

$^1$H-nmr (RYF-36a, DMSO-d$_6$): 7.42 (d, J=8.4 Hz, 1H, H-7), 7.78 (d, J=2.4 Hz, 1H, H-4), 6.56 (dd, J=8.8, 2.4 Hz, 1H, H-6), 6.07 (bs, 2H, NH$_2$). $^{13}$C-nmr: 153.8, 138.4, 137.7, 115.2, 114.4, 112.5, 104.1.

RYF-41: To a solution of 36 (1.3 gr, 7 mmole) in ethylene glycol (5 ml) was added dropwise H$_2$SO$_4$ (0.5 ml), followed by the addition of hydrazine hydrate (65%, 0.5 ml, 10.6 mmole) and the reaction mixture was heated to reflux for 4 hrs. The reaction mixture was allowed to cool to rt and was left to stir overnight. The suspension that was formed during the night was diluted with water, filtered, and dried under high vacuum in presence of P$_2$O$_5$. No further purification was required.

$^1$H-nmr (RYF-42 hydrazine, DMSO-d$_6$): 7.08 (d, J=8.4 Hz, 1H, H-7), 6.65 (d, J=2.0 Hz, 1H, H-4), 6.40 (dd, J=8.4, 2.4 Hz, 1H, H-6), 5.78 (bs, 2H, NH$_2$), 3.3 (s). $^{13}$C-nmr: 152.3, 138.5, 137.4, 118.2, 114.8, 113.5.

RYF-47: 3-(2-nitrophenyl)-2-oxopropanoic acid (0.42 mg, 2 mmole) and 41 (0.4 mg, 2 mmole) were dissolved in a solution of 5% acetic acid in methanol (8.4 ml), and the reaction mixture was heated to reflux overnight. Water were added and orange oil precipitated. Ethyl acetate was added and the organic phase was washed with sat. sodium bicarbonate, brine, dried (Na$_2$SO$_4$) and evaporated. The resulting oil was was chromatographed on Biotage using a gradient of 25-50% (Ethyl acetate:cyclohexane).

EXAMPLE XI
Synthesis of Additional Compounds
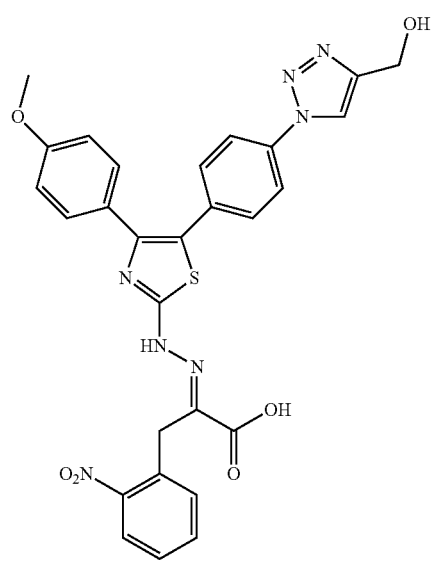
MW = 585.59 gr/mol
Purity: 97%
LC—MS analysis: OK
HPLC analytical: OK
$^1$H—NMR: OK
1-Chemical pathway
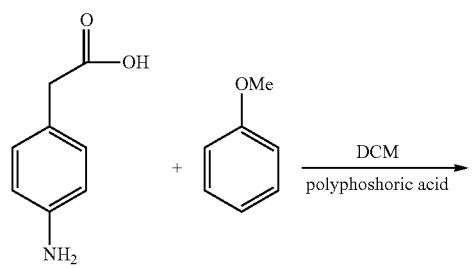
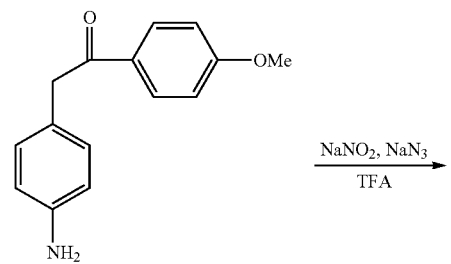
KY-375
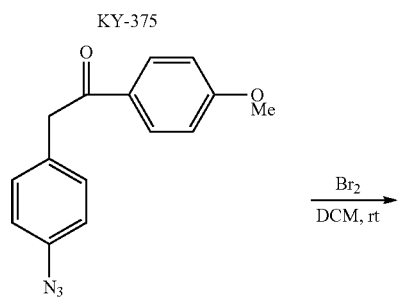
KY-377
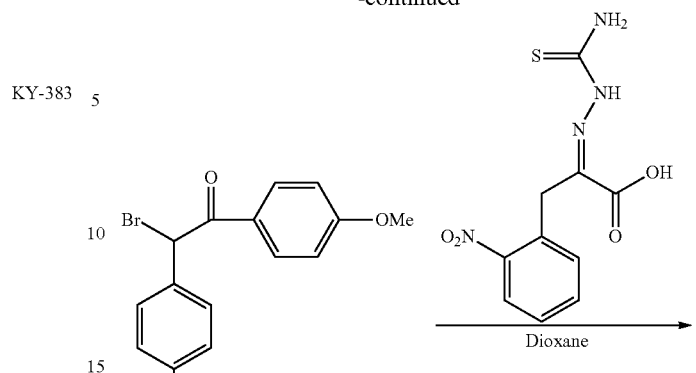
KY-379-step A
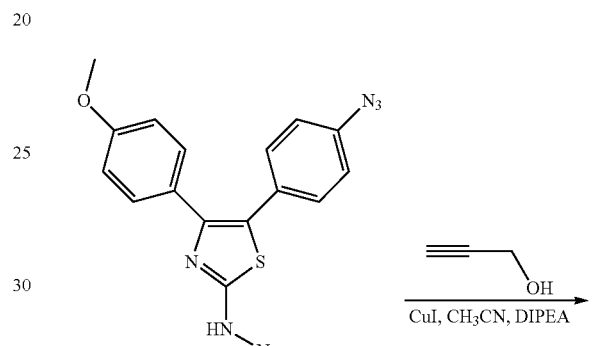
KY-379-pri
529.53 gr/mol
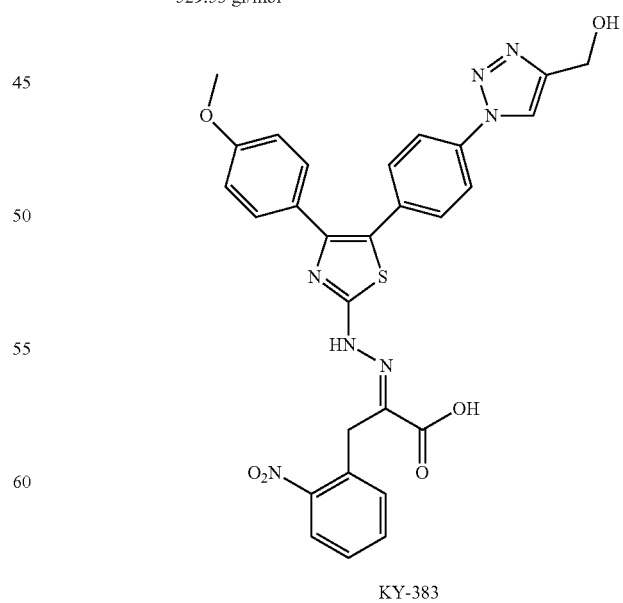
KY-383
585.59 gr/mol

Synthesis of 2-{[5-[4-(4-hydroxymethyl-[1,2,3]triazol-1-yl)-phenyl]-4-(4-methoxy-phenyl)-thiazol-2-yl]-hydrazono}-3-(2-nitro-phenyl)-propionic acid (KY-383)

Synthesis of 2-(4-amino-phenyl)-1-(4-methoxy-phenyl)-ethanone (KY-375): (4-amino-phenyl)-acetic acid (1 gr, 6.6 mmol) was dissolved in DCM (7 ml) in an open flask, and polyphosphoric acid (22 gr) was added. The mixture was stirred carefully at 80° C. for 10 min. Then methoxy-benzene (0.7 ml, 6.6 mmol) was added at the same temperature for 2 h and then poured on crushed ice. The solution was carefully alkalized with 25% ammonia and then extracted with DCM (3×50 ml). The combined extracts were dried ($Na_2SO_4$). The products, after evaporation of the solvent, were purified by recrystallization from MeOH. Yield 0.4599 (30%)

Synthesis of 2-(4-Azido-phenyl)-1-(methoxy-phenyl)-ethanone (KY-377) To a solution of 2-(4-Amino-phenyl)-1-(4-methoxy-phenyl)-ethanone (0.4599 gr, 1.96 mmol) in 4.2 ml of TFA at 0° C. was added sodium nitrite (0.26 gr, 3.79 mmol) in one portion. After the mixture was stirred 1 h, sodium azide (0.618 gr, 9.49 mmol) was added slowly over 20 min followed by addition of 5 ml $Et_2O$. the resulting mixture was stirred in the dark for an additional 1 h and the temperature was allowed to rise to room temperature. After the solvent was evaporated, the residue was dissolved in 20 ml of 1 N HCl and extracted with EtOAC (3×30 ml). the combined organic phases were washed with brine (50 ml) and dried over $Na_2SO_4$. the solvent was removed under pressure. The residue was purified by recrystallization from MeOH. Yield 0.23 (30%)

Synthesis of 2-{[5-(4-Azido-phenyl)-4-methoxy-phenyl)-thiazol-2-yl]-hydrazono}-3-(2-nitro-phenyl)-propionic acid (KY-379)

2-(4-Azido-phenyl)-2-bromo-1-(4-methoxy-phenyl-ethanone: Step A (KY-379-A) A solution of bromine (46.14 ul, 0.89 mmol) in DCM (1.87 ml) was added slowly to a solution of 2-(4-Azido-phenyl)-1-(methoxy-phenyl)-ethanone (0.2 gr, 0.748 mmol) in DCM (2.8 ml). Then the solution was stirred with 5 min. The solution was concentrated under vacuum.

2.3.2 Synthesis of 2-{[5-(4-Azido-phenyl)-4-methoxy-phenyl)-thiazol-2-yl]-hydrazono}-3-(2-nitro-phenyl)-propionic acid (KY-379-pri) A solution of a hydrazine-thiosemicarbazide KY-385 (0.211 g, 0.748 mmol) and bromo-ethanone (in situ) (0.748) in dioxane (1.5 ml) was stirred at room temperature over night. The precipitate compound (only one isomer) was filtered and washed with dioxane and cyclohexane. And dry under vacuo. Yield 160 mg (40% one isomer). the solution contain to isomers 250 mg.

2.4 Synthesis of 2-{[5-[4-(4-hydroxymethyl-[1,2,3]triazol-1-yl)-phenyl]-4-(4-methoxy-phenyl)-thiazol-2-yl]-hydrazono}-3-(2-nitro-phenyl)-propionic acid (KY-383) To a solution of azido KY-379-pri (60 mg) in $CH_3CN$ 0.4 ml, tert-Butanol 0.2 ml was added diisopropylethylamine 50 ul followed by propargyl alcohol (10 ul, 0.169 mmol), CuI (5 mg). The reaction was stirred at rt over night, to the solution was diluted with MeOH, the solution was filtrated and added acetic acid 100 ul. the solvent was removed under pressure. The residue was flash chromatographic (DCM:MeOH 10% $NH_3OH$).

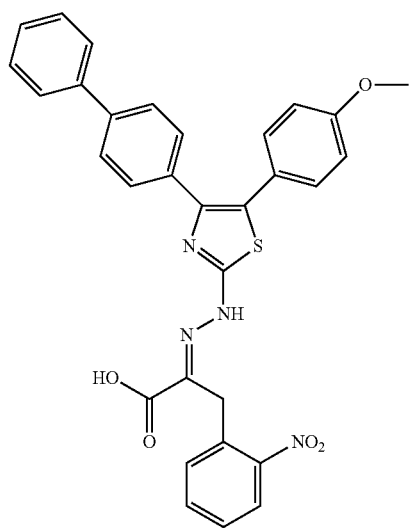

KY-577

MW = 564.61 gr/mol  
Purity: 98%  
LC—MS analysis: OK  
HPLC analytical: OK  
$^1H$—NMR: -

1-Chemical pathway

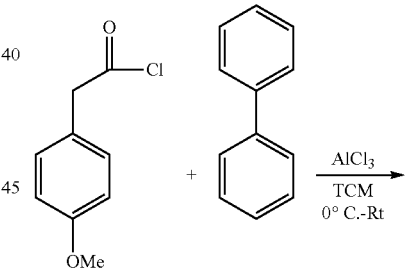

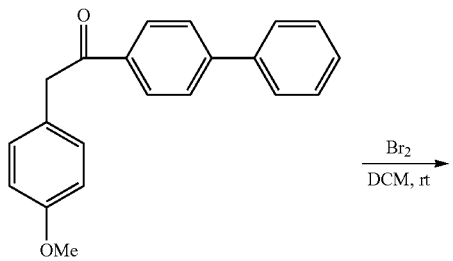

KY-560  
302 gr/mol

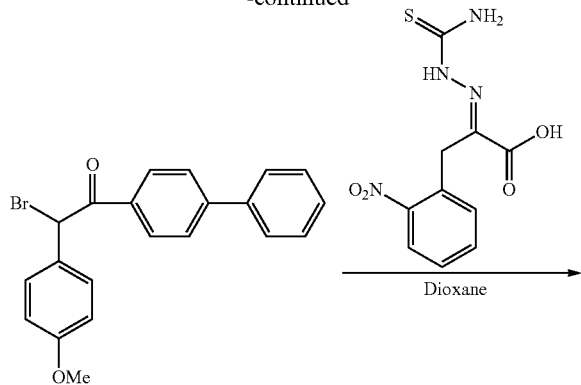

KY-577-A
381.26 gr/mol

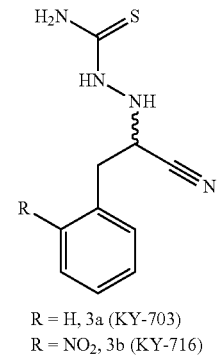

KY-577

Synthesis of 2-{[4-Biphenyl-4-yl-5-(4-methoxy-phenyl)-thiazol-2-yl]-hydrazono}-3-(2-nitro-phenyl)-propionic acid (KY-577)

Synthesis of 1-Biphenyl-4-yl-2-(4-methoxy-phenyl)-ethanone: KY-560 In a round bottom flask equipped with gas inlet and magnetic stirrer were placed Biphenyl (2.1 gr, 13.65 mmol), Aluminum trichloride (1.5 gr, 11.25 mmol), and 150 ml of tetrachloroethane (TCM). While the TCM solution was stirring, a solution of 25 ml of tetrachloroethane and 0.830 ml of (4-Methoxy-phenyl)-acetyl chloride (5.5 mmol) was dropwise over five minutes by syringe. The reaction mixture was stirred 3-4 h. 150 ml of water and 5 ml of HCl were slowly added. The layers were separated. The aqueous layer was extracted with DCM. The combined DCM and TCE solution was washed with a saturated solution of NaCl in water. The organic solution was dried over Na2SO4. filtration followed by rotary evaporation produced a dark yellow solid. Chromatography on flash chromatographic (CycloHexane:DCM). Yield 1.2 gr (71%) as a white solid.

2-Biphenyl-4-yl-2-bromo-1-(methoxy-phenyl)-ethanone (Step A): (KY-577-A) A solution of bromine (51 ul) in 2 ml DCM was added slowly to a solution of 1-(Biphenyl-4-yl-2-(4-methoxy-phenyl)-ethanone (0.25 gr, 0.826 mmol) in 3.1 ml DCM. Then the solution was stirred at room temperature 15 min. The solution was concentrated under vacuum.

Synthesis of 2-{([4-Biphenyl-4-yl-5-(4-methoxy-phenyl)-thiazol-2-yl]-hydrazono}-3-(2-nitro-phenyl)-propionic acid (KY-577) A solution of a hydrazine-thiosemicarbazide KY-385 (0.23 g, 0.826 mmol) and bromo-ethanone (in situ) (0.826 mmol) in dioxane (1.65 ml) was stirred at room temperature over night. The residue was flash chromatographic (DCM:MeOH). LC-MS assay showed the desired product. we had two fraction, one fraction have two isomers Yield 318 mg (68%) and the Sc and fraction have one isomer (S). Yield 64 mg (14%).

Synthesis of (RS)-2-(1-cyano-2-phenylethyl)hydrazinecarbothioamide (3a) and (RS)-2-(1-cyano-2-(2-nitrophenyl)ethyl)hydrazinecarbothioamide (3b)

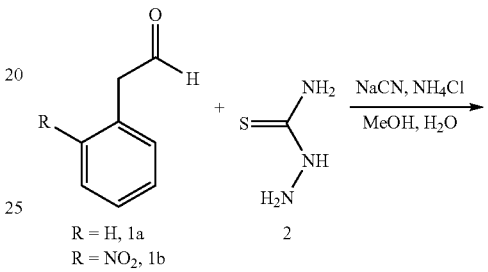

R = H, 1a
R = NO₂, 1b

R = H, 3a (KY-703)
R = NO₂, 3b (KY-716)

To a solution of the phenyl-acetaldehyde 1a or 2-nitrophenyl-acetaldehyde 1b (8.3 mmol), thiosemicarbazide 2b (0.757 gr, 8.32 mmol) in H₂O-methanol 55 ml (1:10 v/v) were added NaCN (0.624 g, 12.7 mmol) and NH₄Cl (1.04 g, 19.44 mmol). The reaction mixture was stirred overnight at 50° C. The product from 1b was filtered, washed with cold water and dried under vacuum yielding 0.157 g (10%) of pure hydrazinecarbothioamide (3b). The precipitated crude product from 1a was purified on C18-reversed phase flash chromatography column employing a linear gradient of 0-30% A in B (flowrate 40 mL/min), where A is 0.1% formic acid in CH₃CN and B is 0.1% of formic acid in water, yielding 310 mg (15%) of pure 3b.

(RS)-2-(1-cyano-2-phenylethyl)hydrazinecarbothioamide (3a) (KY-703): ¹HNMR (400 MHz, DMSO-d₆) δ 2.88 (dd, J=12.4, 9.2 Hz, 1H), 3.05 (dd, J=12.4, 5.6 Hz, 1H), 4.1 (m, 1H), 5.91 (d, J=4.4 Hz, 1H), 7.1-7.4 (6H), 7.9 (s, bs, 1H), 8.98 (s, bs, 1H). ¹³C-NMR δ 36.85 (CH₂), 54.02 (CHCH₂), 119.7 (CN), 127.78, 128.640, 128.640, 129.97, 130.24, 136.4, 182.44 (CS). MS⁺(ESI) m/z 220.86 ([M+H]⁺=221.98), calcd mass 220.08.

(RS)-2-(1-cyano-2-(2-nitrophenyl)ethyl)hydrazinecarbothioamide (3b) (KY-716): ¹HNMR (400 MHz, DMSO-d₆) δ 3.22 (dd, J=13.6, 9.6 Hz, 1H), 3.39 (dd, J=13.6, 5.6 Hz, 1H), 4.26 (m, 1H), 6.04 (d, J=3.6 Hz, 1H), 7.3 (s, 1H), 7.57 (m, 2H), 7.73 (m, 1H), 8.02 (m, 1H) 9.06 (s, 1H). $^{13}$C-NMR δ 33.81 (CH$_2$), 52.90 (CHCH$_2$), 119.27 (CN), 125.57, 129.64, 130.84, 133.84, 134.34, 149.85 (CNO$_2$), 182.51 (CS). MS$^+$ (ESI) m/z=265.96 ([M+H]$^+$=267.95), calcd mass 265.06.

Synthesis of (RS)-2-(2-(4-(3,4-dichlorophenyl)thiazol-2-yl)hydrazinyl)-3-(2-phenyl) propanoic acid (6a) and (RS)-2-(2-(4-(3,4-dichlorophenyl)thiazol-2-yl)hydrazinyl)-3-(2-nitrophenyl) propanoic acid (6b)

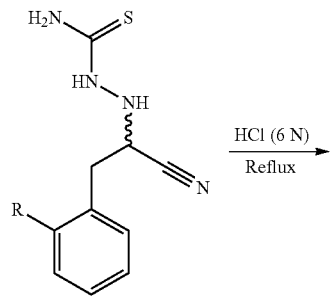

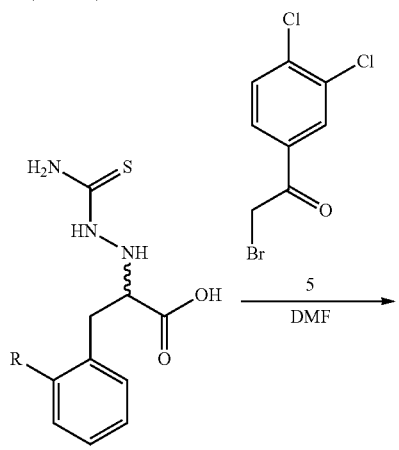

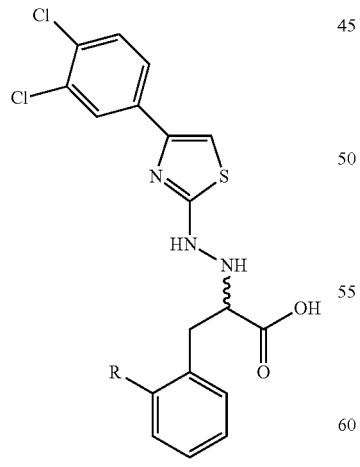

A solution of 2-aminothiourea-3-(2-R-phenyl)-propionitriles (0.454 mmol) in aq. HCl (6 M, 4.5 ml) was stirred at reflux temperature for 5 h, to obtain their corresponding acids [4a, 4b]. The intermediate acids were cyclised with 2-bromo-1-(3,4-dichlorophenyl) ethanone 5 (0.121 gr, 0.454 mmol) in DMF (1.4 ml) for 1 h at room temperature to afford the required (RS)-2-(2-(4-(3,4-dichlorophenyl)thiazol-2-yl)hydrazinyl)-3-(phenyl) propanoic acid (6a) and (RS)-2-(2-(4-(3,4-dichlorophenyl)thiazol-2-yl)hydrazinyl)-3-(2-nitrophenyl) propanoic acid (6b). The precipitated crude products from 6a and 6b were purified on C18-reversed phase flash chromatography column employing a linear gradient of 0-40% A in B (flow-rate 40 mL/min), where A is 0.1% formic acid in CH$_3$CN and B is 0.1% of formic acid in water, yielding 80 mg (43%) of pure 6a and yielding 87 mg (72%) of pure 6b.

(RS)-2-(2-(4-(3,4-dichlorophenyl)thiazol-2-yl)hydrazinyl)-3-(phenyl)propanoic acid 6a: $^1$HNMR (400 MHz, DMSO-d$_6$) δ 2.84 (dd, J=13.6, 7.6 Hz, 1H), 2.93 (dd, J=13.6, 6.4 Hz, 1H), 3.6 (m, 1H), 5.72 (s, bs, 1H), 7.16-7.31 (m, 6H), 7.59 (d, J=8.4 Hz, 1H), 7.73 (dd, J=8.4, 1.88 Hz), 7.95 (d, J=1.88 Hz, 1H), 8.9 (s, bs, 1H). $^{13}$C-NMR δ 37.03 (CHCH$_2$), 65.31 (CHCH$_2$), 105.814 (CH), 126.07, 126.941, 127.65, 128.77, 129.93, 131.39, 131.96, 136.29, 138.64, 148.55, 174.58, 175.09 (CO$_2$H). MS$^+$(ESI) m/z=407.84 ([M+H]$^+$=409.8), calcd mass 407.03.

(RS)-2-(2-(4-(3,4-dichlorophenyl)thiazol-2-yl)hydrazinyl)-3-(2-nitrophenyl) Propanoic acid 6b: $^1$HNMR (400 MHz, DMSO-d$_6$) δ 3.10 (dd, J=13.6, 9.2 Hz, 1H), 3.27 (dd, J=13.6, 6 Hz, 1H), 3.64 (m, 1H), 5.87 (s, bs, 1H), 7.24 (s, 1H), 7.54 (m, 3H), 7.68 (m, 2H), 7.98 (m, 2H) 8.71 (s, 1H), 12.85 (s, bs, 1H). $^{13}$C-NMR δ 33.75 (CHCH$_2$), 64.03 (CHCH$_2$), 105.822 (CH), 125.14, 126.07, 127.66, 128.75, 129.96, 131.39, 131.95, 133.14, 133.73, 134.19, 136.23, 148.65 (CNO$_2$), 149.99, 174.38, 175.02 (CO$_2$H). MS$^+$(ESI) m/z=452.86 ([M+H]$^+$=453.89), calcd mass 452.01.

Synthesis of (Z/E)-2-(2-(4-(3,4-dichlorophenyl)thiazol-2-yl)hydrazono)-2-(2-nitrophenyl)acetic acid: KY-782-batch B

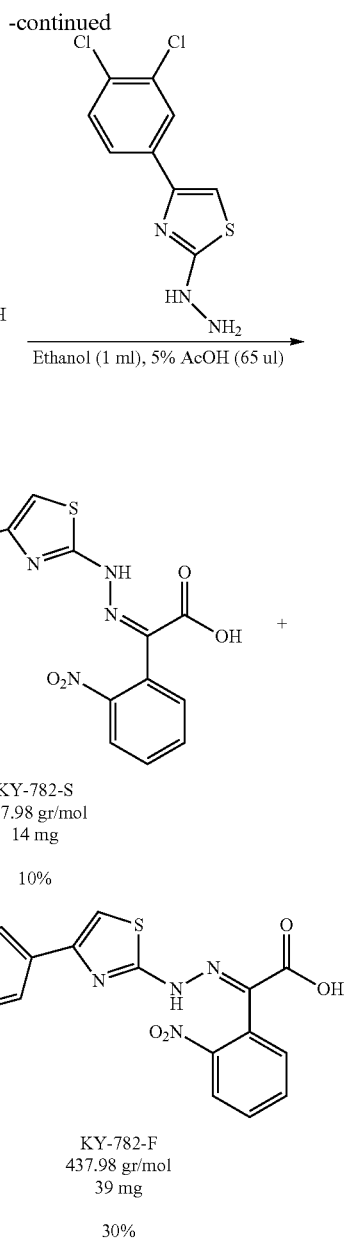

KY-780-batch B

KY-782-S
437.98 gr/mol
14 mg

10%

KY-782-F
437.98 gr/mol
39 mg

30%

Synthesis of (R,S)-2-hydroxy-2-(2-nitrophenyl)acetonitrile: KY-771-batch Sodium bisulfite (2.47 gr) was added to a suspension of 2-nitrobenzaldehyde 1 (3 gr, 19.86 mmol) in water (18 ml). After the reaction mixture had stirred for 10 min, it was cooled in ice water. A solution of potassium cyanide (1.548 gr, 23.77 mmol, dissolved in 9 ml water) was added dropwise. The mixture was stirred for 5 h, warmed to room temperature, and filtered. The solid was washed with water and dried to give 2.6 gr (73%).

(R,S)-2-hydroxy-2-(2-nitrophenyl)acetonitrile: KY-771-batch B $^1$HNMR (400 MHz, CDCl$_3$) δ 3.73 (s, 1H), 6.19 (s, 1H), 7.65 (m, 1H), 7.8 (m, 1H), 7.98 (dd, 1H), 8.2 (dd, 1H). $^{13}$C-NMR δ 60.92 (CHCN), 117.54, 126.10, 129.70, 130.93, 131.14, 135.11, 147.45 (CNO$_2$). MS$^+$(ESI) m/z ([M+Na+]=200.91), calcd mass 178.04.

Synthesis of (R,S)-2-hydroxy-2-(2-nitrophenyl)acetic acid: KY-778-batch B 2-hydroxy-2-(2-nitrophenyl) acetonitrile, KY-771-batch B (1.2 gr, 6.74 mmol) was reflux in concentrated hydrochloride acid (12 ml) for 3 h. the solution was diluted with water (30 ml) and continuously extracted with ether 3 days. The extract was dried Na$_2$SO$_4$ and evaporated to give 1.3 gr (98%).

$^1$H NMR (400 MHz, Aceton-d$_6$) δ 5.4 (s, bs, 1H), 5.92 (s, 1H), 7.61-7.63 (m, 1H), 7.75-7.79 (m, 1H), 7.90-7.92 (m, 1H), 8.01-8.03 (m, 1H). $^{13}$C-NMR δ 69.53, 124.73, 129.23, 129.34, 133.51, 134.65, 148.55, 171.92.

Synthesis of 2-(2-nitrophenyl)-2-oxoacetic acid: KY-780-batch B KMnO$_4$ (0.168 gr) was added to the cooled (ice water) solution of 2-hydroxy-2-(2-nitrophenyl)acetic acid (0.3 gr, 4.1 mmol), NaOH (70 mg) in water 6 ml. the mixture reaction was stirred for 2 h at 0° c. The mixture reaction was concentrated in vacuum and The residue was purified on C18-reversed phase flash chromatography column employing a linear gradient of 0-30% A in B (flow-rate 40 mL/min), where A is 0.1% formic acid in CH$_3$CN and B is 0.1% of formic acid in water, yielding 80 mg (10%) of pure KY-780-batch B 2-(2-nitrophenyl)-2-oxoacetic acid: KY-780-batch B $^1$HNMR (400 MHz, DMSO-d$_6$) δ 7.73 (d, J=8 Hz, 1H), 7.82-7.86 (m, 1H), 7.92-7.96 (m, 1H), 8.21-8.23 (d, J=8 Hz, 1H). $^{13}$C-NMR δ 124.57, 130.82, 133.34, 133.74, 135.97, 147.82, 161.33, 186.66.

Synthesis of (Z/E)-2-(2-(4-(3,4-dichlorophenyl)thiazol-2-yl)hydrazono)-2-(2-nitrophenyl)acetic acid: KY-782-batch B 2-(2-nitrophenyl)-2-oxoacetic acid (60 mg, 0.3 mmol) in 5% acetic acid 65 ul was added in to solution of [4-(3,4-Dichloro-phenyl)-thiazol-2-yl]-hydrazine (80 mg, 0.3 mmol) in ethanol 1 ml. the reaction mixture was stirred at 90° C. for 1 h. The LC-MS assay showed two isomer E/Z the ratio between two isomers. The residue was purified on silica gel-flash chromatography column employing a linear gradient of 0-20% A in B (flow-rate 40 mL/min), where A is MeOH and B is DCM, yielding (Z)-KY-782 (39 mg, 30%), (E)-KY-782 (14 mg, 10%) of pure.

(Z)-2-(2-(4-(3,4-dichlorophenyl)thiazol-2-yl)hydrazono)-2-(2-nitrophenyl)acetic acid: (Z)-KY-782 $^1$HNMR (400 MHz, DMSO-d$_6$) δ 7.49-7.55 (m, 3H), 7.622-7.64 (m, 1H), 7.69-7.72 (m, 1H), 8.849 (dd, J=1.84, 8.4 Hz, 1H), 7.90 (d, 8 Hz, 1H), 8.082 (d, J=1.64 Hz, 1H), 15.87 (s, 1H). $^{13}$C-NMR δ 106.93, 123.96, 126.37, 127.85, 129.19, 130.34, 131.48, 132.03, 132.10, 133.48, 133.98, 135.89, 143.50, 148.76, 150.10, 164.62, 168.66. MS$^+$(ESI) m/z ([M+H]$^+$=436.79), calcd mass 435.98.

(E)-2-(2-(4-(3,4-dichlorophenyl)thiazol-2-yl)hydrazono)-2-(2-nitrophenyl)acetic acid: (E)-KY-782 $^1$HNMR (400 MHz, DMSO-d$_6$) δ 7.59-7.62 (m, 3H), 7.75-7.77 (m, 3H), 8.01-8.03 (m, 1H), 8.12-822 (m, 1H), 11.17 (s, 1H). MS$^+$ (ESI) m/z ([M+H]$^+$=436.74), calcd mass 435.98.

Synthesis of (E/Z)-2-(2-(4-(3,4-dichlorophenyl)thiazol-2-yl)hydrazono)-2-(3-nitrophenyl)acetic acid: KY-788-batch A, batch B

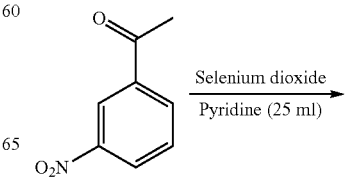

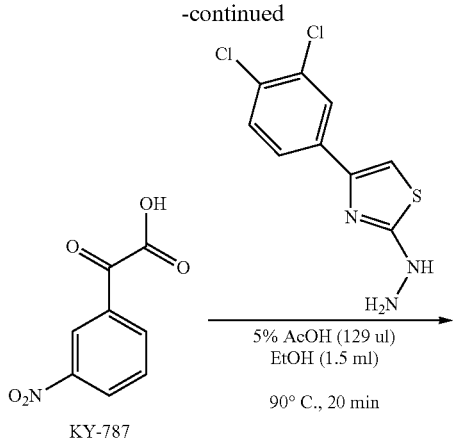

Hz, 1H), 8.66 (t, J=1.88, Hz, 1H). $^{13}$C-NMR δ 124.68, 129.42, 131.55, 134.31, 136.33, 148.6, 164.97, 186.66.

Synthesis of (E/Z)-2-(2-(4-(3,4-dichlorophenyl)thiazol-2-yl)hydrazono)-2-(3-nitrophenyl)acetic acid: KY-788 2-(3-nitrophenyl)-2-oxoacetic acid (120 mg, 0.61 mmol) in 5% acetic acid 129 ul was added in to solution of [4-(3,4-Dichloro-phenyl)-thiazol-2-yl]-hydrazine (160 mg, 0.61 mmol) in ethanol 1.5 ml. the reaction mixture was stirred at 90° C. for 1 h. The LC-MS assay showed two isomers E, Z with the ratio between two isomers (E/Z, 1:2). The residue was purified on C18 reversed phase flash chromatography column employing a linear gradient of 0-30% A in B (flow rate 40 ml/min), were A is 10% NH$_4$OH in CH$_3$CN and B is water, yielding (E)-KY-788 (50 mg, 18%), (Z)-KY-788 (76 mg, 28%) of pure KY-788.

(E)-2-(2-(4-(3,4-dichlorophenyl)thiazol-2-yl)hydrazono)-2-(3-nitrophenyl)acetic acid: (E)-KY-788 $^1$HNMR (400 MHz, DMSO-d$_6$) δ 7.63 (d, J=6.8 Hz 3H), 7.66 (s, 1H), 7.8-7.7 (m, 3H), 8.04 (d, J=1.56 Hz, 1H), 8.21 (s, 1H), 8.28-8.3 (m, 1H), 12.35 (s, 1H). $^{13}$C-NMR δ 108.82, 124.56, 125.20, 126.19, 127.88, 130.58, 130.81, 1351.59, 132.16, 133.87, 136.72, 148.67, 165.16. MS$^+$(ESI) m/z ([M+H]$^+$= 437), calcd mass 435.98.

(Z)-2-(2-(4-(3,4-dichlorophenyl)thiazol-2-yl)hydrazono)-2-(3-nitrophenyl)acetic acid: (Z)-KY-788 $^1$HNMR (400 MHz, DMSO-d$_6$) δ 7.02-7.27 (4H, NH4), 7.59-7.64 (m, 3H), 7. (dd, J=2, 8.4 Hz), 8.08 (d, J=2 Hz, 1H), 8.11-8.13 (m, 1H), 8.27 (d, J=7.84 Hz, 1H), 8.76 (t, J=2 Hz, 1H), 15.3 (s, 1H). $^{13}$C-NMR δ 107.44, 122.76, 123.49, 126.36, 127.87, 129.76, 130.433, 131.48, 132.13, 134.97, 135.73, 139.47, 140.63, 148.11, 148.73, 163.7, 169.01. MS$^+$(ESI) m/z ([M+H]$^+$= 437), calcd mass 435.98.

Synthesis of {[4-(3,4-Dichloro-phenyl)-thiazol-2-yl]-hydrazono}-(1H-indol-3-yl)-acetic acid: KY-689

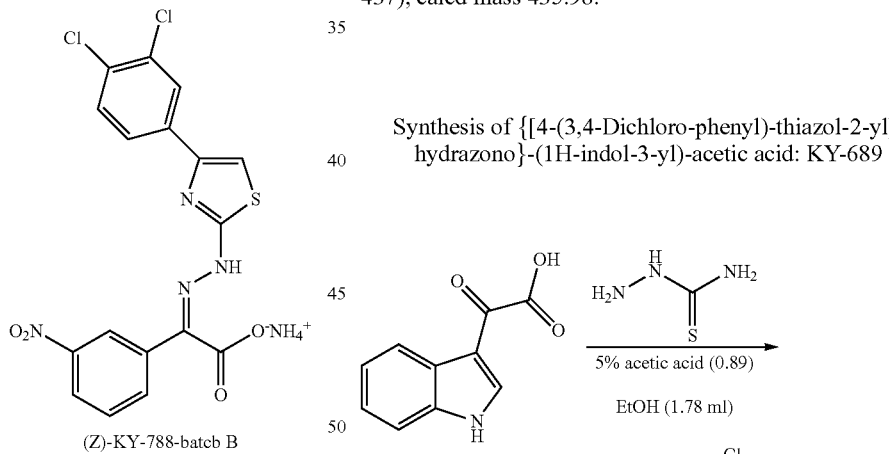

Synthesis of 2-(3-nitrophenyl)-2-oxoacetic acid: KY-787 1-(3-nitrophenyl)ethanone (1 gr, 6.05 mmol) and selenium dioxide (1 gr, 9 mmol) in 25 ml Pyridine were heated to 100° C. for overnight. The selenium was filtered. The solution was acidified with concentration HCl and extracted with three 50 ml portions of ethyl acetate. The combined organic layers were washed with 50 ml of brine, dried over anhydrous MgSO$_4$ and filtered, and the solvent was removed in vacuum. The residue was purified on C18 reversed phase flash chromatography column employing a linear gradient of 0-30% A in B (flow rate 40 ml/min), were A is 0.1% formic acid in CH$_3$CN and B is 0.1% of formic acid in water, yielding 0.8 gr (67%) of pure KY-787. $^1$HNMR (400 MHz, DMSO-d$_6$) δ 7.83-7.87 (m, 1H), 8.35 (d, J=8 Hz, 1H), 8.51 (dd, J=2.8, 8

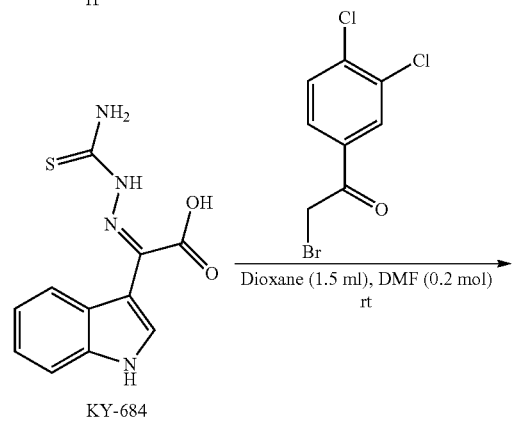

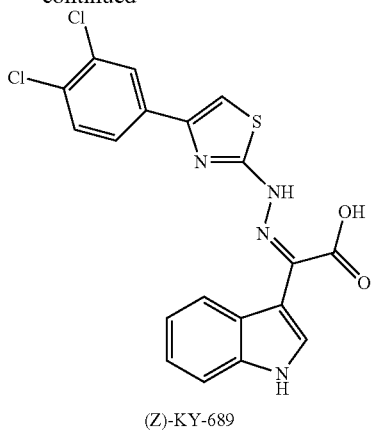

(Z)-KY-689

Synthesis of Hydrazono thiosemicarbazide-(1H-indol-3-yl)-acetic acid: KY-684(1H-Indol-3-yl)-oxo-acetic acid (0.8 g, 4.22 mmol) in 5% acetic acid 0.89 was added in to solution of thiosemicarbazide (0.389 gr, 4.2 mmol) in ethanol 1.78 ml. the reaction mixture was stirred at 90° C. for 30 min and cooled to room temperature. The yellow solid was precipitated out, filtered and washed by water. MS⁺(ESI) m/z ([M+H]⁺=263.03), calcd mass 262.29.

Synthesis of {[4-(3,4-Dichloro-phenyl)-thiazol-2-yl]-hydrazono}-(1H-indol-3-yl)-acetic acid: KY-689 A solution of a Hydrazono thiosemicarbazide-(1H-indol-3-yl)-acetic acid: KY-684 (200 mg, 0.76 mmol) and bromo-ethanone (0.204 gr, 0.76 mmol) in Dioxane (1.5 ml), DMF (0.2 ml) was stirred at room temperature for ON. The precipitate compound was (one isomer, the second isomer was at the solution) filtered and washed with Dioxane. Yield 320 mg (97%). MS⁺(ESI) m/z 431.3, calcd mass 430.84.

Synthesis of (Z/E)-2-(2-(4-(3,4-dichlorophenyl)thiazol-2-yl)hydrazono)-3-(1H-indol-3-yl)propanoic acid: KY-753

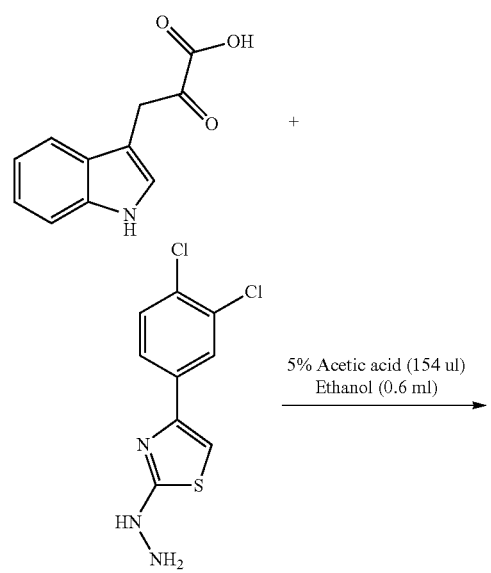

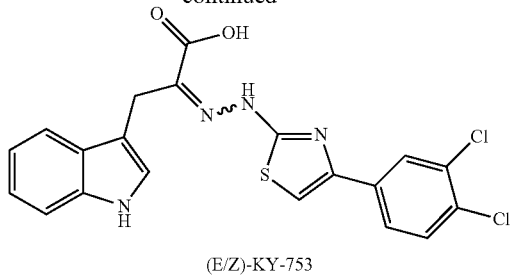

(E/Z)-KY-753

3-(1H-indol-3-yl)-2-oxopropanoic acid (150 mg, 0.738 mmol) in 5% acetic acid 154 ul was added in to solution of [4-(3,4-Dichloro-phenyl)-thiazol-2-yl]-hydrazine (0.19 gr, 0.738 mmol) in ethanol 0.6 ml. The reaction mixture was stirred at 90° C. for 1 h then cooled to room temperature. The yellow solid was precipitated out, filtered and washed by water (precipitated two isomers, E and Z). Yield 160 mg (160%). MS⁺(ESI) m/z 444.93, calcd mass 444.04.

Synthesis of ammonium (E)-2-(2-(4-(3,4-dichlorophenyl)thiazol-2-yl)hydrazono)-3-(4-(pyridin-2-yl)-1H-1,2,3-triazol-1-yl)propanoate: KY-767-batch-A

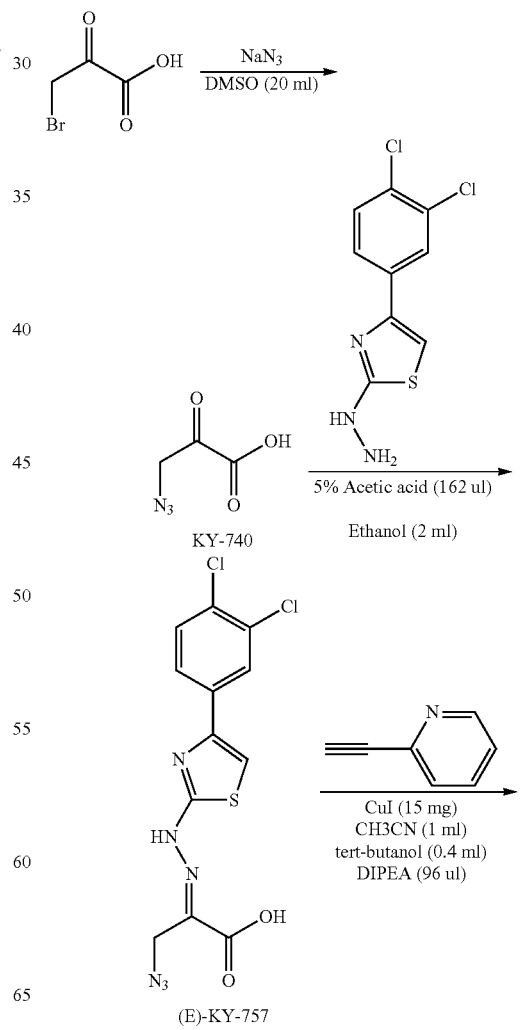

(E)-KY-757

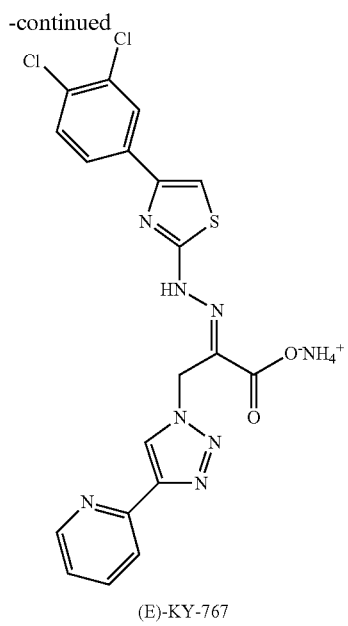

(E)-KY-767

Synthesis of 3-azido-2-oxopropanoic acid: KY-740 3-bromo-2-oxopropanoic acid (1.66 gr, 10 mmol) was added to a solution of sodium azide (0.715 gr, 11 mmol) in DMSO (20 ml) which was prepared by stirring the sodium azide in DMSO at room temperature for 40 min. the mixture reaction was stirred for 2 h at room temperature. It was quenched with water (50 ml). The mixture was extracted with $Et_2O$ (3×100 ml). The combined organic layers were washed with water, dried with $Na_2SO_4$, filtered, and concentrated in vacuo. Yield 1.1 gr (85%). $^1$HNMR (400 MHz, DMSO-$d_6$) δ 6.3 (s, 2H). $^{13}$C-NMR δ 113.52, 136.31, 165.3.

Synthesis of (E)-3-azido-2-(2-(4-(3,4-dichlorophenyl)thiazol-2-yl)hydrazono) propanoic acid: KY-757 3-azido-2-oxopropanoic acid, KY-740 (100 mg, 0.77 mmol) in 5% acetic acid 162 ul was added in to solution of [4-(3,4-Dichloro-phenyl)-thiazol-2-yl]-hydrazine (0.2 gr, 0.77 mmol) in ethanol 2 ml. the reaction mixture was stirred at room temperature for 5 h. and then cooled to room temperature. The yellow solid was precipitated out, filtered and washed by water. Yield 0.1 gr (35%). MS$^+$(ESI) m/z 371.91, calcd mass 371.2.

Synthesis of ammonium (E)-2-(2-(4-(3,4-dichlorophenyl)thiazol-2-yl)hydrazono)-3-(4-(pyridin-2-yl)-1H-1,2,3-triazol-1-yl)propanoate: KY-767-batch-A To a solution of (E)-3-azido-2-(2-(4-(3,4-dichlorophenyl)thiazol-2-yl)hydrazono) propanoic acid (E)-KY-757, (100 mg) in $CH_3CN$ 1 ml, tert-butanol 0.4 ml was added diisopropylethylamine 96 ul followed by 2-ethynylpyridine (0.4 mmol, 41 ul), CuI (15 mg). The reaction stirred at rt for 3 h. LC-MS assay showed two isomers. The solvent was removed under pressure. The residue was purified on C18 reversed phase flash chromatography column employing a linear gradient of 0-30% A in B (flow rate 40 ml/min), were A is 10% $NH_4OH$ in $CH_3CN$ and B is water, yielding (14 mg, 18%) of pure (E)-KY-788. MS$^+$ (ESI) m/z 373.91, calcd mass 473.85.

EXAMPLE XII

Fluorescent Polarization Assay

Representative compounds were analyzed by fluorescent polarization, according to the method of Moerke et al., Small Molecule Inhibition of the Interaction Between the Translation Initiation Factors eIF4E and eIF4G, Cell, 2007; 128:257-267 hereby incorporated by reference in its entirety, for their ability to inhibit binding of an eIF4G peptide to recombinant eIF4E in a homogenous format. Briefly an 18 amino acid FITC labeled 4G peptide as described in Cell, 2007; 128:257-267 is incubated in the presence or absence of eIF4G and the fluorescent polarization is measured. The difference between the two measurement yields net polarization which is considered full signal of the assay (100% control). To determine if a compound inhibits eIF4E/eIF4G interaction, the FITC labeled peptide, recombinant eIF4E and various concentration of test compounds are mixed, incubated for minimum of 15 minutes and fluorescent polarization signal is read in a microplate plate reader capable of recording polarized signal. The activity of compound at each concentration is determined by comparing the fluorescent polarization (FP) signal in the presence of compound to the control (no compound) value. The percent inhibition is =100-((FP compound/FP control)*100).

EXAMPLE XIII

SRB Assay

A sulfur rhodamine B (SRB) assay was used to determine the extent of inhibition of cell proliferation as a measure of the anti-cancer activity of compounds of the present disclosure. The reagent SRB binds to cellular proteins and absorbs light proportionally to the cellular protein content, which is a surrogate marker for the number of cells. According to aspects of the present disclosure, the assay can be used to with any cancer cell line including breast cancer cell lines, prostate cancer cell lines, melanoma cell lines, lung cancer cell lines or any other cell lines of the cancers described herein.

The following protocol was used to determine the growth characteristics of certain cell lines CRL2351 human breast cancer and CRL2813 human melanoma from which cell lines having doubling times less than 48 hours were selected for growth inhibition experiments. It is to be understood that CRL2351 human breast cancer and CRL2813 human melanoma were selected as being representative of cancer cell lines and that one of skill in the art can readily select other cell lines, including cancer cell lines for the many cancers described herein, exhibiting abnormal proliferation in which to demonstrate the ability of the compounds of the present invention to inhibit cellular proliferation. The following materials were used in addition to the cancel cell lines: complete (5% fetal calf serum added) tissue culture media, 96-well tissue culture plates, Sulforhodamine B dye (SRB, 0.57% w/w), tricarbocilicacetic acid (TCA, 10%), acetic acid glacial (1%) and 10 mM Tris base. The cells were prepared and plated. Cancer cells were grown to 80% confluency in an incubator. The cells were trypsinized per standard protocol or as needed for each cell line. The trypsin was neutralized, cells dissociated and counted. Each cell line was plated at a density of 500, 1000 and 3000 cells per well (six wells each) in five separate plates. The cells were then returned to the incubator. One plate was then removed each day starting day one after plating. 100 μl of 10% TCA was then added and the cells were fixed at 4° C. until all the cells were fixed. The cells were then stained with sulfur rhodamine B according to the method of Vichai and Kirtikara, Nature Methods 2006, 1:1112-1115 incorporated herein by reference in its entirety. All plates are washed and stained by sulphorhodamine B dye, excess dye is washed, bound dye is solubilized and quantified at 510 nM in a multi-well plate reader. The cell growth for vehicle treatment is considered to be 100%. The optical density was then measured and plotted for each starting cell number and cell line against time. The percent cell growth inhibition was calculated as 100 minus the % of control cell growth. The % of control cell growth=((mean OD sample−Mean OD day 0)/(mean OD vehicle−Mean OD day 0))*100.

The following Table shows the summary evaluation of various representative compounds for their ability to inhibit eIF4E/eIF4G interaction and to inhibit proliferation of cancer cell lines.

| Code | Structure | IC$_{50}$ [μM] | | Fp |
|------|-----------|----------------|---|-----|
| | | CRL2813 | CRL2351 | (ratio to Z) |
| KH-102BII | | >20 | 9.0 | 0.69 |
| KH-102BIIs | | 20.5 | 18 | 0.69 |
| KH-113s | | 12.6 | 12.0 | 1.05 |

-continued
| Code | Structure | IC₅₀ [μM] CRL2813 | CRL2351 | Fp (ratio to Z) |
|---|---|---|---|---|
| KH-148I | 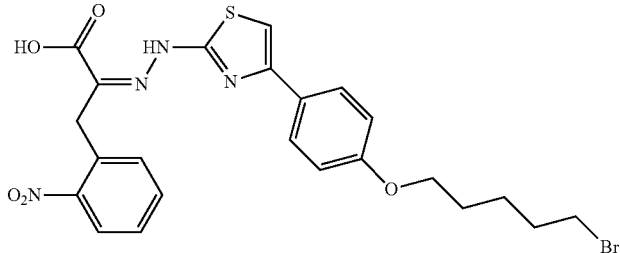 [SMILES: O=C(O)/C(Cc1ccccc1[N+](=O)[O-])=N\Nc1nc(-c2ccc(OCCCCCBr)cc2)cs1] | 0.9 | NT | 1.50 |
| KH-166 | 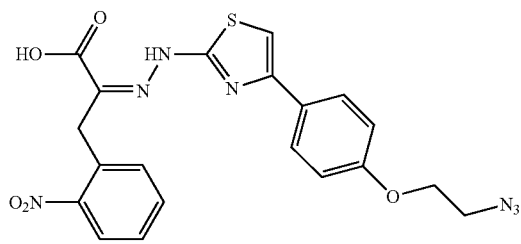 [SMILES: [N-]=[N+]=NCCOc1ccc(-c2csc(N/N=C(/Cc3ccccc3[N+](=O)[O-])C(=O)O)n2)cc1] | 9.0 | 5.0 | 0.80 |
| KH-167f<br>KH-167s | 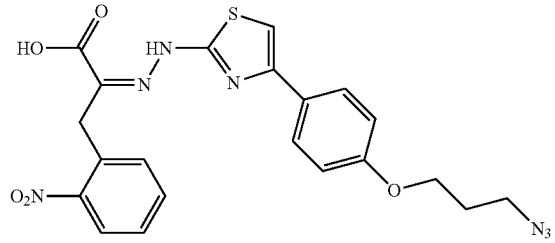 [SMILES: [N-]=[N+]=NCCCOc1ccc(-c2csc(N/N=C(/Cc3ccccc3[N+](=O)[O-])C(=O)O)n2)cc1] | 18.6<br>12.0 | >20<br>2.7 | 1.04<br>0.91 |
| KH-168S | 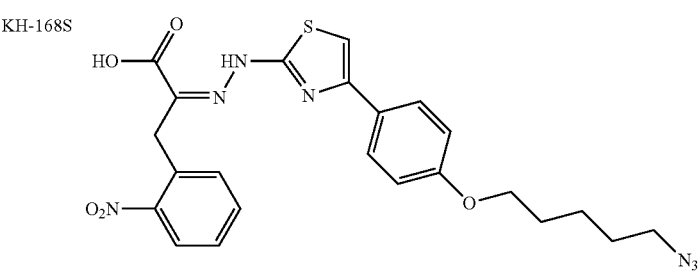 | 16.0 | >20 | 1.29 |
| KH-170 | 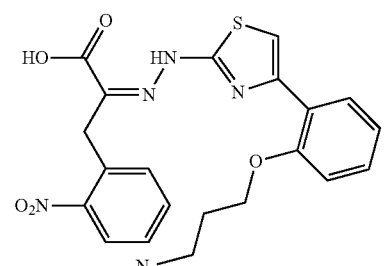 | 14.5 | 0.8 | 0.92 |

-continued

| Code | Structure | IC$_{50}$ [μM] | | Fp |
| --- | --- | --- | --- | --- |
| | | CRL2813 | CRL2351 | (ratio to Z) |
| KH-174 | 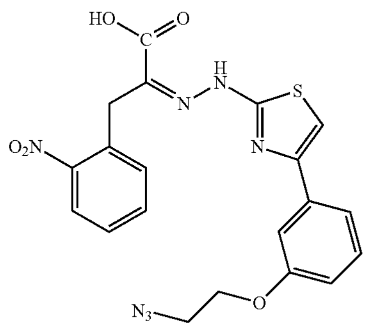 [SMILES: [N-]=[N+]=NCCOc1cccc(-c2csc(N/N=C(/Cc3ccccc3[N+](=O)[O-])C(=O)O)n2)c1] | 11 | 1.2 | 0.82 |
| KH-287II-S | 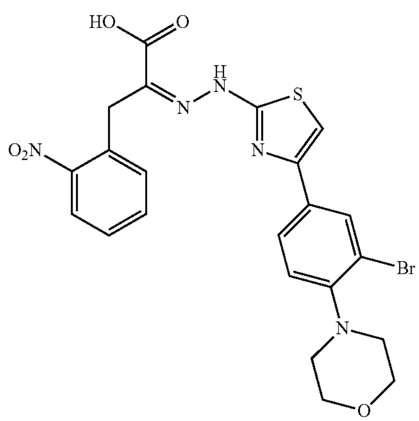 [SMILES: O=C(O)/C(Cc1ccccc1[N+](=O)[O-])=N\Nc1nc(-c2ccc(N3CCOCC3)c(Br)c2)cs1] | NT | NT | 0.62 |
| KH-332S | 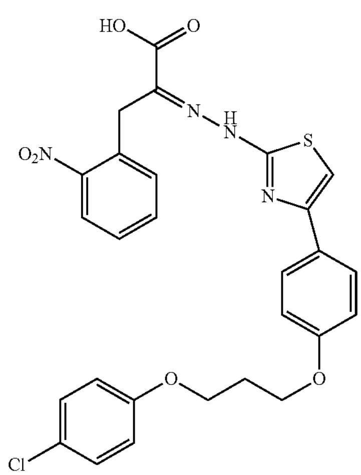 [SMILES: O=C(O)C(Cc1ccccc1[N+](=O)[O-])=NNc1nc(-c2ccc(OCCCOc3ccc(Cl)cc3)cc2)cs1] | NT | NT | 1.09 |

-continued

| Code | Structure | IC$_{50}$ [μM] CRL2813 | CRL2351 | Fp (ratio to Z) |
|------|-----------|------------------------|---------|-----------------|
| KH-333S | 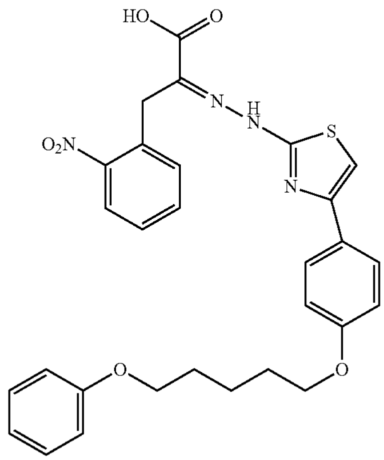 [SMILES: O=C(O)C(Cc1ccccc1[N+](=O)[O-])=NNc1nc(-c2ccc(OCCCCCOc3ccccc3)cc2)cs1] | NT | NT | 0.96 |
| KH-336S | 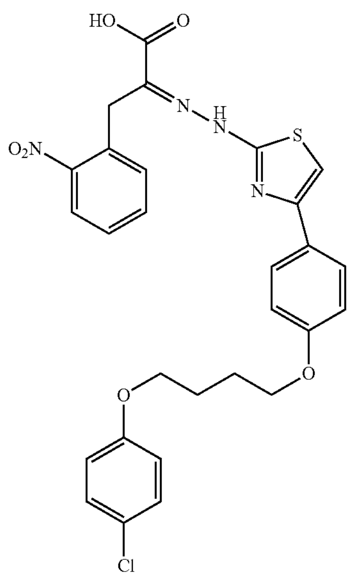 [SMILES: O=C(O)C(Cc1ccccc1[N+](=O)[O-])=NNc1nc(-c2ccc(OCCCCOc3ccc(Cl)cc3)cc2)cs1] | NT | NT | 0.96 |
| KH-53S | 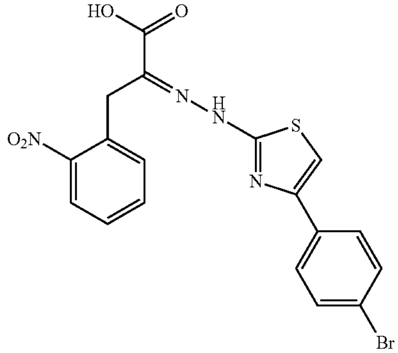 [SMILES: O=C(O)C(Cc1ccccc1[N+](=O)[O-])=NNc1nc(-c2ccc(Br)cc2)cs1] | NT | NT | 0.61 |

-continued

| Code | Structure | IC$_{50}$ [μM] CRL2813 | CRL2351 | Fp (ratio to Z) |
|---|---|---|---|---|
| KH-8 | 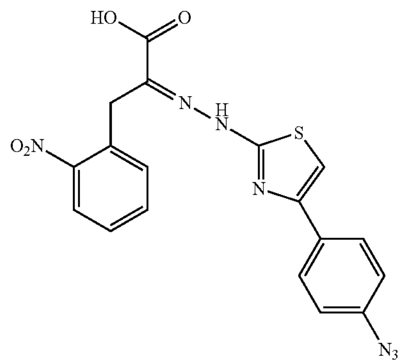 [SMILES: [N-]=[N+]=Nc1ccc(-c2csc(NN=C(Cc3ccccc3[N+](=O)[O-])C(=O)O)n2)cc1] | NT | NT | 0.99 |
| PC-159F | 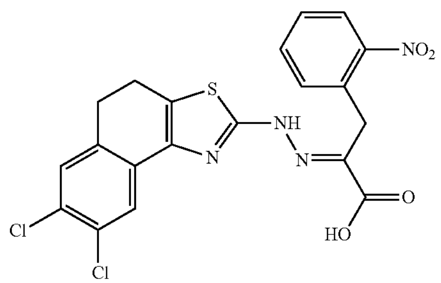 [SMILES: O=C(O)/C(Cc1ccccc1[N+](=O)[O-])=N/Nc1nc2c(s1)CCc1cc(Cl)c(Cl)cc1-2] | <1 | <1 | 1.05 |
| PC-159S | 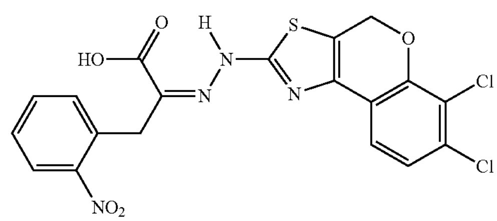 [SMILES: O=C(O)/C(Cc1ccccc1[N+](=O)[O-])=N\Nc1nc2c(s1)COc1c-2ccc(Cl)c1Cl] | 4 | 12.5 | 0.73 |
| PC-163F | 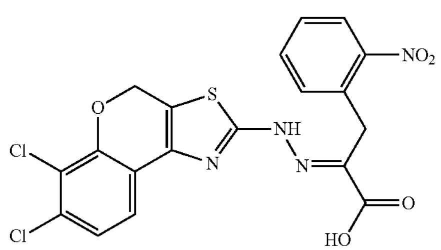 [SMILES: O=C(O)/C(Cc1ccccc1[N+](=O)[O-])=N/Nc1nc2c(s1)COc1c-2ccc(Cl)c1Cl] | <1 | <1 | 1.05 |
| PC-163S | 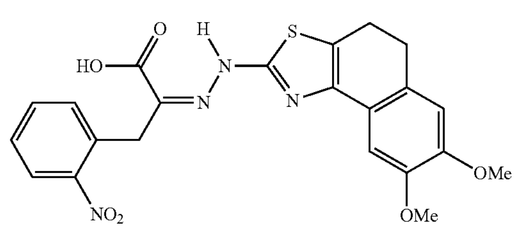 [SMILES: COc1cc2c(cc1OC)-c1nc(N/N=C(/Cc3ccccc3[N+](=O)[O-])C(=O)O)sc1CC2] | 3 | 3 | 1.26 |
| PC-195S | 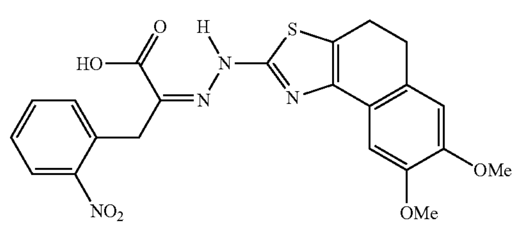 [SMILES: COc1cc2c(cc1OC)-c1nc(N/N=C(/Cc3ccccc3[N+](=O)[O-])C(=O)O)sc1CC2] | 7.5 | 4 | 0.83 |

|  |  | IC$_{50}$ [μM] | | Fp |
|---|---|---|---|---|
| Code | Structure | CRL2813 | CRL2351 | (ratio to Z) |
| PC-202F | | <1 | NA | 1 |
| PC-202S | | 4.5 | NA | 2 |
| PC-204F | | NA | 2 | 1.14 |
| PC-204S | | 3 | <1 | 1.71 |
| PC-218F | | 8 | <1 | 1.6 |
| PC-218S | | 3 | 5.5 | 5.33 |

-continued

| Code | Structure | IC$_{50}$ [μM] CRL2813 | CRL2351 | Fp (ratio to Z) |
|---|---|---|---|---|
| PC-227F | 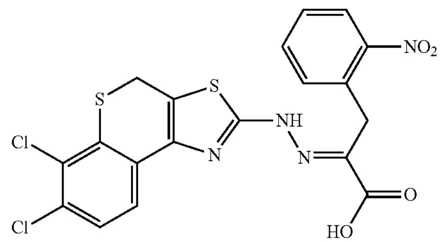 | NT | NT | 1.67 |
| PC-227S | 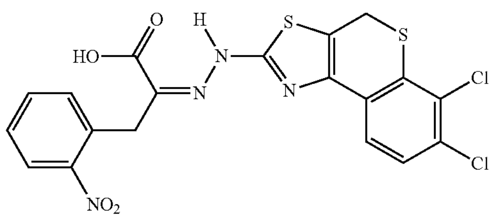 | NT | NT | NT |
| KY-323A | 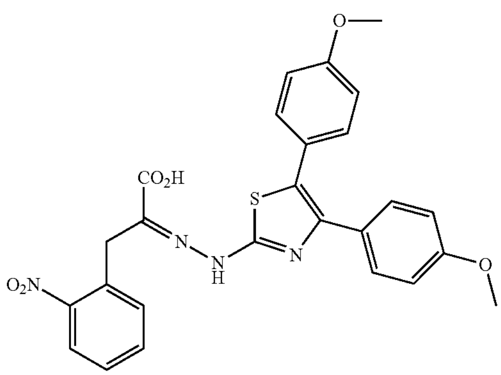 [SMILES: COc1ccc(-c2nc(NN=C(Cc3ccccc3[N+](=O)[O-])C(=O)O)sc2-c2ccc(OC)cc2)cc1] | 1* | 0.6 | 0.67 |
| KY-323B | 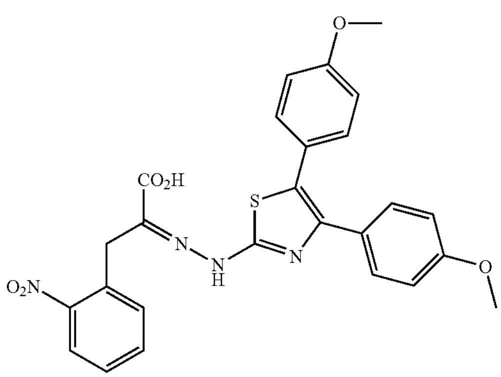 [SMILES: COc1ccc(-c2nc(NN=C(Cc3ccccc3[N+](=O)[O-])C(=O)O)sc2-c2ccc(OC)cc2)cc1] | 7 ± 2.6 | 20 ± 3.7 | 0.6 |

-continued

| Code | Structure | IC$_{50}$ [μM] CRL2813 | IC$_{50}$ [μM] CRL2351 | Fp (ratio to Z) |
|---|---|---|---|---|
| KY-341PRI | 5 ± 1.74 structure: 2-nitrobenzyl hydrazone with thiazole bearing 3,4-dimethoxyphenyl and 4-methoxyphenyl | 5 ± 1.74 | 4 ± 0.51 | 1.2 |
| KY-343PR | structure: 2-nitrobenzyl hydrazone with thiazole bearing 4-methoxyphenyl and 3,4-dimethoxyphenyl | >20 | >20 | 1 |
| KY-349PR | structure: 2-nitrobenzyl hydrazone with thiazole bearing 4-chlorophenyl and phenyl | >20 | >20 | 1 |
| KY-351PR | structure: 2-nitrobenzyl hydrazone with thiazole bearing 4-chlorophenyl and 4-methylphenyl | 3 | 2.5 | 1.1 |

-continued

| Code | Structure | IC$_{50}$ [μM] | | Fp (ratio to Z) |
| --- | --- | --- | --- | --- |
| | | CRL2813 | CRL2351 | |
| KY-353PR | 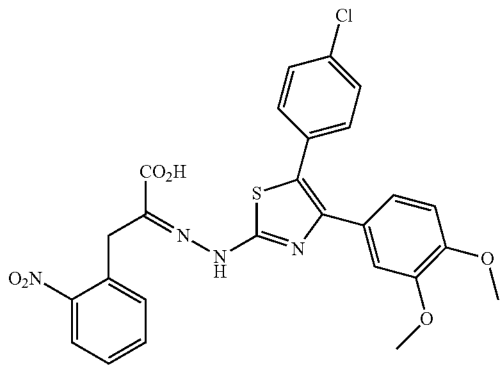 [SMILES: COc1ccc(-c2nc(NN=C(Cc3ccccc3[N+](=O)[O-])C(=O)O)sc2-c2ccc(Cl)cc2)cc1OC] | >20 | >20 | 0.7 |
| KY-355PR | 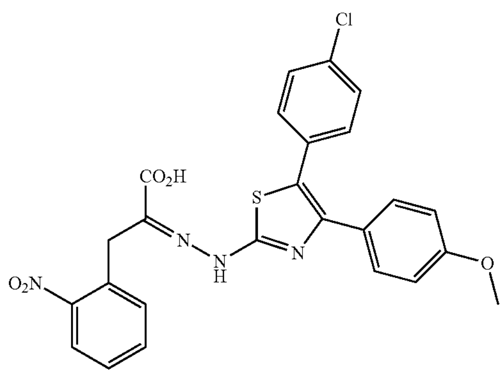 [SMILES: COc1ccc(-c2nc(NN=C(Cc3ccccc3[N+](=O)[O-])C(=O)O)sc2-c2ccc(Cl)cc2)cc1] | 3 ± 0.18 | >20 | 1.1 |
| KY-365$_{A22-B3}$ | | 3.3 | 3.2 | 0.85 |
| KY-371$_{A11-B1}$ | | 3 ± 0.5 | 16 ± 4.9 | 2.4 |

-continued

| Code | Structure | IC$_{50}$ [μM] | | Fp (ratio to Z) |
|---|---|---|---|---|
| | | CRL2813 | CRL2351 | |
| KY-383 | 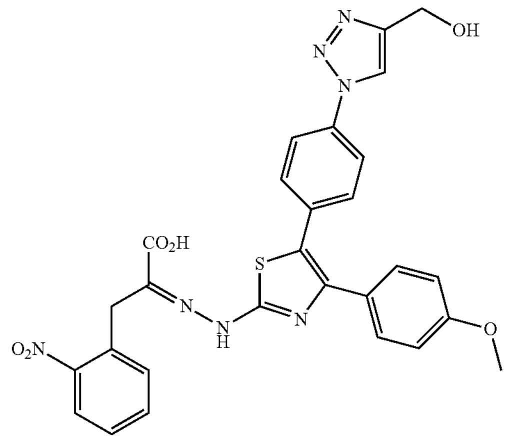 [SMILES: COc1ccc(-c2nc(NN=C(Cc3ccccc3[N+](=O)[O-])C(=O)O)sc2-c2ccc(-n3cc(CO)nn3)cc2)cc1] | 13 ± 3.6 | >20 | 2.3 |
| 4EGI-1 | 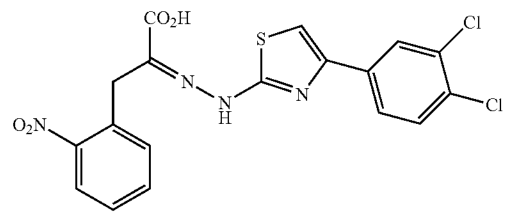 [SMILES: O=C(O)C(Cc1ccccc1[N+](=O)[O-])=NNc1nc(-c2ccc(Cl)c(Cl)c2)cs1] | 3.8 ± 1.06 | 5 ± 1.6 | 1 |
| EK-B2 | 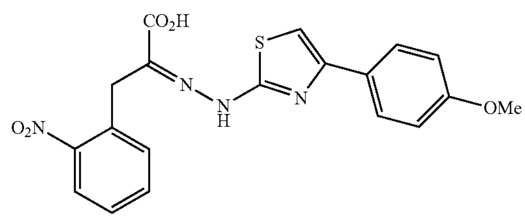 [SMILES: COc1ccc(-c2csc(NN=C(Cc3ccccc3[N+](=O)[O-])C(=O)O)n2)cc1] | 11 | 7 | 0.86 |
| KY-435-F | 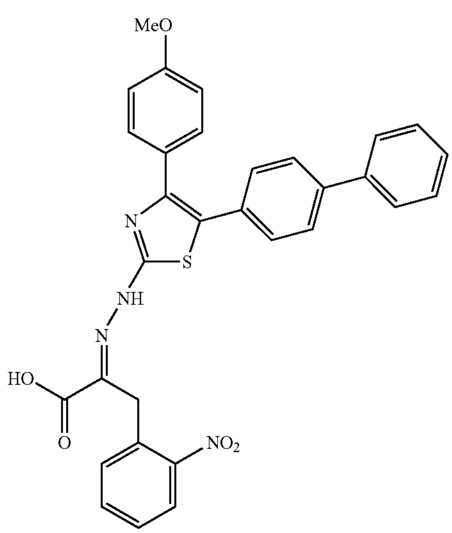 [SMILES: COc1ccc(-c2nc(N/N=C(\Cc3ccccc3[N+](=O)[O-])C(=O)O)sc2-c2ccc(-c3ccccc3)cc2)cc1] | 3 ± 0.56 | 2.8 ± 0.73 | 0.5 |

-continued

| Code | Structure | IC$_{50}$ [μM] CRL2813 | CRL2351 | Fp (ratio to Z) |
|---|---|---|---|---|
| KY-435-S | 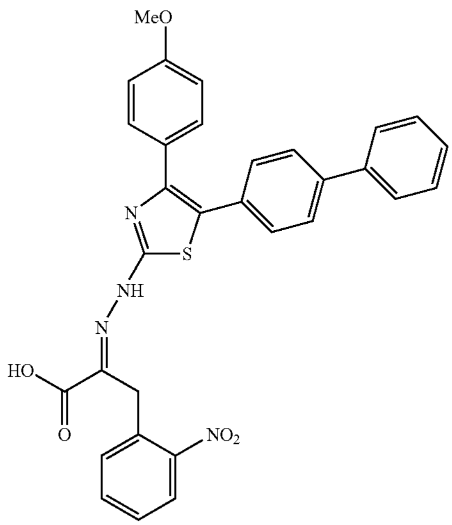 [SMILES: COc1ccc(-c2nc(N/N=C(\Cc3ccccc3[N+](=O)[O-])C(=O)O)sc2-c2ccc(-c3ccccc3)cc2)cc1] | <0.54 | <0.54 | 2 |
| KY-445 | 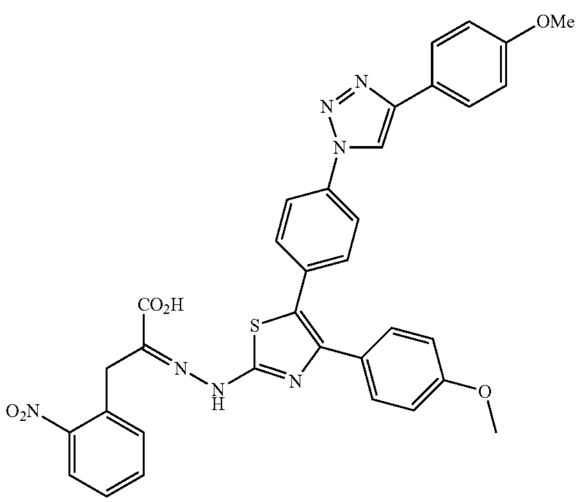 [SMILES: COc1ccc(-c2cn(-c3ccc(-c4sc(NN=C(Cc5ccccc5[N+](=O)[O-])C(=O)O)nc4-c4ccc(OC)cc4)cc3)nn2)cc1] | 13 ± 0.82 | >20 | 1 |
| KY-441 | 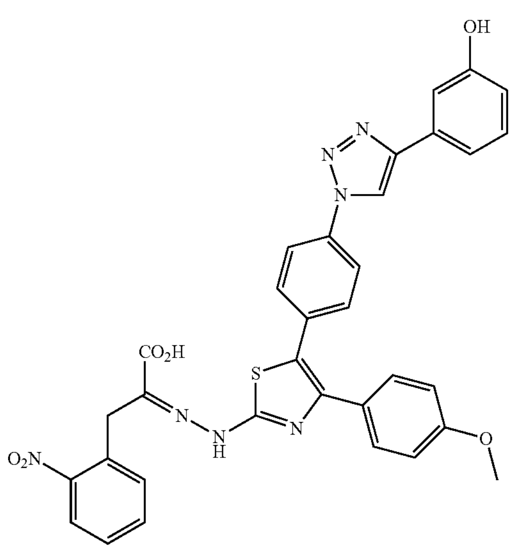 [SMILES: COc1ccc(-c2nc(NN=C(Cc3ccccc3[N+](=O)[O-])C(=O)O)sc2-c2ccc(-n3cc(-c4cccc(O)c4)nn3)cc2)cc1] | 15 ± 1.12 | >20 | 1.2 |

-continued

| Code | Structure | IC$_{50}$ [μM] CRL2813 | CRL2351 | Fp (ratio to Z) |
|---|---|---|---|---|
| KY-443$_{416-19}$ | | 14 ± 0.73 | >20 | 1 |
| KY-369S | 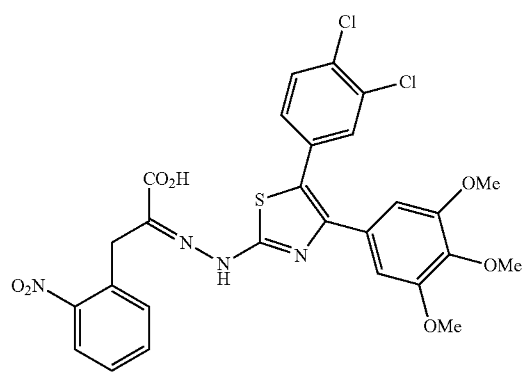 [SMILES: COc1cc(-c2nc(NN=C(Cc3ccccc3[N+](=O)[O-])C(=O)O)sc2-c2ccc(Cl)c(Cl)c2)cc(OC)c1OC] | 2 ± 0.19 | 0.6 ± 0.02 | 0.75 |
| KY-379S | 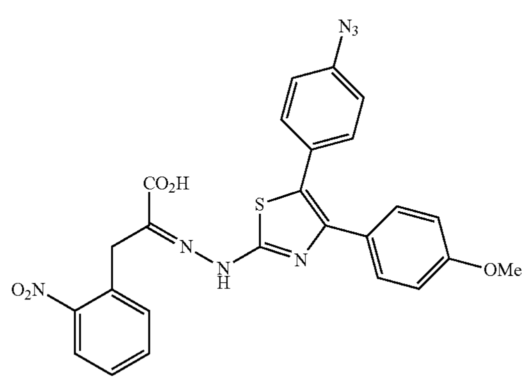 [SMILES: COc1ccc(-c2nc(NN=C(Cc3ccccc3[N+](=O)[O-])C(=O)O)sc2-c2ccc(N=[N+]=[N-])cc2)cc1] | 3 ± 0.2 | 1.2 ± 0.04 | 1.2 |

-continued
| Code | Structure | IC$_{50}$ [μM] | | Fp (ratio to Z) |
| --- | --- | --- | --- | --- |
| | | CRL2813 | CRL2351 | |
| KY-447 | 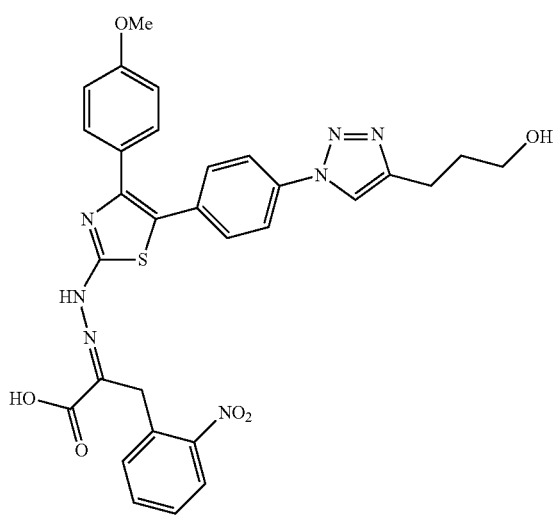 [SMILES: COc1ccc(-c2nc(NN=C(Cc3ccccc3[N+](=O)[O-])C(=O)O)sc2-c2ccc(-n3cc(CCCO)nn3)cc2)cc1] | 17 ± 1.29 | >20 | 1.5 |
| KY-449 | 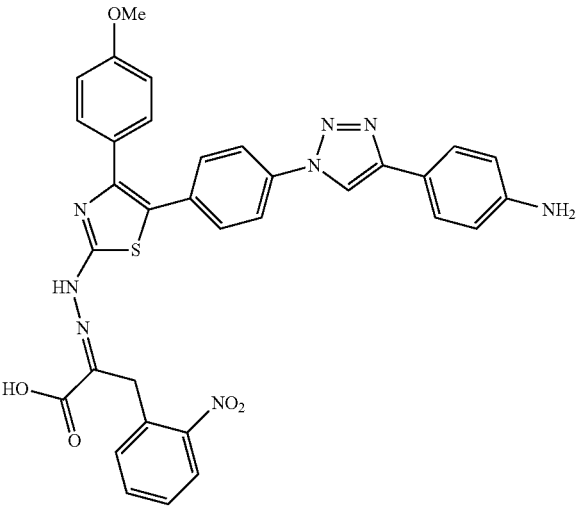 [SMILES: COc1ccc(-c2nc(NN=C(Cc3ccccc3[N+](=O)[O-])C(=O)O)sc2-c2ccc(-n3cc(-c4ccc(N)cc4)nn3)cc2)cc1] | 16 ± 1.8 | 17 | 2.5 |

| Code | Structure | IC$_{50}$ [μM] CRL2813 | CRL2351 | Fp (ratio to Z) |
|---|---|---|---|---|
| KY-467F | 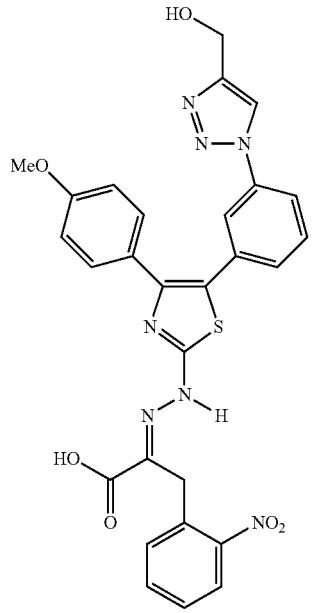 [SMILES: COc1ccc(-c2nc(N/N=C(\Cc3ccccc3[N+](=O)[O-])C(=O)O)sc2-c2cccc(-n3cc(CO)nn3)c2)cc1] | >20 | >20 | 0.7 |
| KY-467S | 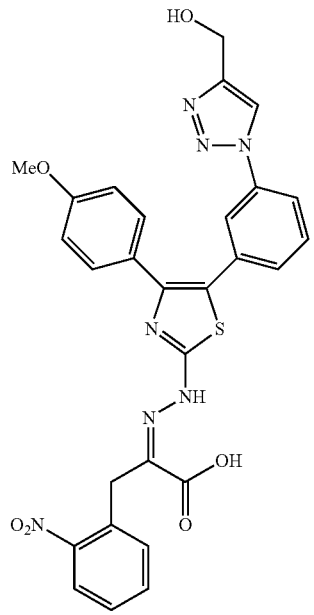 [SMILES: COc1ccc(-c2nc(N/N=C(/Cc3ccccc3[N+](=O)[O-])C(=O)O)sc2-c2cccc(-n3cc(CO)nn3)c2)cc1] | >20 | >20 | 0.85 |

-continued
| Code | Structure | IC₅₀ [μM] CRL2813 | CRL2351 | Fp (ratio to Z) |
|---|---|---|---|---|
| KY-576S | 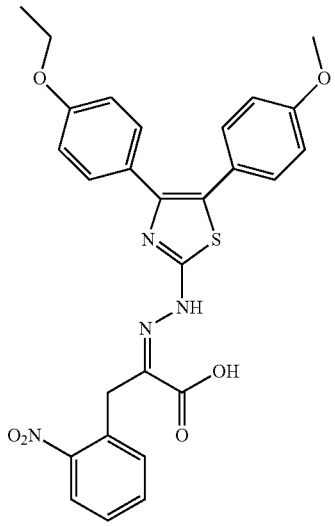 [SMILES: CCOc1ccc(-c2nc(N/N=C(/Cc3ccccc3[N+](=O)[O-])C(=O)O)sc2-c2ccc(OC)cc2)cc1] | 12.8 | >20 | 0.82 |
| KY-576F | 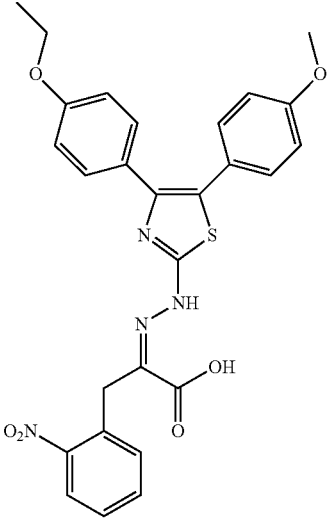 [SMILES: CCOc1ccc(-c2nc(N/N=C(/Cc3ccccc3[N+](=O)[O-])C(=O)O)sc2-c2ccc(OC)cc2)cc1] | 2 | 2 | 1 |
| KY-577S | 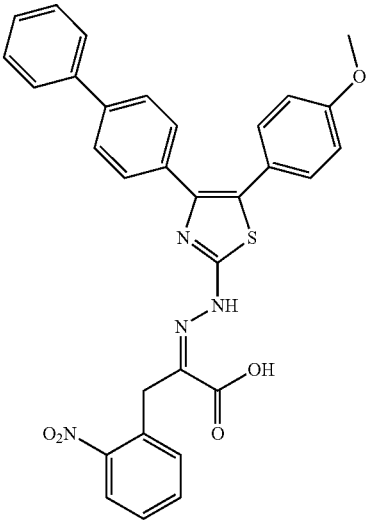 [SMILES: COc1ccc(-c2sc(N/N=C(/Cc3ccccc3[N+](=O)[O-])C(=O)O)nc2-c2ccc(-c3ccccc3)cc2)cc1] | 3.5 | 11.7 | 1 |

-continued

| Code | Structure | IC$_{50}$ [μM] | | Fp (ratio to Z) |
|---|---|---|---|---|
| | | CRL2813 | CRL2351 | |
| KY-577SF | 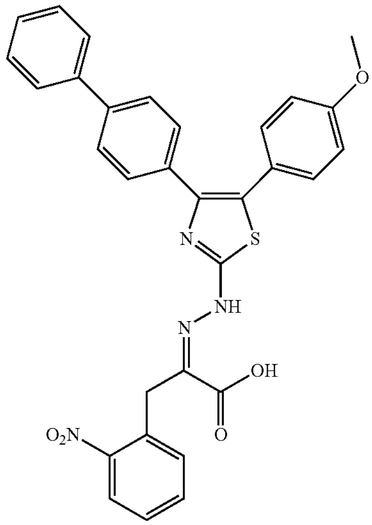 [SMILES: COc1ccc(-c2sc(N/N=C(/Cc3ccccc3[N+](=O)[O-])C(=O)O)nc2-c2ccc(-c3ccccc3)cc2)cc1] | 0.1 | 0.7 | 1 |
| KY-599S | 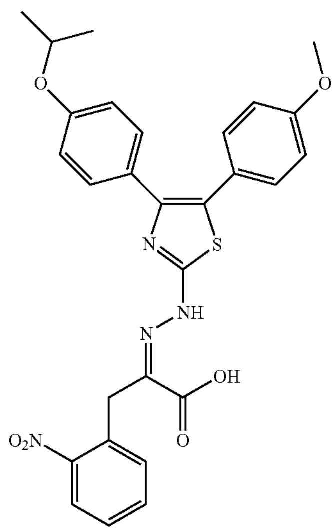 [SMILES: COc1ccc(-c2sc(N/N=C(/Cc3ccccc3[N+](=O)[O-])C(=O)O)nc2-c2ccc(OC(C)C)cc2)cc1] | 3 | 8.7 | 1.3 |
| KY-600 | 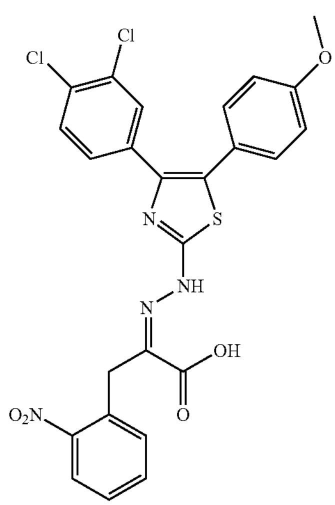 [SMILES: COc1ccc(-c2sc(N/N=C(/Cc3ccccc3[N+](=O)[O-])C(=O)O)nc2-c2ccc(Cl)c(Cl)c2)cc1] | 2.8 | 4.5 | 0.7 |

-continued

| Code | Structure | IC$_{50}$ [μM] CRL2813 | CRL2351 | Fp (ratio to Z) |
|---|---|---|---|---|
| KY-582S | 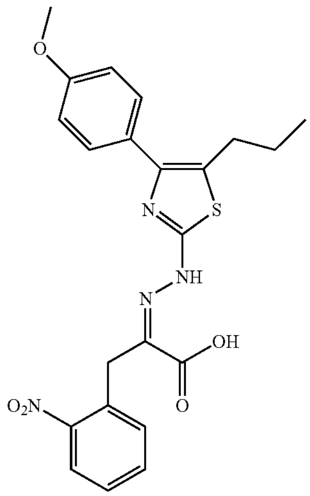 [SMILES: CCCc1sc(N/N=C(/Cc2ccccc2[N+](=O)[O-])C(=O)O)nc1-c1ccc(OC)cc1] | 11.6 | 13.2 | 0.9 |
| KY-611-pri-S | 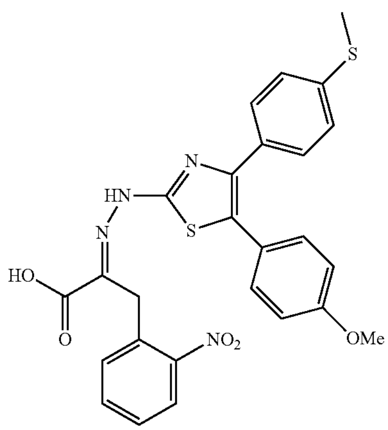 [SMILES: COc1ccc(-c2sc(N/N=C(\Cc3ccccc3[N+](=O)[O-])C(=O)O)nc2-c2ccc(SC)cc2)cc1] | 6.2 | 15.5 | 0.62 |
| KY-615S | 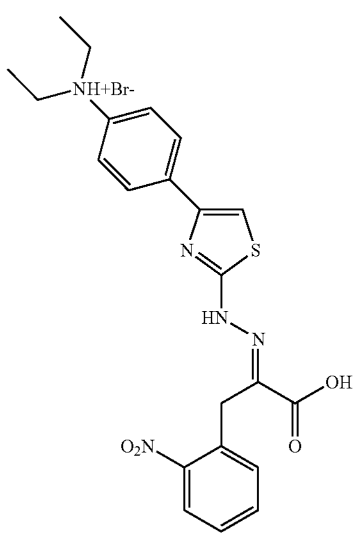 | 12.5 | >20 | 4 |

-continued

| Code | Structure | IC₅₀ [μM] | | Fp (ratio to Z) |
|---|---|---|---|---|
| | | CRL2813 | CRL2351 | |
| KY-615F | 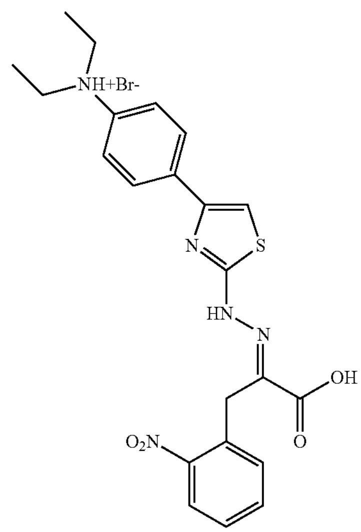 | 18.8 | 5.7 | NA |
| KY-627S | 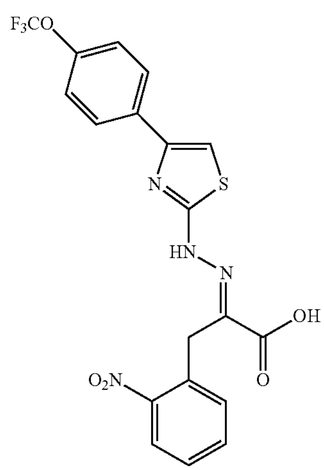 [SMILES: O=C(O)/C(Cc1ccccc1[N+](=O)[O-])=N/Nc1nc(-c2ccc(OC(F)(F)F)cc2)cs1] | >20 | >20 | 0.65 |
| KY-613S | 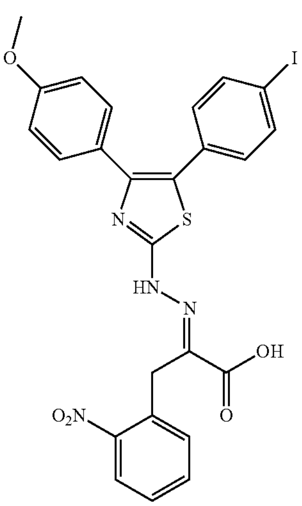 [SMILES: COc1ccc(-c2nc(N/N=C(\Cc3ccccc3[N+](=O)[O-])C(=O)O)sc2-c2ccc(I)cc2)cc1] | 2.7 | 9.5 | 1.1 |

-continued

| Code | Structure | IC$_{50}$ [µM] | | Fp (ratio to Z) |
| --- | --- | --- | --- | --- |
| | | CRL2813 | CRL2351 | |
| KY-365 | 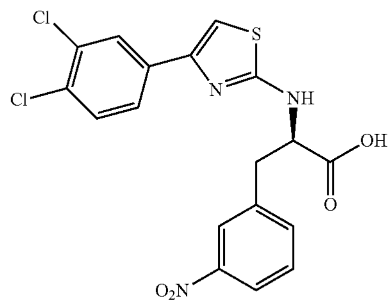 [SMILES: O=C(O)[C@@H](Cc1cccc([N+](=O)[O-])c1)Nc1nc(-c2ccc(Cl)c(Cl)c2)cs1] | | 3 | 0.82 |
| KY-680 | 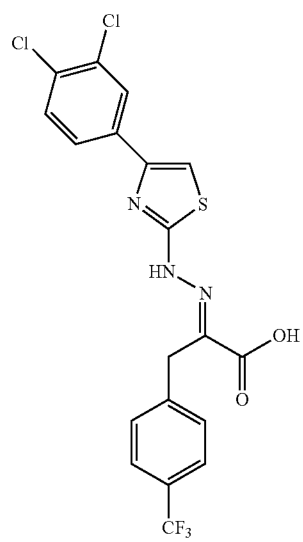 [SMILES: O=C(O)/C(Cc1ccc(C(F)(F)F)cc1)=N/Nc1nc(-c2ccc(Cl)c(Cl)c2)cs1] | 1 | 3 | 1.1 |
| KY-757-p | 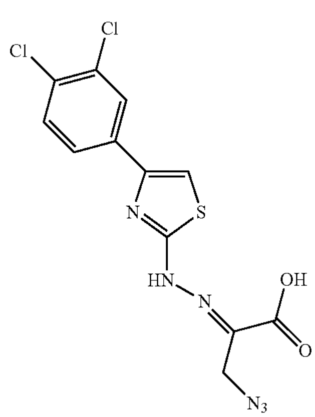 [SMILES: [N-]=[N+]=NC/C(=N\Nc1nc(-c2ccc(Cl)c(Cl)c2)cs1)C(=O)O] | >20 | >20 | 1 |

167                                                                                                              168
-continued

| Code | Structure | IC₅₀ [μM] | | Fp |
|------|-----------|-----------|---|-----|
| | | CRL2813 | CRL2351 | (ratio to Z) |
| KY-689 | 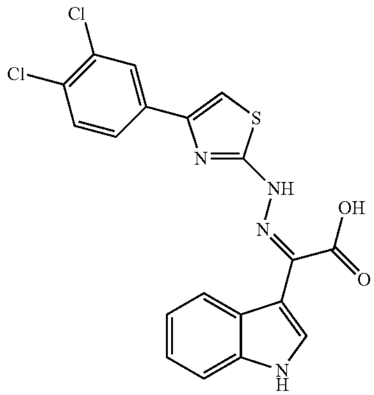 [SMILES: O=C(O)/C(=N\Nc1nc(-c2ccc(Cl)c(Cl)c2)cs1)c1c[nH]c2ccccc12] | >20 | >20 | 4 |
| KY-755-p | 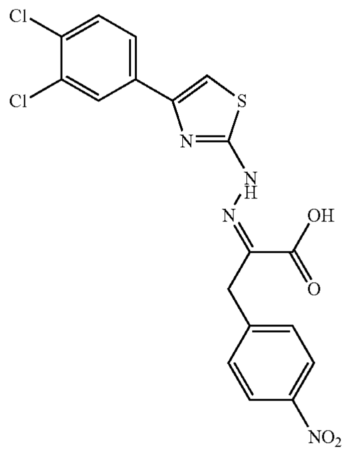 [SMILES: O=C(O)/C(Cc1ccc([N+](=O)[O-])cc1)=N\Nc1nc(-c2ccc(Cl)c(Cl)c2)cs1] | 5 | 15 | 1 |
| KY-612SF | 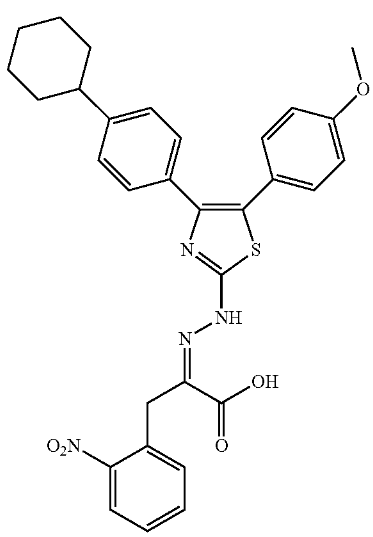 [SMILES: COc1ccc(-c2sc(N/N=C(/Cc3ccccc3[N+](=O)[O-])C(=O)O)nc2-c2ccc(C3CCCCC3)cc2)cc1] | 0.1 | | 1 |

-continued

| Code | Structure | IC$_{50}$ [μM] CRL2813 | CRL2351 | Fp (ratio to Z) |
|---|---|---|---|---|
| KY-612S | 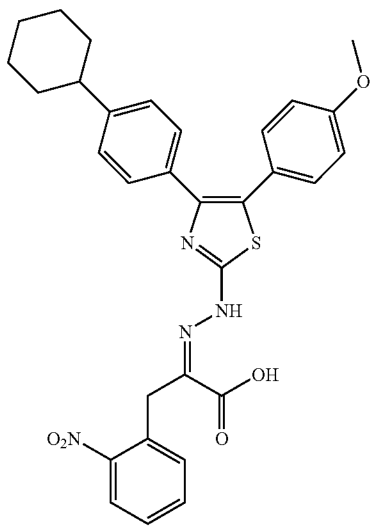 [SMILES: COc1ccc(-c2sc(N/N=C(/Cc3ccccc3[N+](=O)[O-])C(=O)O)nc2-c2ccc(C3CCCCC3)cc2)cc1] | 0.3 | 11 | 1.8 |
| KY-753 | 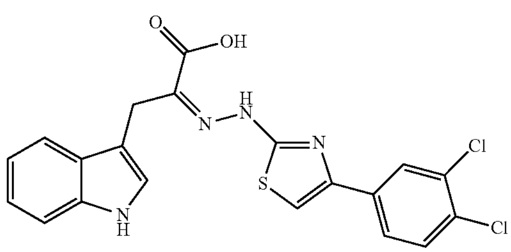 [SMILES: O=C(O)/C(Cc1c[nH]c2ccccc12)=N\Nc1nc(-c2ccc(Cl)c(Cl)c2)cs1] | 7.5 | 13.5 | 0.85 |
| KY-767 | 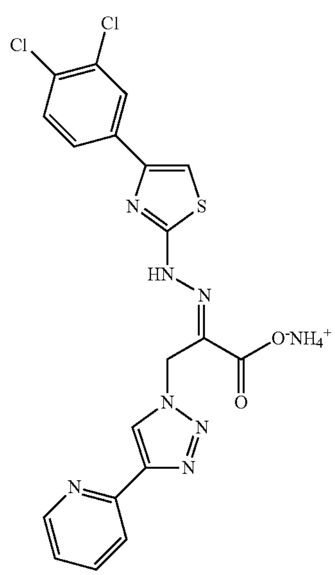 | 3.5 | 9 | 0.75 |

-continued

| Code | Structure | IC$_{50}$ [μM] | | Fp |
| | | CRL2813 | CRL2351 | (ratio to Z) |
| --- | --- | --- | --- | --- |
| KY-706bc | | 3 | 3.5 | 0.65 |
| KY-725 | | 3 | 3 | 0.7 |
| KY-782-Z | | 10 | 13 | 0.83 |
| KY-782-E | | 2.2 | 10 | 0.94 |

-continued

| Code | Structure | IC$_{50}$ [μM] CRL2813 | CRL2351 | Fp (ratio to Z) |
|---|---|---|---|---|
| KY-788-Z | 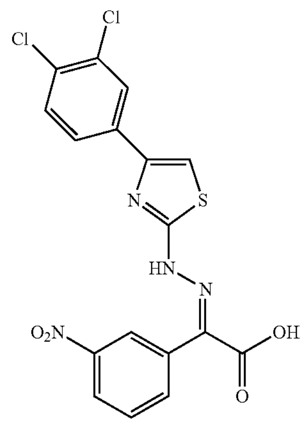 [SMILES: O=C(O)/C(=N/Nc1nc(-c2ccc(Cl)c(Cl)c2)cs1)c1cccc([N+](=O)[O-])c1] | | >20 | 0.86 |
| KY-788-E | 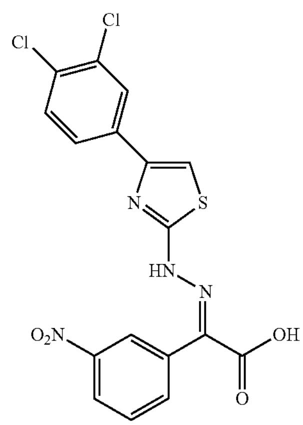 [SMILES: O=C(O)/C(=N/Nc1nc(-c2ccc(Cl)c(Cl)c2)cs1)c1cccc([N+](=O)[O-])c1] | 7 | 18 | 1.4 |
| RYF-273 | 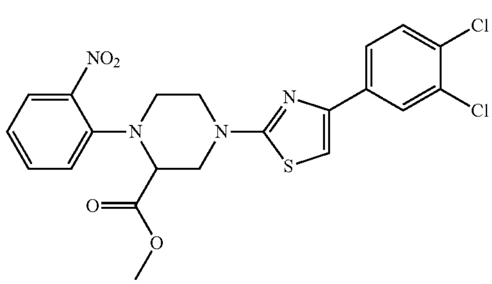 [SMILES: COC(=O)C1CN(c2nc(-c3ccc(Cl)c(Cl)c3)cs2)CCN1c1ccccc1[N+](=O)[O-]] | 3.5 | 0.54 | 0.55 |
| RYF-292 | 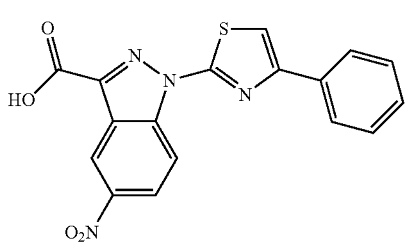 [SMILES: O=C(O)c1nn(-c2nc(-c3ccccc3)cs2)c2ccc([N+](=O)[O-])cc12] | 2.5 | 9.0 | 0.6 |

| Code | Structure | IC$_{50}$ [μM] CRL2813 | CRL2351 | Fp (ratio to Z) |
|---|---|---|---|---|
| RYF-440 | 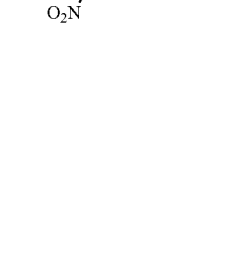 | Not tested | Not tested | 1.3 |
| RYF-339F |  | 1 | <0.54 | 2.0 |

EXAMPLE XIV

NMR Binding Experiments

Experiments were carried out with representative compounds to provide an indication of the ability of the compounds of the present invention to bind to eIF4E and therefore act as inhibitors of the binding of eIF4E to eIF4G. NMR spectra was recorded of the compounds at increasing concentrations of the protein and the disappearance of the compound signals was observed due to protein binding. At the same time, the spectrum of the protein appeared and increased. For example 4EGI-1 was titrated with D26eIF4E and compound KY-549 was titrated with GB 1-eIF4E. The decay provided a qualitative measure of affinity. Data for representative compounds (and structures) are provided in the table below showing that representative compounds bind eIF4E comparative to 4EGI-1:

| Compound | IC$_{50}$ Value |
|---|---|
| 4EGI-1 (Z-isomer) | about 4 μM |
| 4EGI-1 (E isomer) | about 13 μM |
| KY-549 | about 7 μM |
| KY-A6 | about 5 μM |
| KY-383 | about 3 μM |
| KY-720 | about 4 μM |

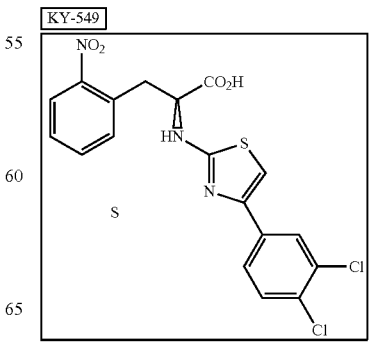

KY-549

| Compound | IC$_{50}$ Value |
|---|---|
| KY-A6 | |
| KY-383 | |
| KY-720 | |

Other embodiments will be evident to those of skill in the art. It should be understood that the foregoing description is provided for clarity only and is merely exemplary. The spirit and scope of the present invention are not limited to the above examples, but are encompassed by the following claims. All publications and patent applications cited above are incorporated by reference herein in their entirety for all purposes to the same extent as if each individual publication or patent application were specifically indicated to be so incorporated by reference.

What is claimed is:

1. A compound having the structure

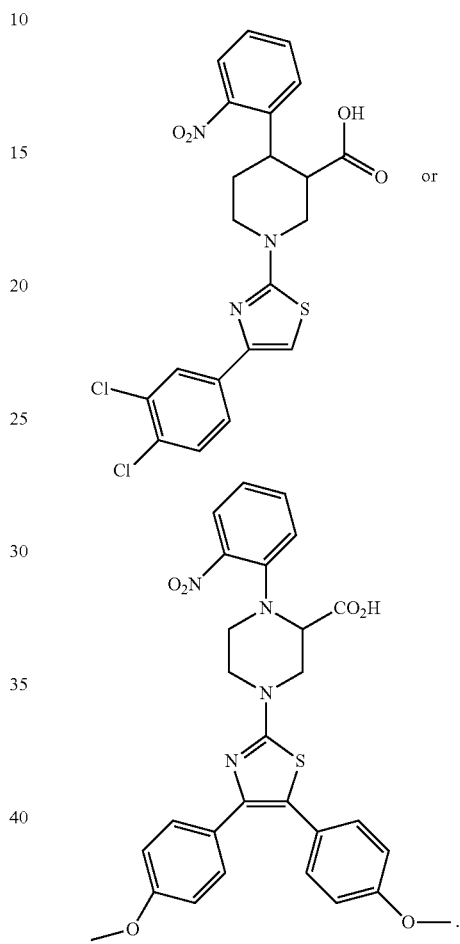

* * * * *